United States Patent
Kyle et al.

(10) Patent No.: US 9,120,752 B2
(45) Date of Patent: Sep. 1, 2015

(54) PYRIDINE COMPOUNDS AS SODIUM CHANNEL BLOCKERS

(75) Inventors: Donald J. Kyle, Yardley, PA (US); Chiyou Ni, Belle Mead, NJ (US); Minnie Park, Princeton Junction, NJ (US); Laykea Tafesse, Robbinsville, NJ (US)

(73) Assignee: Purdue Pharma, L.P., Stamford, CT (US)

(*) Notice: Subject to any disclaimer, the term of this patent is extended or adjusted under 35 U.S.C. 154(b) by 0 days.

(21) Appl. No.: 13/810,089

(22) PCT Filed: Jul. 15, 2011

(86) PCT No.: PCT/IB2011/001705
§ 371 (c)(1),
(2), (4) Date: Sep. 5, 2013

(87) PCT Pub. No.: WO2012/007836
PCT Pub. Date: Jan. 19, 2012

(65) Prior Publication Data
US 2013/0345211 A1 Dec. 26, 2013

Related U.S. Application Data

(60) Provisional application No. 61/365,085, filed on Jul. 16, 2010.

(51) Int. Cl.
| C07D 213/79 | (2006.01) |
| C07D 213/81 | (2006.01) |
| C07D 401/12 | (2006.01) |
| C07D 413/12 | (2006.01) |
| C07B 59/00 | (2006.01) |
| C07D 413/14 | (2006.01) |

(52) U.S. Cl.
CPC ............ *C07D 213/79* (2013.01); *C07B 59/002* (2013.01); *C07D 213/81* (2013.01); *C07D 401/12* (2013.01); *C07D 413/12* (2013.01); *C07D 413/14* (2013.01)

(58) Field of Classification Search
None
See application file for complete search history.

(56) References Cited

U.S. PATENT DOCUMENTS

| 4,555,520 | A | 11/1985 | Misra et al. |
| 6,040,311 | A | 3/2000 | Duggan et al. |
| 6,281,211 | B1 | 8/2001 | Cai et al. |
| 6,339,045 | B1 | 1/2002 | Kanno et al. |
| 7,393,872 | B2 | 7/2008 | Lan et al. |
| 2003/0055088 | A1 | 3/2003 | Shao et al. |
| 2003/0073724 | A1 | 4/2003 | Shao et al. |
| 2003/0125339 | A1 | 7/2003 | Chen et al. |
| 2004/0122237 | A1 | 6/2004 | Amiri et al. |
| 2004/0176374 | A1 | 9/2004 | Wunberg et al. |
| 2005/0031651 | A1 | 2/2005 | Gervais et al. |
| 2005/0234109 | A1 | 10/2005 | Yasukouchi et al. |
| 2006/0089375 | A1 | 4/2006 | Allen et al. |
| 2006/0122236 | A1 | 6/2006 | Wood et al. |
| 2006/0173050 | A1 | 8/2006 | Liu et al. |
| 2006/0241302 | A1 | 10/2006 | Kubota et al. |
| 2006/0281763 | A1 | 12/2006 | Axon et al. |
| 2007/0072874 | A1 | 3/2007 | Cui |
| 2007/0142430 | A1 | 6/2007 | Peukert et al. |
| 2008/0032972 | A1 | 2/2008 | Dorsey et al. |
| 2008/0139575 | A1 | 6/2008 | Lu et al. |
| 2009/0124654 | A1 | 5/2009 | Mjalli et al. |
| 2009/0149439 | A1 | 6/2009 | Miyauchi et al. |
| 2010/0056478 | A1 | 3/2010 | Desarbre et al. |
| 2010/0137606 | A1 | 6/2010 | Kiso et al. |
| 2011/0136831 | A1 | 6/2011 | Oda et al. |
| 2013/0012485 | A1 | 1/2013 | Baeschlin et al. |

(Continued)

FOREIGN PATENT DOCUMENTS

| EP | 1724278 A1 | 11/2006 |
| JP | 2008115166 | 5/2008 |

(Continued)

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Jordan, V. C. Nature Reviews: Drug Discovery, 2, 2003, 205-213.*
Anger. T., et al., "Medicinal Chemistry of Neuronal Voltage-Gated Sodium Channel Blockers," *J. Med. Chem.* 44(2):115-137, American Chemical Society, United States (2001).
Baker, M.D. and Wood, J.N., "Involvement of Na$^+$ channels in pain pathways," *Trends Pharmacol. Sci.* 22(1):27-31, Elsevier Science Ltd., England (2001).
Barthó, L., et al., "Involvement of capsaicin-sensitive neurones in hyperalgesia and enhanced opioid antinociception in inflammation," *Naunyn-Schmiedebergs Arch. Pharmacol.* 342(6):666-670, Springer-Verlag, Germany (1990).

(Continued)

*Primary Examiner* — Jeffrey S Lundgren
*Assistant Examiner* — William Lee
(74) *Attorney, Agent, or Firm* — Purdue Pharma, L.P.; Alan L. Koller; Weiying Yang

(57) ABSTRACT

The invention relates to substituted pyridine compounds of Formula I: (I) or a pharmaceutically acceptable salt, prodrug, or solvate thereof wherein $A^1$, X, $A^2$, $R^{1a}$, $R^{1b}$, $R^{1c}$, G, and z are defined as set forth in the specification. The invention is also directed to the use of compounds of Formula I to treat a disorder responsive to the blockade of sodium channels. Compounds of the present invention are especially useful for treating pain.

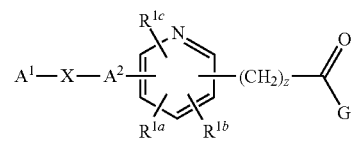

22 Claims, No Drawings

(56) References Cited

U.S. PATENT DOCUMENTS

| | | |
|---|---|---|
| 2013/0289044 A1 | 10/2013 | Goehring et al. |
| 2013/0296281 A1 | 11/2013 | Kyle et al. |
| 2013/0303526 A1 | 11/2013 | Ni et al. |
| 2014/0005212 A1 | 1/2014 | Ni et al. |

FOREIGN PATENT DOCUMENTS

| | | |
|---|---|---|
| WO | WO 98/47869 A1 | 10/1998 |
| WO | WO 99/26614 A1 | 6/1999 |
| WO | WO 00/57877 A1 | 10/2000 |
| WO | WO 01/68612 A2 | 9/2001 |
| WO | WO 01/72714 A2 | 10/2001 |
| WO | WO 02/100849 A2 | 12/2002 |
| WO | WO 03/022276 A1 | 3/2003 |
| WO | WO 03/022285 A1 | 3/2003 |
| WO | WO 03/059871 A1 | 7/2003 |
| WO | WO 03/082272 A1 | 10/2003 |
| WO | WO 2004/014844 A2 | 2/2004 |
| WO | WO 2004/016592 A1 | 2/2004 |
| WO | WO 2004/062553 A2 | 7/2004 |
| WO | WO 2004/089308 A2 | 10/2004 |
| WO | WO 2006/063167 A1 | 6/2006 |
| WO | WO 2006/068410 A1 | 6/2006 |
| WO | WO 2006/105222 A2 | 10/2006 |
| WO | WO 2006/110917 A2 | 10/2006 |
| WO | WO 2007/050522 A1 | 5/2007 |
| WO | WO 2007/083239 A1 | 7/2007 |
| WO | WO 2008/044217 A2 | 4/2008 |
| WO | WO 2008/068470 A1 | 6/2008 |
| WO | WO 2008/097991 A1 | 8/2008 |
| WO | WO 2008/135826 A3 | 11/2008 |
| WO | WO 2009/103032 A1 | 8/2009 |
| WO | WO 2009/147440 A1 | 12/2009 |
| WO | WO 2010/010380 A1 | 1/2010 |
| WO | WO 2010/051188 A1 | 5/2010 |
| WO | WO 2010/121164 A2 | 10/2010 |
| WO | WO 2012/007836 A1 | 1/2012 |
| WO | WO 2012/035421 A2 | 3/2012 |
| WO | WO 2012/085650 A1 | 6/2012 |
| WO | WO 2013/030665 A1 | 3/2013 |
| WO | WO 2013/064883 A1 | 5/2013 |
| WO | WO 2013/072758 A1 | 5/2013 |
| WO | WO 2013064884 A1 | 5/2013 |
| WO | WO 2013/136170 A1 | 9/2013 |

OTHER PUBLICATIONS

Benjamin, E.R., et al., "Validation of a Fluorescent Imaging Plate Reader Membrane Potential Assay for High-Throughput Screening of Glycine Transporter Modulators," *J. Biomol. Screen.* 10(4): 365-373, Sage Publications, United States (2005).

Bingham, A.L., et al., "Over one hundred solvates of sulfathiazole," *Chem. Commun.*: 603-604, The Royal Society of Chemistry, England (2001).

Black, J.A., et al., "Sensory neuron-specific sodium channel SNS is abnormally expressed in the brains of mice with experimental allergic encephalomyelitis and humans with multiple sclerosis," *Proc. Natl. Acad. Sci. USA* 97(21):11598-11602, National Academy of Sciences, United States (2000).

Brower, V., "New paths to pain relief," *Nat. Biotechnol.* 18(4):387-391, Nature America Publishing, United States (2000).

Brown, C.M., et al., "Neuroprotective properties of lifarizine compared with those of other agents in a mouse model of focal cerebral ischaemia," *Br. J. Pharmacol.* 115(8):1425-1432, Stockton Press, England (1995).

Bundgaard, H., "(C) Means to Enhance Penetration: (1) Prodrugs as a means to improve the delivery of peptide drugs," *Adv. Drug Delivery Revs.* 8:1-38, Elsevier Science Publishers, B.V., Netherlands (1992).

Caira, M.R., et al., "Preparation and Crystal Characterization of a Polymorph, a Monohydrate, and an Ethyl Acetate Solvate of the Antifungal Fluconazole," *J. Pharm. Sci.* 93(3):601-611, Wiley-Liss Inc. and the American Pharmacists Assn., United States (2004).

Cannon, S.C., "Spectrum of sodium channel disturbances in the nondystrophic myotonias and periodic paralyses," *Kidney Int.* 57(3):772-779, International Society of Nephrology, United States (2000).

Chahine, M., et al., "Voltage-Gated Sodium Channels in Neurological Disorders," *CNS Neurol. Disord. Drug Targets* 7(2):144-158, Bentham Science Publishers Ltd., United Arab Emirates (2008).

Catterall, W.A., "Common modes of drug action on $Na^+$ channels: local anesthetics, antiarrhythmics and anticonvulsants," *Trends Pharmacol. Sci.* 8:57-65, Elsevier Science Publishers, B.V., Netherlands (1987).

Clare, J.J., et al., "Voltage-gated sodium channels as therapeutic targets," *Drug Discov. Today* 5(11):506-520, Elsevier Science Ltd., England (2000).

Cummins, T.R., et al., "Slow Closed-State Inactivation: A Novel Mechanism Underlying Ramp Currents in Cells Expressing the hNE/PN1 Sodium Channel," *J. Neurosci.* 18(23):9607-9619, Society for Neuroscience, United States (1998).

Donaldson, I., "Tegretol: a double blind trial in tinnitus," *J. Laryngol. Otol.* 95(9):947-951, Cambridge University Press, England (1981).

Graham, S.H., et al., "Neuroprotective Effects of a Use-Dependent Blocker of Voltage-Dependent Sodium Channels, BW619C89, in Rat Middle Cerebral Artery Occlusion," *J. Pharmacol. Exp. Ther.* 269(2): 854-859, The American Society for Pharmacology and Experimental Therapeutics, United States (1994).

Hanks, J.H. and Wallace, R.E., "17131. Relation of Oxygen and Temperature in the Preservation of Tissues by Refrigeration," *Proc. Soc. Exp. Biol. Med.* 71(2):196200, Blackwell Science, United States (1949).

Harootunian, A.T., et al., "Fluorescence Ratio Imaging of Cytosolic Free $Na^+$ in Individual Fibroblasts and Lymphocytes," *J. Biol. Chem.* 264(32):19458-19467, The American Society for Biochemistry and Molecular Biology, United States (1989).

Hübner, C.A. and Jentsch, T.J., "Ion channel diseases," *Hum. Mol. Genet.* 11(20):2435-2445, Oxford University Press, England (2002).

Hunskaar, S., et al., "Formalin test in mice, a useful technique for evaluating mild analgesics," *J. Neurosci. Methods* 14(1):69-76, Elsevier Science Publishers B.V., Netherlands (1985).

Ilyin, V.I., et al., "V102862 (Co 102862): a potent, broad-spectrum state-dependent blocker of mammalian voltage-gated sodium channels," *Br. J. Pharmacol.* 144(6):801-812, Nature Publishing Group, England (2005).

Kakeya, N., et al., "Studies on Prodrugs of Cephalosporins. I. Synthesis and Biological Properties of Glycyloxybenzoyloxymethyl and Glycylaminobenzoyloxymethyl Esters of 7β-[2-(2-aminothiazol-4-yl)-(Z)-2-methoxyiminoacetamido]-3-methyl-3-cephem-4-carboxylic Acid," *Chem. Pharm. Bull.* (Tokyo) 32(2):692-698, Pharmaceutical Society of Japan, Japan (1984).

Kim, H-L., et al., "Rat brain expresses an alternatively spliced form of the dihydropyridine-sensitive L-type calcium channel α2 subunit," *Proc. Natl. Acad. Sci. USA* 89:3251-3255, National Academy of Sciences, United States (1992).

Kyle, D.J., and Ilyin, V.I., "Sodium Channel Blockers," *J. Med. Chem.* 50(11):2583-2588, American Chemical Society, United States (2007).

Lai, J., et al., "The role of voltage-gated sodium channels in neuropathic pain," *Curr. Opin. Neurobiol.* 13(3):291-297, Elsevier Science Ltd., England (2003).

Lai, J., et al., "Voltage-Gated Sodium Channels and Hyperalgesia," *Annu. Rev. Pharmacol. Toxicol.* 44:371-397, Annual Reviews, United States (2004).

Laird, J.M.A., et al., "Deficits in Visceral Pain and Referred Hyperalgesia in Nav1.8 (SNS/PN3)-Null Mice," *J. Neurosci.* 22(19):8352-8356, Society for Neuroscience, United States (2002).

Liu, H., et al., "Mutations in Cardiac Sodium Channels: Clinical Implications," *Am. J. Pharmacogenomics* 3(3):173-179, Adis Data Information BV, New Zealand (2003).

Majumdar, B., et al., "An electrocochleographic study of the effects of lignocaine on patients with tinnitus," *Clin. Otolaryngol. Allied Sci.* 8(3):175-180, Blackwell Scientific Publications, England (1983).

(56) References Cited

OTHER PUBLICATIONS

Meisler, M.H. and Kearney, J.A., "Sodium channel mutations in epilepsy and other neurological disorders," *J. Clin. Invest.* 115(8):2010-2017, American Society for Clinical Investigation, United States (2005).

Møller, A.R., "Similarities Between Chronic Pain and Tinnitus," *Am. J. Otol.* 18(5):577-585, Lippincott-Raven, United States (1997).

Nassar, M.A., et al., "Nociceptor-specific gene deletion reveals a major role for $Na_v1.7$ (PN1) in acute and inflammatory pain," *Proc. Natl. Acad. Sci. USA* 101(34):12706-12711, National Academy of Sciences, United States (2004).

Nielsen, N.M. and Bundgaard, H., "Glycolamide Esters as Biolabile Prodrugs of Carboxylic Acid Agents: Synthesis, Stability, Bioconversion, and Physicochemical Properties," *J. Pharm. Sci.* 77(4):285-298, American Pharmaceutical Assn., United States (1988).

Noble, D., "Unraveling the genetics and mechanisms of cardiac arrhythmia," *Proc. Natl. Acad. Sci. USA* 99(9):5755-5756, National Academy of Sciences, United States (2002).

Seltzer, Z., et al., "A novel behavioral model of neuropathic pain disorders produced in rats by partial sciatic nerve injury," *Pain* 43(2):205-218, Elsevier Science Publishers B.V., Netherlands (1990).

Shao, B., et al., "Phenoxyphenyl Pyridines as Novel State-Dependent, High-Potency Sodium Channel Inhibitors," *J. Med. Chem.* 47:4277-4285, American Chemical Society, United States (2004).

Simpson, J.J. and Davies, W.E., "Recent advances in the pharmacological treatment of tinnitus," *Trends Pharmacol. Sci.* 20(1):12-18, Elsevier Science, England (1999).

Srivatsa, U., et al., "Mechanisms of Antiarrhythmic Drug Actions and Their Clinical Relevance for Controlling Disorders of Cardiac Rhythm," *Curr. Cardiol. Rep.* 4(5):401-410, Current Science Inc., United States (2002).

Stein, C., et al., "Unilateral Inflammation of the Hindpaw in Rats as a Model of Prolonged Noxious Stimulation: Alterations in Behavior and Nociceptive Thresholds," *Pharmacol. Biochem. Behav.* 31:445-451, Pergamon Press plc, United States (1988).

Taylor, C.P. and Meldrum, B.S., "$Na^+$ channels as targets for neuroprotective drugs," *Trends Pharmacol. Sci.* 16(9):309-316, Elsevier Science Ltd., England (1995).

Toledo-Aral, J.J., et al., "Identification of PN1, a predominant voltage-dependent sodium channel expressed principally in peripheral neurons," *Proc. Natl. Acad. Sci. USA* 94(4):1527-1532, The National Academy of Sciences, United States (1997).

Tonndorf, J., "The analogy between tinnitus and pain: A suggestion for physiological basis of chronic tinnitus," *Hearing Research* 28(2-3):271-275, Elsevier Science Publishers B.V., Netherlands (1987).

Van Tonder, E.C., et al., "Preparation and Physicochemical Characterization of 5 Niclosamide Solvates and 1 Hemisolvate," *AAPS PharmSciTech* 5(1):1-10, Springer, United States (2004).

Wood, J.N., et al., "Voltage-Gated Sodium Channels and Pain Pathways," *J. Neurobiol.* 61(1):55-71, Wiley Periodicals, Inc., United States (2004).

Yogeeswari, P., et al., "Ion Channels as Important Targets for Antiepileptic Drug Design," *Curr. Drug Targets* 5(7):589-602, Bentham Science Publishers Ltd., Netherlands (2004).

Kim, S.H. and Chung, J.M., "An experimental model for peripheral neuropathy produced by segmental spinal nerve ligation in the rat," *Pain* 50:355-363, Elsevier Science Publishers B.V., Netherlands (1992).

NCBI Database GenBank Report, Accession No. NM_002977 (*Homo sapiens* sodium channel, voltage-gated, type IX, alpha subunit (SCN9A), mRNA, accessed on Aug. 1, 2013, accessed at http://www.ncbi.nlm.nih.gov/nuccore/NM_002977.

International Search Report for International Patent Application No. PCT/IB2011/001705, mailed Dec. 14, 2011, European Patent Office, Rijswijk, Netherlands.

International Preliminary Report on Patentability and the Written Opinion of the International Searching Authority for International Application No. PCT/IB2011/001705, issued Jan. 22, 2013, International Bureau of WIPO, Geneva, Switzerland.

Mannion et al., "Neuropathic pain: aetiology, symptoms, mechanisms, and management," *Lancet* 353(9168), 1959-1964 (1999).

Mason J.J. and Bergman, J., "Total synthesis of luotonin A and 14-substituted analogues," *Org. Biomol. Chem.* 5(15):2486-2490, The Royal Society of Chemistry, England (2007).

\* cited by examiner

PYRIDINE COMPOUNDS AS SODIUM CHANNEL BLOCKERS

BACKGROUND OF THE INVENTION

1. Field of the Invention

This invention is in the field of medicinal chemistry. The invention relates to novel substituted pyridine compounds and the use of these compounds as blockers of voltage-gated sodium ($Na^+$) channels.

2. Background Art

Voltage-gated sodium channels (VGSCs) are found in all excitable cells. In neuronal cells of the central nervous system (CNS) and peripheral nervous system (PNS) sodium channels are primarily responsible for generating the rapid upstroke of the action potential. In this manner sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.*, 61:55-71 (2004)).

VGSCs are composed of one α-subunit, that forms the core of the channel and is responsible for voltage-dependent gating and ion permeation, and several auxiliary β-subunits (see, e.g., Chahine et al., *CNS & Neurological Disorders-Drug Targets* 7:144-158 (2008) and Kyle and Ilyin., *J. Med. Chem.* 50:2583-2588 (2007)). α-Subunits are large proteins composed of four homologous domains. Each domain contains six α-helical transmembrane spanning segments. There are currently 9 known members of the family of voltage-gated sodium channel α-subunits. Names for this family include SCNx, SCNAx, and $Na_v x.x$ (see Table 1, below). The VGSC family has been phylogenetically divided into two subfamilies $Na_v 1.x$ (all but SCN6A) and $Na_v 2.x$ (SCN6A). The $Na_v 1.x$ subfamily can be functionally subdivided into two groups, those which are sensitive to blocking by tetrodotoxin (TTX-sensitive or TTX-s) and those which are resistant to blocking by tetrodotoxin (TX-resistant or TTX-r).

There are three members of the subgroup of TTX-resistant sodium channels. The SCN5A gene product ($Na_v 1.5$, Hl) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of $Na_v 1.5$ have found clinical utility in treatment of such disorders (Srivatsa et al., *Curr. Cardiol. Rep.* 4:401-410 (2002)). The remaining TTX-resistant sodium channels, $Na_v 1.8$ (SCNIOA, PN3, SNS) and $Na_v 1.9$ (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v 1.8$ has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v 1.8$-null mice exhibited typical nociceptive behavior in response to acute noxious stimulation but had significant deficits in referred pain and hyperalgesia (Laird et al., *J. Neurosci.* 22:8352-8356 (2002)).

TABLE 1

| Voltage-gated sodium channel gene family | | | | | |
|---|---|---|---|---|---|
| Type | Gene Symbol | Tissue Distribution | TTX $IC_{50}$ (nM) | Disease Association | Indications |
| $Na_v 1.1$ | SCN1A | CNS/PNS | 10 | Epilepsy | Pain, seizures, neurodegeneration |
| $Na_v 1.2$ | SCN2A | CNS | 10 | Epilepsy | Epilepsy, neurodegeneration |
| $Na_v 1.3$ | SCN3A | CNS | 15 | — | Pain |
| $Na_v 1.4$ | SCN4A | Skeletal muscle | 25 | Myotonia | Myotonia |
| $Na_v 1.5$ | SCN5A | Heart muscle | 2,000 | Arrhythmia | Arrhythmia |
| $Na_v 1.6$ | SCN8A | CNS/PNS | 6 | — | Pain, movement disorders |
| $Na_v 1.7$ | SCN9A | PNS | 25 | Erythermalgia | Pain |
| $Na_v 1.8$ | SCN10A | PNS | 50,000 | — | Pain |
| $Na_v 1.9$ | SCN11A | PNS | 1,000 | — | Pain |

The $Na_v 1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that $Na_v 1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenyloin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., *British J. Pharmacol.* 115:1425-1432 (1995)).

It has also been reported that sodium channel-blocking agents may be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin., *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erthermalgia and paroxysmal extreme pain disorder, familial hemiplegic migraine, and movement disorder; and the treatment of other psychiatric disorders such as autism, cerebellar atrophy, ataxia, and mental retardation; see, for example, Chahine et al., *CNS & Neurological Disorders-Drug Targets* 7:144-158 (2008) and Meisler and Kearney, *J. Clin. Invest.* 115:2010-2017 (2005). In addition to the above-mentioned clinical uses, carbamazepine, lidocaine and phenyloin are occasionally used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus, (Moller, *Am. J. Otol.* 18:577-585 (1997); Tonndorf, *Hear. Res.* 28:271-275 (1987)) it has been proposed that tinnitus should be viewed as a form of chronic pain sensation (Simpson, et al., *Tip.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

Many patients with either acute or chronic pain disorders respond poorly to current pain therapies and resistance or insensitivity to opiates is common. In addition, many of the currently available treatments have undesirable side effects. It has been reported that there is no treatment to prevent the development of neuropathic pain or to control established neuropathic pain (Mannion et al., *Lancet* 353:1959-1964 (1999)).

In view of the limited efficacy and/or unacceptable side-effects of the currently available agents, there is a pressing need for compounds that are potent, specific inhibitors of sodium channels implicated in neuropathic and other types of pain.

BRIEF SUMMARY OF THE INVENTION

The present invention is related to the use of substituted pyridine compounds represented by Formula I, below, and the pharmaceutically acceptable salts, prodrugs and solvates thereof, as blockers of sodium ($Na^+$) channels.

The invention is also related to treating a disorder responsive to the blockade of sodium channels in a mammal suffering from excess activity of said channels by administering an effective amount of a compound of Formula I, or a pharmaceutically acceptable salt, prodrug or solvate thereof, as described herein.

Some compounds useful in the present invention have not been heretofore reported. Thus, one aspect of the present invention is directed to novel compounds of Formula I, as well as their pharmaceutically acceptable salts, prodrugs and solvates.

Another aspect of the present invention is directed to the use of the novel compounds of Formula I, and their pharmaceutically acceptable salts, prodrugs and solvates, as blockers of sodium channels.

A further aspect of the present invention is to provide a method for treating pain (e.g., acute pain, chronic pain, which includes but is not limited to, neuropathic pain, postoperative pain, and inflammatory pain, or surgical pain) by administering an effective amount of a compound of Formula I, or a pharmaceutically acceptable salt, prodrug or solvate thereof, to a mammal in need of such treatment. Specifically, the present invention provides a method for preemptive or palliative treatment of pain by administering an effective amount of a compound of Formula I, or a pharmaceutically acceptable salt, prodrug or solvate thereof, to a mammal in need of such treatment.

A further aspect of the present invention is to provide a method for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, distonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, by administering an effective amount of a compound of Formula I, or a pharmaceutically acceptable salt, prodrug or solvate thereof, to a mammal in need of such treatment.

A further aspect of the present invention is to provide a pharmaceutical composition useful for treating a disorder responsive to the blockade of sodium ion channels, said pharmaceutical composition containing an effective amount of a compound of Formula I, or a pharmaceutically acceptable salt, prodrug or solvate thereof, in a mixture with one or more pharmaceutically acceptable carriers.

Also, an aspect of the invention is to provide a method of modulating sodium channels in a mammal, wherein said method comprises administering to the mammal an effective amount of at least one compound of Formula I, or a pharmaceutically acceptable salt, prodrug or solvate thereof.

A further aspect of the invention is to provide a compound of Formula I, or a pharmaceutically acceptable salt, prodrug or solvate thereof, for use in treating pain in a mammal, e.g., acute pain, chronic pain, which includes but is not limited to, neuropathic pain, postoperative pain, and inflammatory pain, or surgical pain.

A further aspect of the invention is to provide a compound of Formula I, or a pharmaceutically acceptable salt, prodrug or solvate thereof, for use in treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, distonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

A further aspect of the present invention is to provide radiolabeled compounds of Formula I and the use of such compounds, or their pharmaceutically acceptable salts, prodrugs or solvates, as radioligands for their binding site on the sodium channel.

A further aspect of the invention is to provide a method for screening a candidate compound for the ability to bind to a binding site on a protein using a radiolabeled compound of Formula I, which includes but is not limited to, a $^3H$, $^{11}C$, and $^{14}C$ radiolabeled compound of Formula I, or a pharmaceutically acceptable salt, prodrug or solvate thereof. This method comprises a) introducing a fixed concentration of the radiolabeled compound to a soluble or membrane-associated protein or fragment thereof to form a mixture under conditions which allow the radiolabeled compound to bind to a site on the protein or fragment thereof; b) titrating the mixture with a candidate compound; and c) determining the binding of the candidate compound to said binding site.

A further aspect of the invention is to provide the use of a compound of Formula I, or a pharmaceutically acceptable salt, prodrug or solvate thereof, in the manufacture of a medicament for treating pain in a mammal. In one embodiment, the invention provides the use of a compound of Formula I, or a pharmaceutically acceptable salt, prodrug or solvate thereof, in the manufacture of a medicament for palliative or preemptive treatment of pain, such as acute pain, chronic pain, or surgical pain.

A further aspect of the invention is to provide the use of a compound of Formula I, or a pharmaceutically acceptable salt, prodrug or solvate thereof, in the manufacture of a medicament for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, distonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention as claimed.

DETAILED DESCRIPTION OF THE INVENTION

One aspect of the present invention is based on the use of compounds of Formula I, and the pharmaceutically acceptable salts, prodrugs and solvates thereof, as blockers of $Na^+$ channels. In view of this property, compounds of Formula I, and the pharmaceutically acceptable salts, prodrugs and solvates thereof, are useful for treating disorders responsive to the blockade of sodium ion channels.

The compounds useful in this aspect of the invention are compounds represented by Formula I:

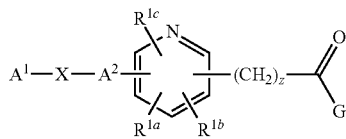

I or a pharmaceutically acceptable salt, prodrug, or solvate thereof, wherein:
A$^1$ is selected from the group consisting of:
a) cycloalkyl;
b) heterocyclo;
c) aryl; and
d) heteroaryl;
wherein any of a)-d) are optionally substituted;
X is selected from the group consisting of:
a) —O—;
b) —S—;
c) —SO—;
d) —SO$_2$—;
e) —(CR$^2$R$^3$)$_m$—; and
f) —NR$^4$—, wherein:
R$^2$ and R$^3$ are each independently selected from the group consisting of hydrogen and optionally substituted alkyl; or
R$^2$ and R$^3$ are taken together with the carbon atom to which they are attached to form a 3- to 8-membered cycloalkyl or heterocyclo, any one of which is optionally substituted;
m is 0, 1, 2, or 3; and
R$^4$ is selected from the group consisting of hydrogen and optionally substituted alkyl;
A$^2$ is selected from the group consisting of aryl and heteroaryl, either of which is optionally substituted; or
A$^2$ is absent;
R$^{1a}$, R$^{1b}$, and R$^{1c}$ are each independently selected from the group consisting of:
a) hydrogen;
b) halogen;
c) hydroxy;
d) cyano;
e) amino;
f) carboxamido;
g) optionally substituted alkyl;
h) alkoxy; and
i) haloalkoxy;
z is 0, 1, 2, 3, 4 or 5;
G is selected from the group consisting of:

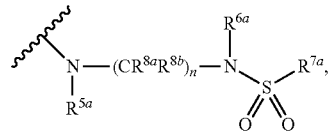

G-1

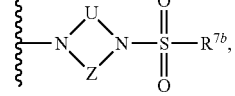

G-2

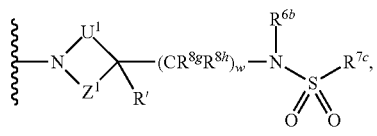

G-3

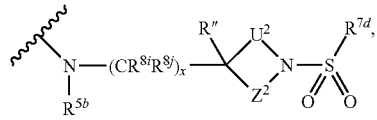

G-4

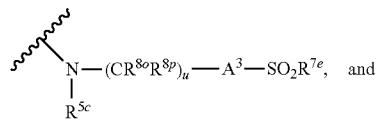

G-5

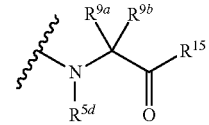

G-6 wherein:
R$^{5a}$, R$^{5b}$, R$^{5c}$, R$^{5d}$, R$^{6a}$, and R$^{6b}$ are each independently selected from the group consisting of hydrogen and optionally substituted alkyl;

$R^{9a}$ and $R^{9b}$ are each independently:
a) hydrogen;
b) alkyl;
c) alkenyl;
d) cycloalkyl;
e) heterocyclo;
f) aryl;
g) heteroaryl;
h) aralkyl; or
i) (heteroaryl)alkyl;
wherein any of b)-i) are optionally substituted; or
$R^{9a}$ and $R^{9b}$ taken together with the carbon atom to which they are attached form a 3- to 8-membered cycloalkyl or heterocyclo, any one of which is optionally substituted; or
$R^{5d}$ and $R^{9b}$ taken together form a 4- to 8-membered optionally substituted heterocyclo;
$R^{7a}$, $R^{7b}$, $R^{7c}$, $R^{7d}$, and $R^{7e}$ are each independently:
a) alkyl;
b) alkenyl;
c) cycloalkyl;
d) heterocyclo;
e) aryl;
f) heteroaryl;
g) aralkyl; or
h) (cycloalkyl)alkyl;
wherein any of a)-h) are optionally substituted, or
i) $NR^{11a}R^{11b}$;
wherein:
$R^{11a}$ and $R^{11b}$ are each independently:
a) hydrogen;
b) alkyl;
c) alkenyl;
d) cycloalkyl;
e) heterocyclo;
f) aryl;
g) heteroaryl; or
h) aralkyl;
wherein any of b)-h) are optionally substituted; or
$R^{11a}$ and $R^{11b}$ taken together with the nitrogen atom to which they are attached form a 4- to 8-membered optionally substituted heterocyclo;
$R^{8a}$ and $R^{8b}$ are each independently selected from the group consisting of hydrogen and optionally substituted alkyl; or
$R^{8a}$ and $R^{8b}$ taken together with the carbon atom to which the are attached form a 3- to 8-membered cycloalkyl or heterocyclo, any one of which is optionally substituted;
$R^{8c}$, $R^{8d}$, $R^{8e}$, $R^{8f}$, $R^{8g}$, $R^{8h}$, $R^{8i}$, $R^{8j}$, $R^{8k}$, $R^{8l}$, $R^{8m}$, $R^{8n}$, $R^{8o}$, and $R^{8p}$ are each independently selected from the group consisting of hydrogen and optionally substituted alkyl;
U is $—(CR^{8c}R^{8d})_o—$;
Z is $—(CR^{8e}R^{8f})_p—$;
$U^1$ is $—(CR^{8g}R^{8h})_q—$;
$Z^1$ is $—(CR^{8i}R^{8j})_r—$;
$U^2$ is $—(CR^{8k}R^{8l})_s—$;
$Z^2$ is $—(CR^{8m}R^{8n})_t—$;
n is 2, 3, 4, or 5;
o and p are each independently 2 or 3;
q, s, u, w, x, and y are each independently 0, 1, 2, or 3;
r and t are each independently 1, 2, or 3;
$R^{15}$ is selected from the group consisting of $—NR^{10a}R^{10b}$ and $—OR^{10e}$;
$R^{10a}$ and $R^{10b}$ are each independently:
a) hydrogen;
b) alkyl;
c) alkenyl;
d) cycloalkyl;
e) heterocyclo;
f) aryl;
g) heteroaryl; or
h) aralkyl;
wherein any of b)-h) are optionally substituted; or
$R^{10a}$ and $R^{10b}$ taken together with the nitrogen atom to which they are attached form a 4- to 8-membered optionally substituted heterocyclo;
$R^{10e}$ is independently selected from the group consisting of hydrogen and optionally substituted alkyl;
R' and R" are each independently:
a) hydrogen;
b) alkyl;
c) aryl;
wherein b) and c) are optionally substituted; and
$A^3$ is selected from the group consisting of:
a) phenyl;
b) pyridazinyl;
c) pyrimidinyl;
d) pyrazinyl; and
e) triazinyl;
wherein any of a)-b) are optionally substituted.

In one embodiment, when G of Formula I is G-5, then $A^2$ is selected from the group consisting of aryl and heteroaryl, either of which is optionally substituted.

In one embodiment, when $A^2$ of Formula I is absent and X of Formula I is —O— or $—NR^4—$, then $A^1$ is selected from the group consisting of cycloalkyl, heterocyclo, and aryl, any of which is optionally substituted.

In one embodiment, when $A^2$ of Formula I is absent, then X of Formula I is —O— and $A^1$ optionally substituted aryl.

In one embodiment, substituted pyridyl compounds useful in the present invention are compounds having Formula II:

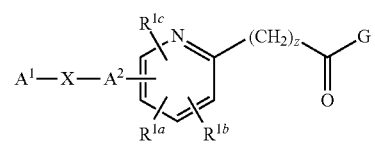

or a pharmaceutically acceptable salt, prodrug, or solvate thereof, wherein $A^1$, X, $A^2$, $R^{1a}$, $R^{1b}$, $R^{1c}$, G, and z are as defined above in connection with Formula I.

In one embodiment, substituted pyridyl compounds useful in the present invention are compounds having Formula III:

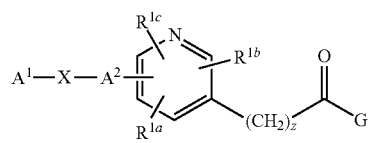

or a pharmaceutically acceptable salt, prodrug, or solvate thereof, wherein $A^1$, X, $A^2$, $R^{1a}$, $R^{1b}$, $R^{1c}$, G, and z are as defined above in connection with Formula I.

In one embodiment, substituted pyridyl compounds useful in the present invention are compounds having Formula IV:

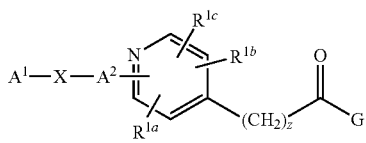

or a pharmaceutically acceptable salt, prodrug, or solvate thereof, wherein $A^1$, X, $A^2$, $R^{1a}$, $R^{1b}$, $R^{1c}$, G, and z are as defined above in connection with Formula I.

In one embodiment, substituted pyridyl compounds useful in the present invention are compounds of any of Formulae I-IV wherein z is 0 or 1.

In one embodiment, substituted pyridyl compounds useful in the present invention are compounds having Formula V:

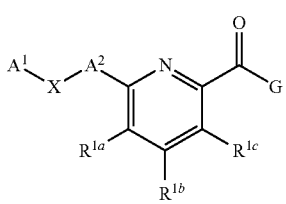

or a pharmaceutically acceptable salt, prodrug, or solvate thereof, wherein $A^1$, X, $A^2$, $R^{1a}$, $R^{1b}$, $R^{1c}$, and G are as defined above in connection with Formula I.

In one embodiment, substituted pyridyl compounds useful in the present invention are compounds having Formula VI:

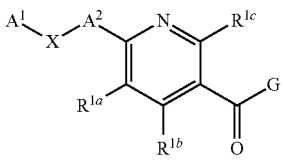

or a pharmaceutically acceptable salt, prodrug, or solvate thereof, wherein $A^1$, X, $A^2$, $R^{1a}$, $R^{1b}$, $R^{1c}$, and G are as defined above in connection with Formula I.

In one embodiment, substituted pyridyl compounds useful in the present invention are compounds having Formula VII:

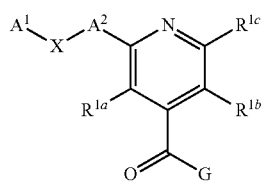

or a pharmaceutically acceptable salt, prodrug, or solvate thereof, wherein $A^1$, X, $A^2$, $R^{1a}$, $R^{1b}$, $R^{1c}$, and G are as defined above in connection with Formula I.

In one embodiment, substituted pyridyl compounds useful in the present invention are compounds of any of Formulae I-VII wherein:

$A^1$ is selected from the group consisting of phenyl and pyridyl, either of which is optionally substituted;

$A^2$ is optionally substituted phenyl or is absent; and

X is —O—.

In one embodiment, substituted pyridyl compounds useful in the present invention are compounds of any of Formulae I-VII, and in particular compounds of Formula V, wherein $A^2$ is optionally substituted phenyl and X is —O—.

In one embodiment, substituted pyridyl compounds useful in the present invention are compounds of any of Formulae I-VII, and in particular compounds of Formula V, wherein $A^2$ is an optionally substituted phenyl that is 1,4-disubstituted with respect to the pyridyl radical and X.

In one embodiment, substituted pyridyl compounds useful in the present invention are compounds of any of Formulae I-VII, and in particular compounds of Formula V, wherein $A^2$ is an optionally substituted phenyl that is 1,4-disubstituted with respect to the pyridyl radical and X, and $A^1$ is optionally substituted phenyl.

In one embodiment, substituted pyridyl compounds useful in the present invention are compounds of any of Formulae I-VII, and in particular compounds of Formula V, wherein $A^2$ is an optionally substituted phenyl that is 1,4-disubstituted with respect to the pyridyl radical and X, and $A^1$ is optionally substituted pyridyl.

In another embodiment, substituted pyridyl compounds useful in the present invention are compounds of Formula VIII:

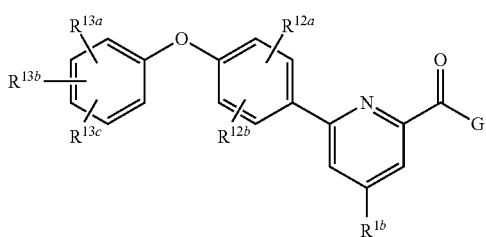

or a pharmaceutically acceptable salt, prodrug, or solvate thereof, wherein $R^{1b}$ and G are as defined above in connection with Formula I, and $R^{12a}$, $R^{12b}$, $R^{13a}$, $R^{13b}$, and $R^{13c}$ are each independently:
 a) hydrogen;
 b) halo;
 c) nitro;
 d) cyano;
 e) hydroxy;
 f) amino;
 g) haloalkyl;
 h) hydroxyalkyl;
 i) alkoxy;
 j) haloalkoxy;
 k) aryloxy;
 l) aralkyloxy;
 m) alkylthio;
 n) carboxamido;
 o) sulfonamido;
 p) alkyl;
 q) cycloalkyl;
 r) alkenyl;
 s) alkynyl;
 t) aryl;
 u) heteroaryl;
 v) heterocyclo; or
 w) aralkyl;
 wherein any of q)-w) are optionally substituted.

In one embodiment, substituted pyridyl compounds useful in the present invention are compounds of any of Formulae I-VIII, and in particular compounds of Formulae V or VIII, wherein $R^{1b}$ is selected from the group consisting of:

a) hydrogen, b) amino;

c) carboxamido; and d) optionally substituted alkyl (such as, e.g., monohydroxyalkyl and dihydroxyalkyl groups). In a particular embodiment, $R^{1b}$ is hydrogen or dihydroxyalkyl, e.g., 1,2-dihydroxyethyl.

In one embodiment, substituted pyridyl compounds useful in the present invention are compounds of any of Formulae I-VIII, and in particular compounds of Formulae V or VIII, wherein $R^{12a}$ and $R^{12b}$ are hydrogen, and $R^{13a}$, $R^{13b}$, and $R^{13}$ are each independently selected from the group consisting of:

a) hydrogen;

b) halogen;

c) haloalkyl;

d) alkoxy;

e) haloalkoxy; and f) alkyl.

In one embodiment, substituted pyridyl compounds useful in the present invention are compounds of any of Formulae I-VIII, and in particular compounds of Formulae V or VIII, wherein G is selected from the group consisting of:

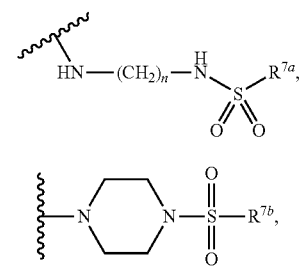
G-7

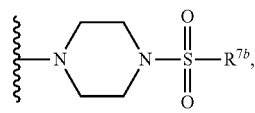
G-8

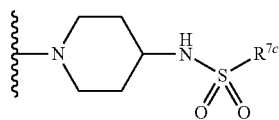
G-9

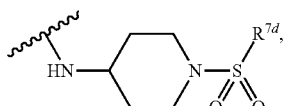
G-10

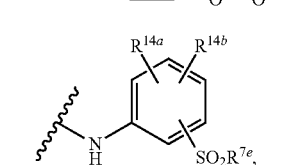
G-11

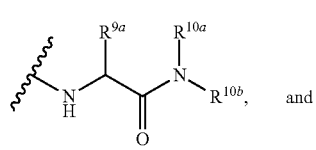
G-12 and

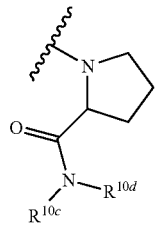
G-13 or a pharmaceutically acceptable salt, prodrug, or solvate thereof, wherein $R^{7a}$, $R^{7b}$, $R^{7c}$, $R^{7d}$, $R^{7e}$, $R^{9a}$, $R^{10a}$, $R^{10b}$ and n are as defined above in connection with Formula I, $R^{10c}$ and $R^{10d}$ are each independently selected from the group consisting of:

a) hydrogen;

b) alkyl;

c) alkenyl;

d) cycloalkyl, e) heterocyclo;

f) aryl;

g) heteroaryl;

h) aralkyl;

wherein any of b)-h) are optionally substituted; or $R^{10c}$ and $R^{10d}$ taken together with the nitrogen atom to which they are attached form a 4- to 8-membered optionally substituted heterocyclo; and $R^{14a}$ and $R^{14b}$ are each independently selected from the group consisting of:

a) hydrogen;

b) halogen;

c) hydroxy;

d) cyano;

e) alkyl;

f) haloalkyl;

g) hydroxyalkyl;

h) alkoxy; and i) haloalkoxy.

In one embodiment, substituted pyridyl compounds useful in the present invention are compounds of any of Formulae I-VIII, and in particular compounds of Formulae V or VIII, wherein G is selected from the group consisting of:

G-8

G-11

G-12 or a pharmaceutically acceptable salt, prodrug, or solvate thereof, wherein $R^{7b}$, $R^{7e}$, $R^{9a}$, $R^{10a}$ and $R^{10b}$ are as defined above in connection with Formula I and $R^{14a}$ and $R^{14b}$ are as defined immediately above.

In one embodiment, substituted pyridyl compounds useful in the present invention are compounds of any of Formulae I-VIII, and in particular compounds of Formulae V or VIII, wherein G is:

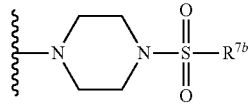

G-8 or a pharmaceutically acceptable salt, prodrug, or solvate thereof, wherein $R^{7b}$ is as defined above in connection with Formula I. In another embodiment, $R^{7b}$ is selected from the group consisting of aryl and heteroaryl, either of which is optionally substituted.

In one embodiment, substituted pyridyl compounds useful in the present invention are compounds of Formula IX:

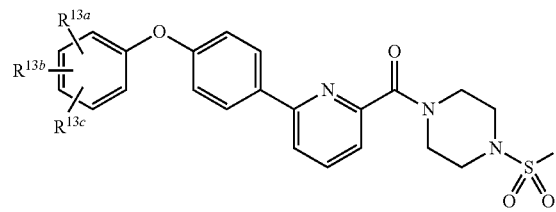

IX or a pharmaceutically acceptable salt, prodrug, or solvate thereof, wherein $R^{7b}$ is as defined above in connection with Formula I and $R^{13a}$, $R^{13b}$, and $R^{13c}$ are as defined in connection with Formula VIII.

In one embodiment, substituted pyridyl compounds useful in the present invention are compounds of any of Formulae I-VIII, and in particular compounds of Formulae V or VIII, wherein G is:

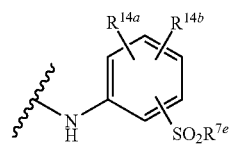

G-11 or a pharmaceutically acceptable salt, prodrug, or solvate thereof, wherein $R^{7e}$ is as defined above in connection with Formula I, and $R^{14a}$ and $R^{14b}$ are as defined above. In one embodiment, $R^{7e}$ is $NR^{11a}R^{11b}$, wherein $R^{11a}$ and $R^{11b}$ are each independently selected from the group consisting of hydrogen and $C_1$-$C_4$ alkyl.

In one embodiment, substituted pyridyl compounds useful in the present invention are compounds of Formula X:

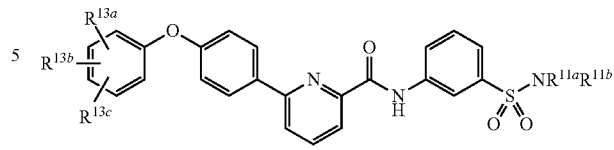

X or a pharmaceutically acceptable salt, prodrug, or solvate thereof, wherein $R^{11a}$ and $R^{11b}$ are each independently selected from the group consisting of hydrogen and $C_1$-$C_4$ alkyl, and $R^{13a}$, $R^{13b}$, and $R^{13c}$ are as defined in connection with Formula VIII.

In one embodiment, substituted pyridyl compounds useful in the present invention are compounds of any of Formulae I-VIII, and in particular compounds of Formulae V or VIII, wherein G is:

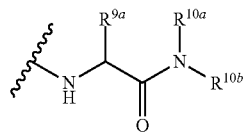

G-12 or a pharmaceutically acceptable salt, prodrug, or solvate thereof, wherein $R^{9a}$, $R^{10a}$, and $R^{10b}$ are as defined above in connection with Formula I. In another embodiment, $R^{9a}$ is selected from the group consisting of:

a) alkyl;

b) aralkyl; and c) (heteroaryl)alkyl;

wherein any of a)-c) are optionally substituted, and $R^{10a}$ and $R^{10b}$ are each independently selected from the group consisting of hydrogen and $C_1$-$C_4$ alkyl.

In one embodiment, substituted pyridyl compounds useful in the present invention are compounds of Formula XI:

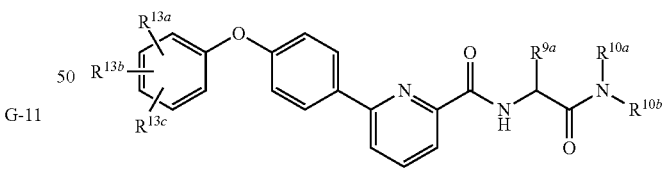

XI or a pharmaceutically acceptable salt, prodrug, or solvate thereof, wherein $R^{9a}$ is selected from the group consisting of:

a) alkyl;

b) aralkyl; and c) (heteroaryl)alkyl;

wherein any of a)-c) is optionally substituted, and $R^{10a}$ and $R^{10b}$ are each independently selected from the group consisting of hydrogen and $C_1$-$C_4$ alkyl, and $R^{13a}$, $R^{13b}$, and $R^{13c}$ are as defined in connection with Formula VIII.

In one embodiment, substituted pyridyl compounds useful in the present invention are compounds of Formula XII:

XII or a pharmaceutically acceptable salt, prodrug, or solvate thereof, wherein $R^{9a}$ is selected from the group consisting of:
a) alkyl;
b) aralkyl; and
c) (heteroaryl)alkyl;
wherein any of a)-c) are optionally substituted, and $R^{10a}$ and $R^{10b}$ are each independently selected from the group consisting of hydrogen and $C_1$-$C_4$ alkyl, and $R^{13a}$, $R^{13b}$, and $R^{13c}$ are as defined in connection with Formula VIII.

In one embodiment, substituted pyridyl compounds useful in the present invention are compounds of Formula XIII:

XIII or a pharmaceutically acceptable salt, prodrug, or solvate thereof, wherein $R^{9a}$ is selected from the group consisting of:
a) alkyl;
b) aralkyl; and
c) (heteroaryl)alkyl;
wherein any of a)-c) are optionally substituted, and $R^{10a}$ and $R^{10b}$ are each independently selected from the group consisting of hydrogen and $C_1$-$C_4$ alkyl, and $R^{13a}$, $R^{13b}$, and $R^{13c}$ are as defined in connection with Formula VIII.

In one embodiment, substituted pyridyl compounds useful in the present invention are compounds of Formulae XII and XIII, and or a pharmaceutically acceptable salt, prodrug, or solvate thereof, wherein $R^{9a}$ is optionally substituted alkyl, including hydroxyalkyl, and $R^{10a}$ and $R^{10b}$ are each hydrogen.

In one embodiment, substituted pyridyl compounds useful in the present invention include:
(6-(4(4-fluorophenoxy)phenyl)pyridin-2-yl)(4-((4-(trifluoromethoxy)phenyl)sulfonyl)piperazin-1-yl)methanone,
(6-(4-(4-fluorophenoxy)phenyl)pyridin-2-yl)(4-((3-(methylsulfonyl)phenyl)sulfonyl)piperazin-1-yl)methanone,
2,2,2-trifluoro-1-(7-((4-(6-(4-(4-fluorophenoxy)phenyl)picolinoyl)piperazin-1-yl)sulfonyl)-3,4-dihydroisoquinolin-2(1H)-yl)ethanone,
3-((4-(6-(4-(4-fluorophenoxy)phenyl)picolinoyl)piperazin-1-yl)sulfonyl)benzonitrile,
4-(6-(4-(4-fluorophenoxy)phenyl)picolinoyl)-N,N-dimethyl-piperazine-1-sulfonamide,
1-(((4-(6-(4(4-fluorophenoxy)phenyl)picolinoyl)piperazin-1-yl)sulfonyl)methyl)-7,7-dimethylbicyclo[2.2.1]heptan-2-one,
6-(4(4-fluorophenoxy)phenyl)pyridin-2-yl)(4-(methylsulfonyl)piperazin-1-yl)methanone,
(4-((3,5-dimethylisoxazol-4-yl)sulfonyl)piperazin-1-yl)(6-(4-(4-fluorophenoxy)phenyl)pyridin-2-yl)methanone,
(6-(4-(4-fluorophenoxy)phenyl)pyridin-2-yl)(4-(pyridin-3-ylsulfonyl)piperazin-1-yl)methanone,
(6-(4(4-fluorophenoxy)phenyl)pyridin-2-yl)(4-((3-(trifluoromethoxy)phenyl)sulfonyl)piperazin-1-yl)methanone,
4-((4 (6-(4-(4-fluorophenoxy)phenyl)picolinoyl)piperazin-1-yl)sulfonyl)benzonitrile,
3-((4-(6(4(4-fluorophenoxy)phenyl)picolinoyl)piperazin-1-yl)sulfonyl)benzoic acid,
4-((4-(6-(4-(4-fluorophenoxy)phenyl)picolinoyl)piperazin-1-yl)sulfonyl)benzoic acid,
2-fluoro-5-((4-(6-(4-(4-fluorophenoxy)phenyl)picolinoyl)piperazin-1-yl)sulfonyl)benzonitrile,
(6-(4-(4-fluorophenoxy)phenyl)pyridin-2-yl)(4-((4-methyl-3,4-dihydro-2H-benzo[b][1,4]oxazin-7-yl)sulfonyl)piperazin-1-yl)methanone,
6-(4-(4-fluorophenoxy)phenyl)-N-(2-(methylsulfonamido)ethyl)picolinamide,
6-(4-(4-fluorophenoxy)phenyl)-N-(2-(pyridine-3-sulfonamido)ethyl)picolinamide,
6-(4-fluorophenoxy)phenyl)-N-(2-(3-(methylsulfonyl)phenylsulfonamido)ethyl)picolinamide,
N-(2-(3-cyanophenylsulfonamido)ethyl)-6-(4-(4-fluorophenoxy)phenyl)picolinamide,
2-(2-{6-[4-(4-fluoro-phenoxy)-phenyl]-pyridin-2-yl}-acetylamino-propionic acid methyl ester,
2-(2-{6-[4-(4-fluoro-phenoxy)-phenyl]-pyridin-2-yl}-acetylamino-propionic acid,
6-[4-(4-fluoro-phenoxy)-phenyl]-pyridine-2-carboxylic acid [1-carbamoyl-2-(1H-indol-3-yl)-ethyl]-amide,
6-[4-(4-fluoro-phenoxy)-phenyl]-pyridine-2-carboxylic acid (1-carbamoyl-ethyl)-amide,
2-({6-[4-(4-fluoro-phenoxy)-phenyl]-pyridine-2-carbonyl}-amino)-succinamide,
6-[4-(4-fluoro-phenoxy)-phenyl]-pyridine-2-carboxylic acid (1-carbamoyl-2-hydroxyl-ethyl)-amide,
6-[4-(4-fluoro-phenoxy)-phenyl]-pyridine-2-carboxylic acid (1-carbamoyl-2-phenyl-ethyl)-amide,
1-{6-[4-(4-fluoro-phenoxy)-phenyl]-pyridine-2-carbonyl}-pyrrolidine-2-carboxylic acid amide,
6-[4-(4-fluoro-phenoxy)-phenyl]-pyridine-2-carboxylic acid (1-carbamoyl-2-hydroxy-propyl)-amide,
6-[4-(4-fluoro-phenoxy)-phenyl]-pyridine-2-carboxylic acid (1-carbamoyl-3-methyl-butyl)-amide,
N-(1-amino-1-oxo-3-(pyridin-3-yl)propan-2-yl)-6-(4-(4-fluorophenoxy)phenyl)picolinamide,
6-[4-(4-fluoro-phenoxy)-phenyl]-pyridine-2-carboxylic acid (1-carbamoyl-2-methyl-propyl)-amide,
6-[4 (4-fluoro-phenoxy)-phenyl]-pyridine-2-carboxylic acid (1-carbamoyl-2-hydroxy-ethyl)-amide,
6-[4-(4-fluoro-phenoxy)-phenyl]-pyridine-2-carboxylic acid [1-carbamoyl-2-(4-hydroxy-phenyl)-ethyl]-amide,
6-[4-(4-fluoro-phenoxy)-phenyl]-pyridine-2-carboxylic acid [1-carbamoyl-2-(1H-imidazol-4-yl)-ethyl]-amide,
N-(1,6-diamino-1-oxohexan-2-yl)-6-(4-(4-fluorophenoxy)phenyl)picolinamide,
2-(6-(4-(4-(trifluoromethyl)phenoxy)phenyl)picolinamido)succinamide,
2-(6-(4-(4-(trifluoromethyl)phenoxy)phenyl)picolinamido)pentanediamide,
3-((4-(6-(4-fluorophenoxy)picolinoyl)piperazin-1-yl)sulfonyl)benzonitrile,
3-((4-(6-(4-fluorophenyl)picolinoyl)piperazin-1-yl)sulfonyl)benzonitrile, 3-((4-(4-(1,2-dihydroxyethyl)-6-(4-(4-fluorophenoxy)phenyl)picolinoyl)piperazin-1-yl)sulfonyl)benzonitrile, N-(1-amino-1-oxopropan-2-yl)-6-(4-((5-(trifluoromethyl)pyridin-2-yl)oxy)phenyl)picolinamide, N-1-amino-4-methyl-1-oxopentan-2-yl)-4-(1,2-dihydroxyethyl)-6-(4-(4-fluorophenoxy)phenyl)picolinamide, 2-(4-(1,2-dihydroxyethyl)-6-(4-(4-fluorophenoxy)phenyl)picolinamido)succinamide, N-(1-amino-4-methyl-1-oxopentan-2-yl)-4-(1,2-dihydroxyethyl)-6-(4-(4-fluorophenoxy)phenyl)picolinamide, and 2-(4-(1,2-dihydroxyethyl)-6-(4-(4-fluorophenoxy)phenyl)picolinamido)succinamide, or isomers, e.g., enantiomers, thereof, or a pharmaceutically acceptable salt, prodrug, or solvate thereof.

In one embodiment, substituted pyridyl compounds useful in the present invention include:

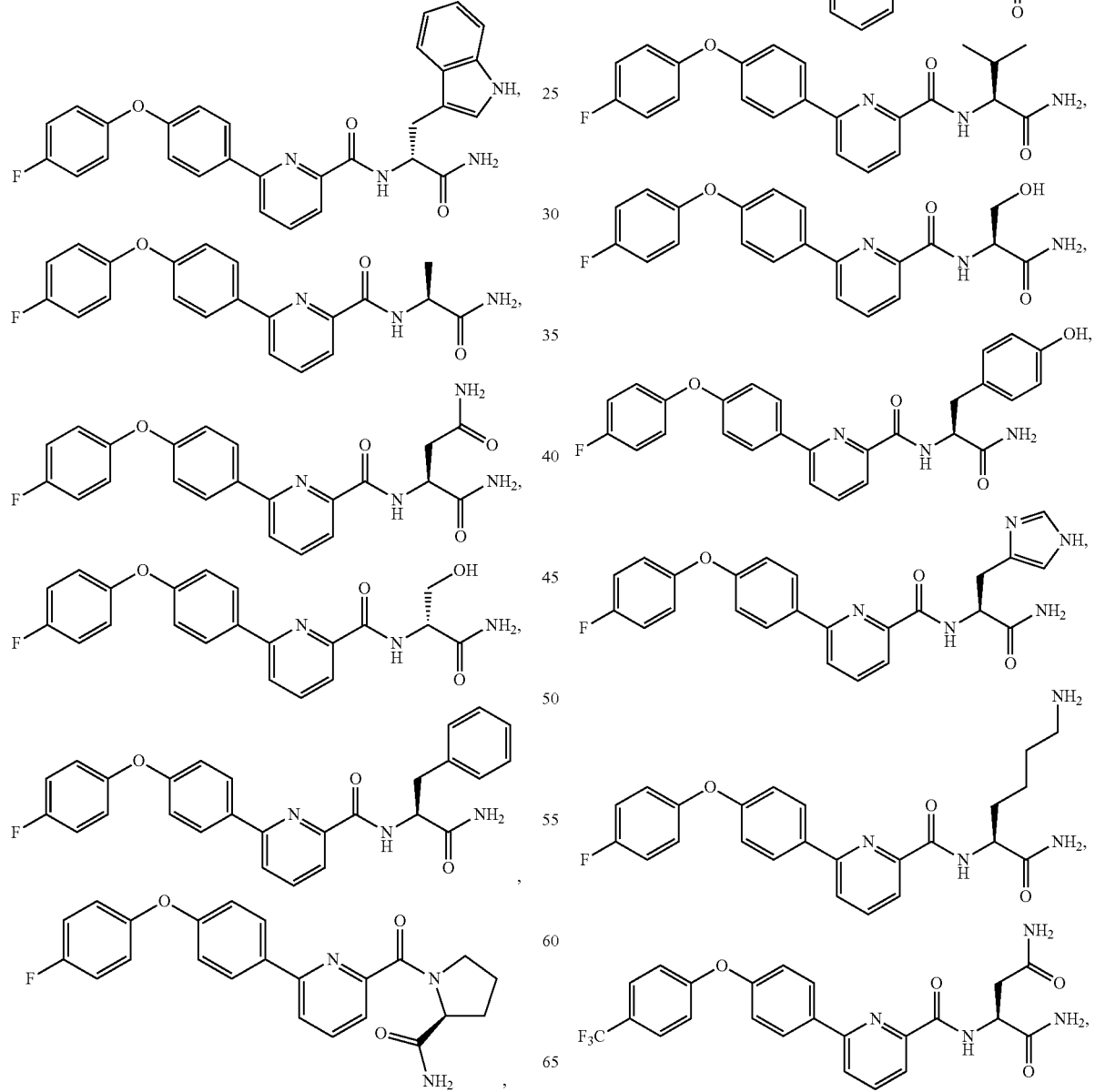

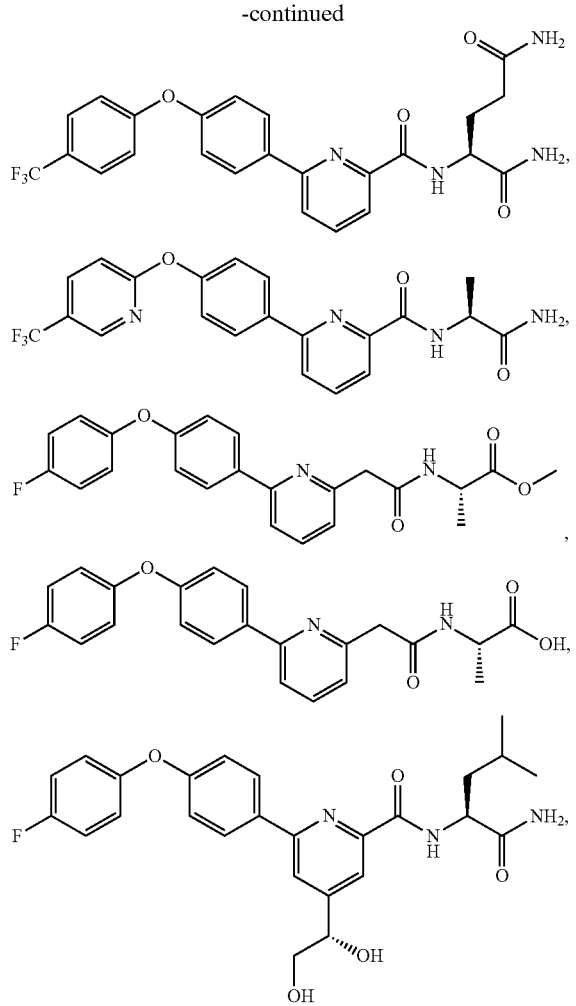
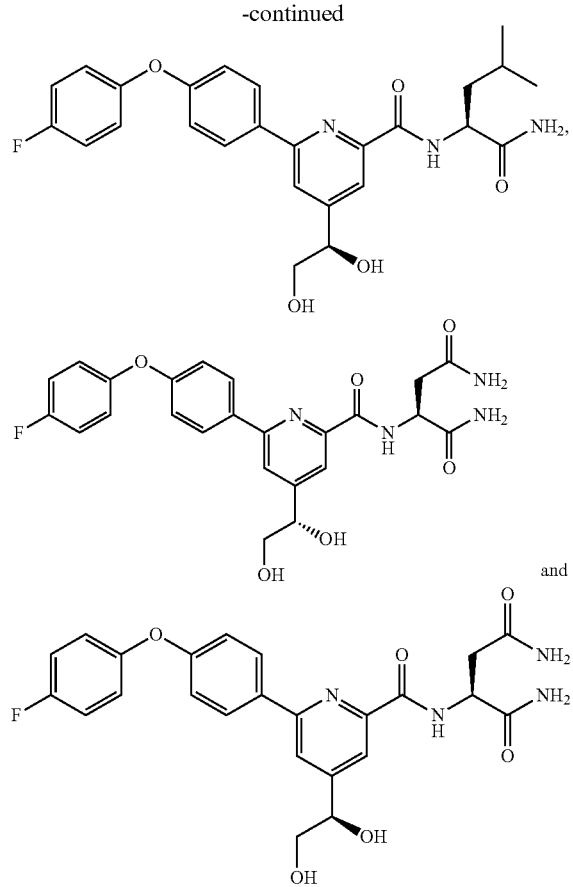
or a pharmaceutically acceptable salt, prodrug, or solvate thereof.
In one embodiment, substituted pyridyl compounds useful in the present invention are selected from the group consisting of:
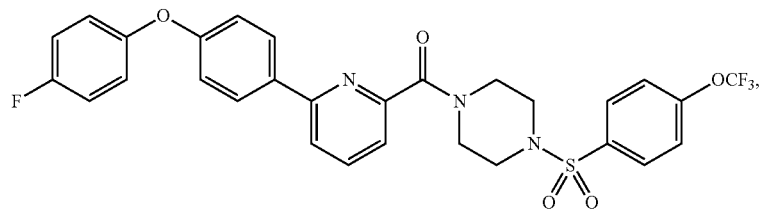
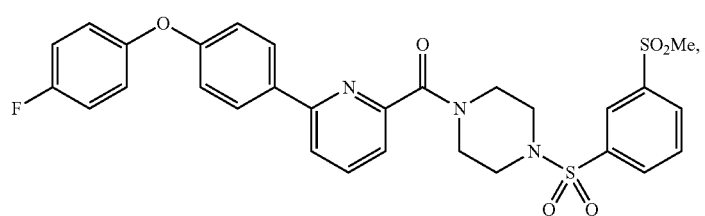

-continued
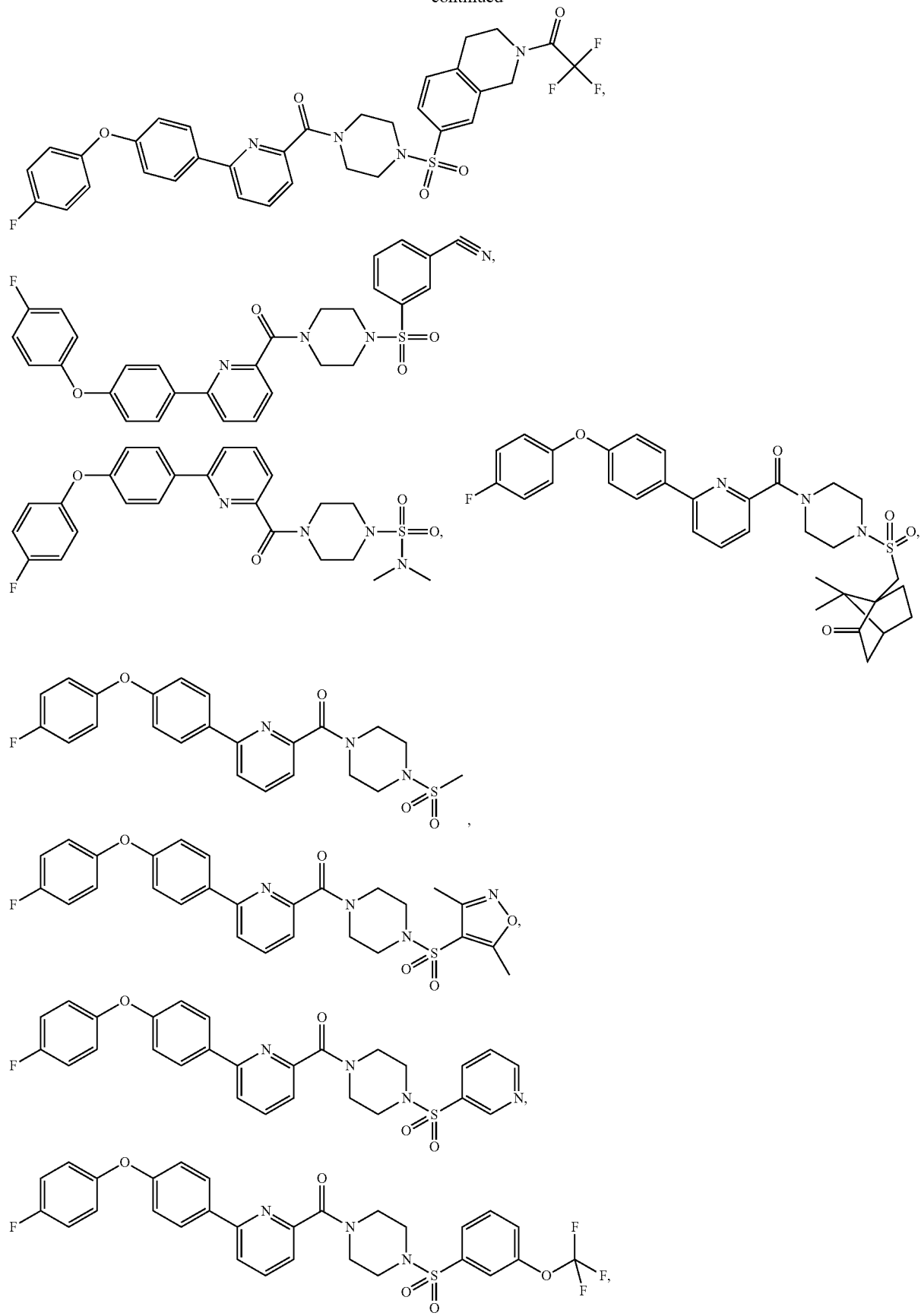

-continued
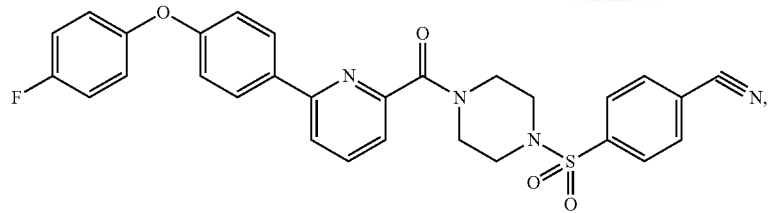
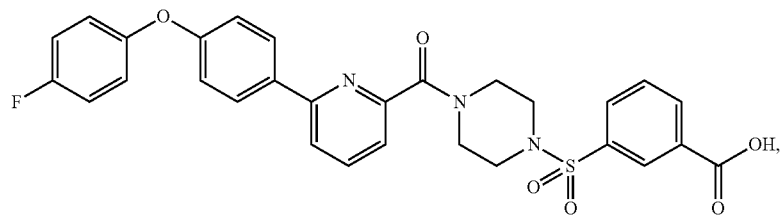
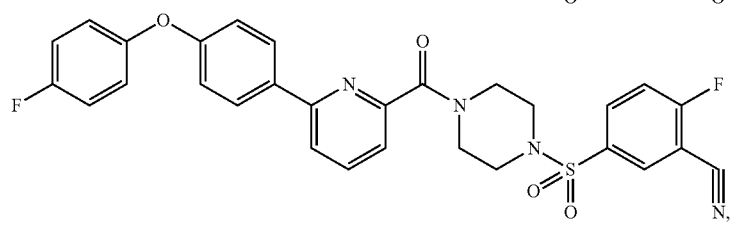
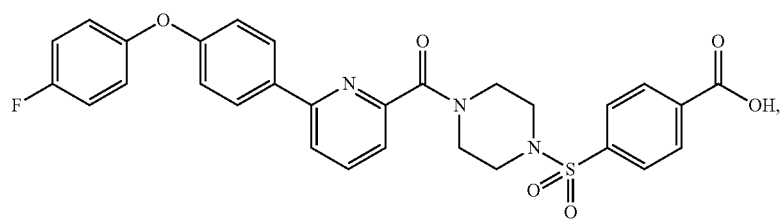
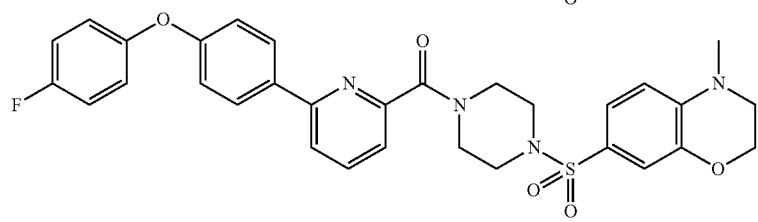
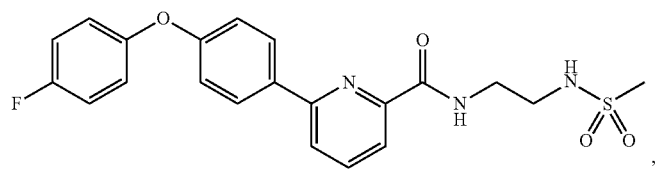
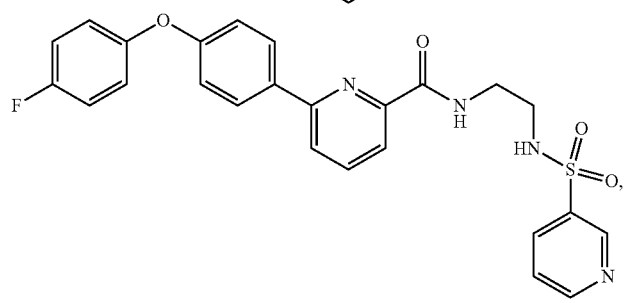

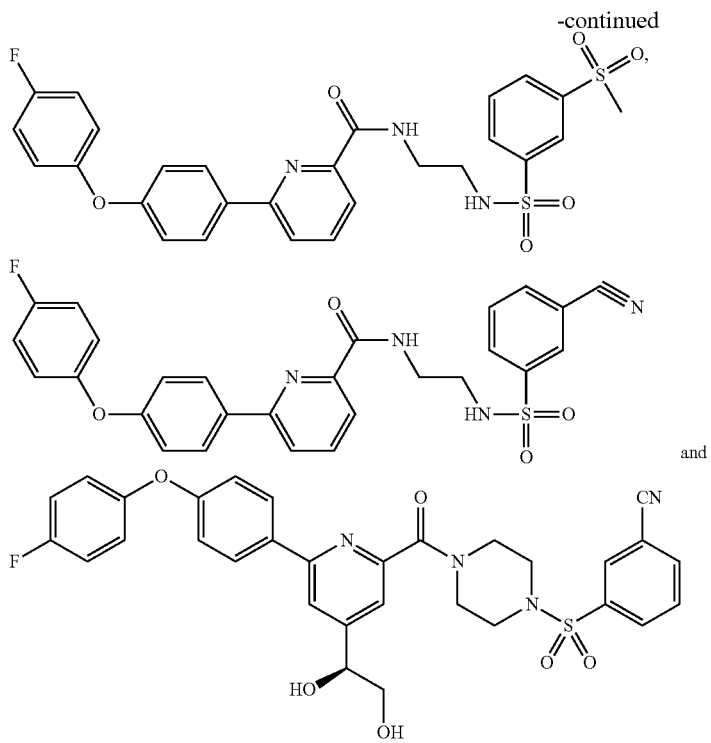

or a pharmaceutically acceptable salt, prodrug, or solvate thereof.

In one embodiment, substituted pyridyl compounds useful in the present invention are selected from the group consisting of:

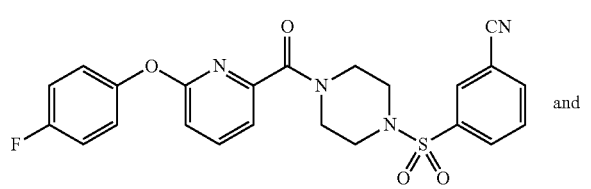

and

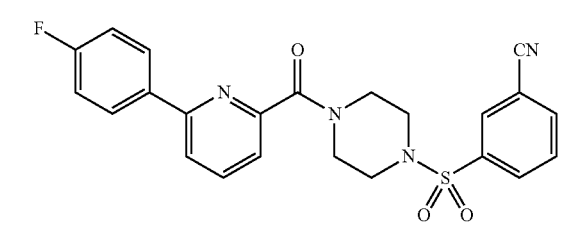

or a pharmaceutically acceptable salt, prodrug, or solvate thereof.

In one embodiment, a substituted pyridyl compound useful in the present invention is:

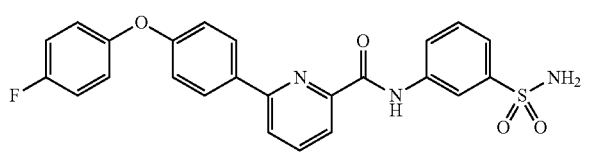 [SMILES: NS(=O)(=O)c1cccc(NC(=O)c2cccc(-c3ccc(Oc4ccc(F)cc4)cc3)n2)c1]

or a pharmaceutically acceptable salt, prodrug, or solvate thereof.

Useful alkyl groups are selected from straight- and branched-chain $C_{1-10}$ alkyl groups. Typical $C_{1-10}$ alkyl groups include methyl, ethyl, propyl, isopropyl, butyl, sec-butyl, tert-butyl, iso-butyl, 3-pentyl, hexyl, heptyl, octyl, nonyl and decyl, among others. In one embodiment, useful alkyl groups are selected from straight chain $C_{1-6}$ alkyl groups and branched chain $C_{1-6}$ alkyl groups. Typical $C_{1-6}$ alkyl groups include methyl, ethyl, propyl, isopropyl, butyl, sec-butyl, tert-butyl, iso-butyl, 3-pentyl, and hexyl, among others. In one embodiment, useful alkyl groups are selected from straight chain $C_{1-4}$ alkyl groups and branched chain $C_{1-4}$ alkyl groups. Typical $C_{1-4}$ alkyl groups include methyl, ethyl, propyl, isopropyl, butyl, sec-butyl, tert-butyl, and iso-butyl. Unless stated otherwise specifically in the specification, the alkyl groups defined above may be optionally substituted by 1, 2, or 3 optional substituents.

Useful cycloalkyl groups are selected from saturated and partially unsaturated (containing one or two double bonds) cyclic hydrocarbon groups containing one to three rings having from three to twelve carbon atoms (i.e., $C_3$-$C_{12}$ cycloalkyl) or the number of carbons designated. In one embodiment, the cycloalkyl has one or two rings. In another embodiment, the cycloalkyl is a $C_3$-$C_8$ cycloalkyl. Exemplary cycloalkyl groups include cyclopropyl, cyclobutyl, cyclopentyl, cyclohexyl, cycloheptyl, cyclooctyl, norbornyl, bicyclo[2.2.1.]heptan-2-one, decalin, adamantyl and the like. Exemplary cylcoalkyl groups containing one or two double bonds include cyclobutenyl, cyclopentenyl, cyclohexenyl, cycloheptenyl, cyclooctenyl, pentadienyl, hexadienyl, heptadienyl and octadienyl, among others. Unless stated otherwise specifically in the specification, the cycloalkyl groups defined above may be optionally substituted by 1, 2, or 3 optional substituents.

Useful (cycloalkyl)alkyl groups of are selected from the alkyl groups defined above substituted by one or more cycloalkyl groups as defined above.

Useful alkenyl groups are selected from $C_{2-4}$ alkenyl groups. In one embodiment, useful alkenyl groups are $C_{2-4}$ alkenyl groups. Typical $C_{2-4}$ alkenyl groups include ethenyl, propenyl, isopropenyl, butenyl, sec-butenyl, pentenyl, and hexenyl. Typical $C_{2-4}$ alkenyl groups include ethenyl, propenyl, isopropenyl, butenyl, and sec-butenyl. Unless stated otherwise specifically in the specification, the alkenyl groups defined above may be optionally substituted by 1, 2, or 3 optional substituents.

Useful alkynyl groups are selected from $C_{2-6}$ alkynyl groups, preferably $C_{2-4}$ alkynyl. Typical $C_{2-6}$ alkynyl groups include ethynyl, propynyl, butynyl, 2-butynyl, pentynyl, and hexynyl groups. Typical $C_{2-4}$ alkynyl groups include ethynyl, propynyl, butynyl, and 2-butynyl groups. Unless stated otherwise specifically in the specification, the alkynyl groups defined above may be optionally substituted by 1, 2, or 3 optional substituents.

Useful haloalkyl groups include any of the above-mentioned $C_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, chloromethyl, dichloromethyl, and trichloromethyl groups).

Useful hydroxyalkyl groups include any of the above-mentioned $C_{1-10}$ alkyl groups substituted by one or more hydroxy groups, such as monohydroxyalkyl and dihydroxyalkyl groups (e.g., hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl).

Useful alkoxy groups include oxygen substituted by an unsubstituted or optionally substituted $C_{1-10}$ alkyl group (e.g., methoxy, ethoxy, propoxy, iso-propoxy, butoxy, tert-butoxy, iso-butoxy, sec-butoxy, and pentyloxy, hexyloxy, heptyloxy, petyloxy, nonyloxy and decyloxy).

Useful aryloxy groups include oxygen substituted by an unsubstituted or optionally substituted aryl group (e.g., phenoxy and 4-fluorophenoxy).

Useful aralkyloxy groups include oxygen substituted by an aralkyl group (e.g., benzyloxy).

Useful alkoxyalkyl groups include any of the above-mentioned $C_{1-10}$ alkyl groups substituted with any of the above-mentioned alkoxy groups (e.g., methoxymethyl, methoxyethyl, methoxypropyl, methoxybutyl, ethoxymethyl, ethoxyethyl, ethoxypropyl, ethoxybutyl, propoxymethyl, isopropoxymethyl, propoxyethyl, propoxypropyl, butoxymethyl, tert-butoxymethyl, isobutoxymethyl, sec-butoxymethyl, and pentyloxymethyl).

Useful haloalkoxy groups include oxygen substituted by one of the $C_{1-10}$ haloalkyl groups mentioned above (e.g., fluoromethoxy, difluoromethoxy, trifluoromethoxy, chloromethoxy, dichloromethoxy, trichloromethoxy and 2,2,2-trifluoroethoxy).

Useful alkylthio groups include sulfur substituted by an optionally substituted $C_{1-10}$ alkyl group Useful aryl groups are $C_{6-14}$ aryl, especially $C_{6-10}$ aryl. Typical $C_{6-14}$ or $C_{6-10}$ aryls aryl groups include phenyl, naphthyl, phenanthryl, anthracyl, indenyl, azulenyl, biphenyl, biphenylenyl, and fluorenyl groups, more preferably phenyl, naphthyl, and biphenyl groups. Unless stated otherwise specifically in the specification, the aryl groups defined above may be optionally substituted by 1, 2, or 3 optional substituents.

The term "heteroaryl" or "heteroaromatic" as employed herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, 3-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, heteroaryl groups include thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). Unless stated otherwise specifically in the specification, the heteroaryl groups defined above may be optionally substituted by 1, 2, or 3 optional substituents.

The terms "heterocyclic" and "heterocyclo" are used herein to mean saturated or partially unsaturated 3-7 membered or a 4-8 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. The heterocyclic ring may be attached to its pendant group at any carbon or any hetereoatom that results in a stable group. Examples include, but are not limited to, pyrrolidinyl, piperidinyl, piperazinyl, morpholinyl, imidazolinyl, pyrazolidinyl, tetrahydrofuranyl, oxazolidinyl, 2-oxooxazolidinyl, tetrahydrothienyl, imidazolidinyl, hexahydropyrimidinyl, benzo[b][1.4]oxazine, tetrahydroisoquinoline, benzodiazepines, and the like. Unless stated otherwise specifically in the specification, the heterocyclic groups defined above may be optionally substituted by 1, 2, or 3 optional substituents.

The term "(heteroaryl)alkyl" refers to an alkyl group as defined above which is substituted by one or more heteroaryl groups as defined above.

As used herein, the term "amino" or "amino group" refers to $—NH_2$.

Useful aminoalkyl groups include any of the above-mentioned $C_{1-10}$ alkyl groups substituted with an amino group.

Useful diaminoalkyl groups include any of the above-mentioned $C_{1-10}$ alkyl groups substituted with two amino groups.

Useful alkylamino and dialkylamino groups are $—NHR^{30}$ and $—NR^{30}R^{31}$, respectively, wherein $R^{30}$ and $R^{31}$ are each independently a $C_{1-10}$ alkyl group.

Useful hydroxyalkylamino groups are —NHR$^{32}$, wherein R$^{32}$ is any of the above-mentioned hydroxyalkyl groups.

Useful alkylaminoalkyl and dialkylaminoalkyl groups are any of the above-mentioned C$_{1-10}$ alkyl groups substituted by any of the above-mentioned alkylamino and dialkylamino groups, respectively.

As used herein, the term "aminocarbonyl" refers to —C(=O)NH$_2$.

As used herein, the term "carboxamido" refers to a radical of formula —C(=O)NR$^{33}$R$^{34}$, wherein R$^{33}$ and R$^{34}$ are each independently hydrogen, optionally substituted C$_{1-10}$ alkyl, or optionally substituted aryl. Exemplary carboxamido groups include —CONH$_2$, —CON(H)CH$_3$, —CON(CH$_3$)$_2$, and —CON(H)Ph and the like As used herein, the term "sulfonamido" refers to a radical of formula —SO$_2$NR$^{33}$R$^{34}$, wherein R$^{33}$ and R$^{34}$ are each independently hydrogen, optionally substituted C$_{1-10}$ alkyl, or optionally substituted aryl. Exemplary sulfonamido groups include —SO$_2$NH$_2$, —SO$_2$N(H)CH$_3$, —SO$_2$N(H)Ph and the like.

As used herein, the term "alkylsulfonyl" refers to a radical of formula —SO$_2$R$^{35}$, wherein R$^{35}$ is optionally substituted C$_{1-10}$ alkyl. Exemplary alkylsulfonyl groups include —SO$_2$Me, —SO$_2$Et, —SO$_2{}^t$Bu and the like Useful alkylcarbonyl groups include a carbonyl group, i.e., —C(=O)—, substituted by any of the above-mentioned C$_{1-10}$ alkyl groups or haloalkyl groups.

Useful alkylcarbonylamino groups include any of the above-mentioned alkylcarbonyl groups attached to an amino nitrogen, such as methylcarbonylamino.

Useful mercaptoalkyl groups include any of the above-mentioned C$_{1-10}$ alkyl groups substituted by a —SH group.

As used herein, the term "carboxy" refers to —COOH.

Useful carboxyalkyl groups include any of the above-mentioned C$_{1-10}$ alkyl groups substituted by —COOH.

As used herein, the term "ureido" refers to —NH—C(=O)—NH$_2$.

As used herein, the term "azido" refers to —N$_3$.

As used herein, the term "optionally substituted" refers to a group that may be unsubstituted or substituted.

Useful aralkyl groups include any of the above mentioned C$_{1-10}$ alkyl groups substituted with one, two, or three unsubstituted or optionally substituted aryl groups. Typically, "aralkyl" groups or "arylalkyl" groups of the present invention are substituted with one unsubstituted or optionally substituted aryl group. Non-limiting exemplary aralkyl groups include benzyl and phenethyl.

Optional substituents on optionally substituted groups, when not otherwise indicated, include one or more groups, typically 1, 2, or 3 groups, independently selected from the group consisting of halo, halo(C$_{1-6}$)alkyl, aryl, heterocyclo, cycloalkyl, C$_{1-6}$ alkyl, C$_{2-6}$ alkenyl, C$_{2-6}$ alkynyl, aryl(C$_{1-6}$) alkyl, aryl(C$_{2-6}$)alkenyl, aryl(C$_{2-6}$)alkynyl, cycloalkyl(C$_{1-6}$) alkyl, heterocyclo(C$_{1-6}$)alkyl, hydroxy(C$_{1-6}$)alkyl, amino (C$_{1-6}$)alkyl, carboxy(C$_{1-6}$)alkyl, alkoxy(C$_{1-6}$)alkyl, nitro, amino, ureido, cyano, alkylcarbonylamino, hydroxy, thiol, alkylcarbonyloxy, azido, alkoxy, alkylthio, haloalkoxy, aryloxy, aralkyloxy, carboxy, carboxamido, sulfonamido, alkylsulfonyl, heteroaryl, alkylcarbonyl, aminocarbonyl, and mercapto(C$_{1-6}$)alkyl groups mentioned above. In one embodiment, optional substituents include halo, halo(C$_{1-6}$) alkyl, hydroxy(C$_{1-6}$)alkyl, amino(C$_{1-6}$)alkyl, hydroxy, nitro, C$_{1-6}$ alkyl, alkoxy, haloalkoxy, and amino.

The invention disclosed herein is also meant to encompass prodrugs of any of the disclosed compounds. As used herein, prodrugs are considered to be any covalently bonded carriers that release the active parent drug in vivo. In general, such prodrugs will be a functional derivative of a compound of Formula I-XIII which is readily convertible in vivo, e.g., by being metabolized, into the required compound of Formula I-XIII. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984). Non-limiting examples of prodrugs include esters or amides of compounds of any of Formulae I-XIII having hydroxyalkyl or aminoalkyl as a substituent, and these may be prepared by reacting such parent compounds with anhydrides such as succinic anhydride.

The invention disclosed herein is also intended to encompass any of the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, and preferably $^3$H, $^{11}$C, and $^{14}$C. Isotopically-labeled compounds of the present invention can be prepared by methods known in the art.

The present invention is also directed specifically to $^3$H, $^{11}$C, or $^{14}$C radiolabeled compounds of any of Formulae I-XIII, as well as their pharmaceutically acceptable salts, prodrugs and solvates, and the use of any such compounds as radioligands for their binding site on the sodium channel. For example, one use of the labeled compounds of the present invention is the characterization of specific receptor binding. Another use of a labeled compound of the present invention is an alternative to animal testing for the evaluation of structure-activity relationships. For example, the receptor assay may be performed at a fixed concentration of a labeled compound of the invention and at increasing concentrations of a test compound in a competition assay. For example, a tritiated compound of any of Formulae I-XIII can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

Some of the compounds disclosed herein may contain one or more asymmetric centers and may thus give rise to enantiomers, diastereomers, and other stereoisomeric forms. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" is meant to encompass administering to a subject a compound of the present invention for the purposes of amelioration or cure, including preemptive and palliative treatment.

The term "about," as used herein in connection with a measured quantity, refers to the normal variations in that measured quantity, as expected by the skilled artisan making the measurement and exercising a level of care commensurate with the objective of measurement and the precision of the measuring equipment.

The invention disclosed herein also encompasses the use of salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of any of the disclosed compounds. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of any of Formulae I-XIII may be present as solvated forms with a pharmaceutically acceptable solvent, such as water, methanol, ethanol, and the like, and it is intended that the invention includes both solvated and unsolvated forms of compounds of any of Formulae I-XIII. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem. Commun.:* 603-604 (2001). A typical, non-limiting, process of preparing a solvate would involve dissolving a compound of any of Formulae I-XIII in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since compounds of Formulae I-XIII are blockers of sodium ($Na^+$) channels, a number of diseases and conditions mediated by sodium ion influx can be treated by employing these compounds. The present invention is thus directed generally to a method for treating a disorder responsive to the blockade of sodium channels in an animal suffering from, or at risk of suffering from, said disorder, said method comprising administering to the animal an effective amount of a compound represented by any of defined Formulae I-XIII, or a pharmaceutically acceptable salt, prodrug, or solvate thereof.

The present invention is further directed to a method of modulating sodium channels in an animal in need thereof, said method comprising administering to the animal at least one compound represented by any of defined Formulae I-XIII, or a pharmaceutically acceptable salt, prodrug, or solvate thereof.

More specifically, the present invention provides a method of treating stroke, neuronal damage resulting from head trauma, epilepsy, neuronal loss following global and focal ischemia, pain (e.g., acute pain, chronic pain, which includes but is not limited to neuropathic pain, postoperative pain, and inflammatory pain, or surgical pain), a neurodegenerative disorder (e.g., Alzheimer's disease, amyotrophic lateral sclerosis (ALS), or Parkinson's disease), migraine, manic depression, tinnitus, myotonia, a movement disorder, or cardiac arrhythmia, or providing local anesthesia. In one embodiment, the invention provides a method of treating pain. In another embodiment, the type of pain treated is chronic pain. In another embodiment, the type of pain treated is neuropathic pain. In another embodiment, the type of pain treated in postoperative pain. In another embodiment, the type of pain treated is inflammatory pain. In another embodiment, the type of pain treated is surgical pain. In another embodiment, the type of pain treated is acute pain. In another embodiment, the treatment of pain (e.g., chronic pain, such as neuropathic pain, postoperative pain, or inflammatory pain, acute pain or surgical pain) is preemptive. In another embodiment, the treatment of pain is palliative. In each instance, such method of treatment requires administering to an animal in need of such treatment an amount of a compound of the present invention that is therapeutically effective in achieving said treatment. In one embodiment, the amount of such compound is the amount that is effective as to block sodium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain, In: Textbook of Pain*, Wall and Melzack eds., $3^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed to the use of a compound represented by any of defined Formulae I-XIII, or a pharmaceutically acceptable salt, prodrug, or solvate thereof, in the manufacture of a medicament for treating a disorder responsive to the blockade of sodium channels (e.g., any of the disorders listed above) in an animal suffering from said disorder.

Furthermore, the present invention is directed to a method of modulating sodium channels in an animal in need thereof, said method comprising administering to the animal at least one compound represented by any defined Formulae I-XIII, or a pharmaceutically acceptable salt, prodrug, or solvate thereof.

The present invention is also directed to the use of a compound represented by any of defined Formulae I-XIII, or a pharmaceutically acceptable salt, prodrug, or solvate thereof, in the manufacture of a medicament, in particular a medicament for modulating sodium channels, in an animal in need thereof.

General Synthesis of Compounds

The compounds of the present invention are prepared using methods known to those skilled in the art in view of this disclosure. Carboxylic acid intermediate J is prepared as described in Scheme 1. Briefly, phenol A is made to react with 4-fluoronitrobenzene B to give phenoxyphenyl C. The nitro group of C is reduced to give aniline D. Conversion of aniline D to iodide E followed by coupling with pinacol borane gives boranate F. Coupling of F with bromopyridine G gives the pyridine ester H. Saponification of H gives J. In Schemes 2-7, J is made to react with the appropriate amine to give a compound of Formula VIII wherein G is G-1, G-2, G-3, G-4, G-5, or G-6, respectively, i.e., compounds of Formulae VIII-1 to VIII-6. Suitable coupling agents for use in Schemes 2-7 include, e.g., HOBt/EDC, DCC, HATU. Suitable solvents include, e.g., dichloromethane, DMF. Additional coupling agent/solvent combinations are well known to those of ordinary skill in the art. Likewise, compounds of Formula I wherein G is G-1, G-2, G-3, G-4, G-5, or G-6 can be prepared starting from carboxylic acid K to give compounds of Formulae I-1 to I-6 as shown in Scheme 8. Additional examples of synthesis are described and illustrated in the working examples set forth below.

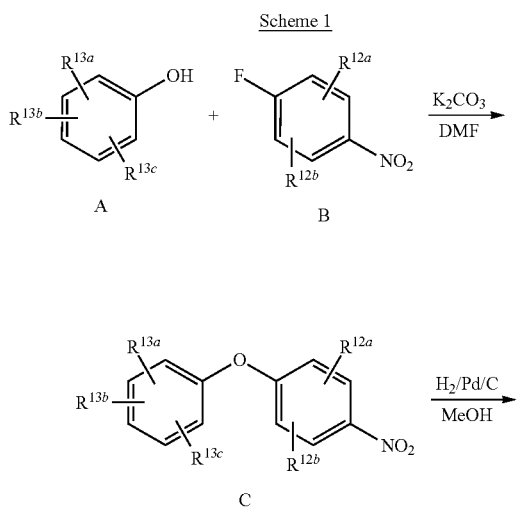

-continued
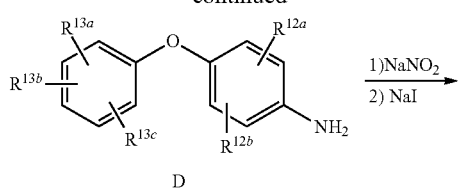
D
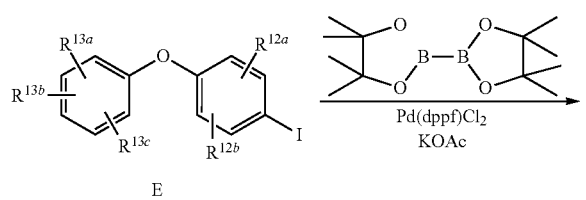
E
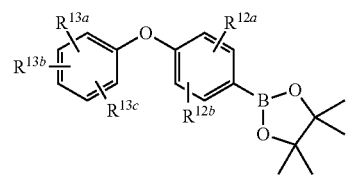
F
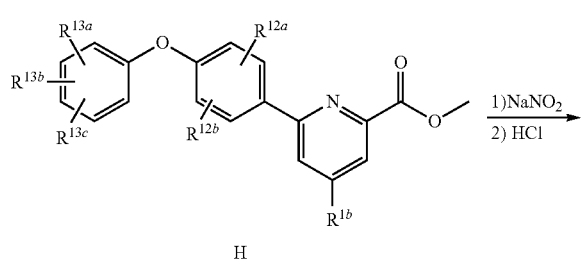
H
-continued
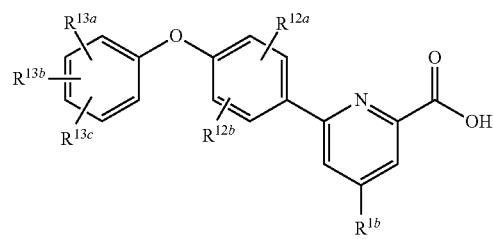
J
Scheme 2
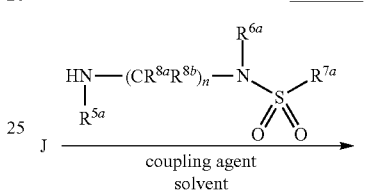
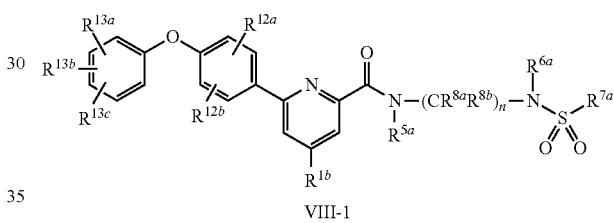
VIII-1
Scheme 3
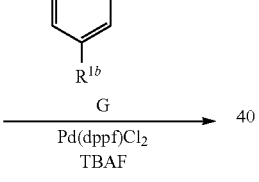
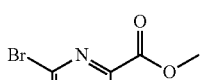
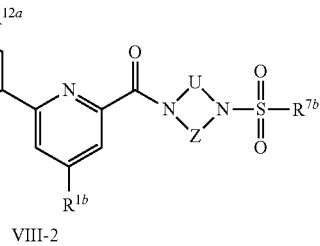
VIII-2

Scheme 4
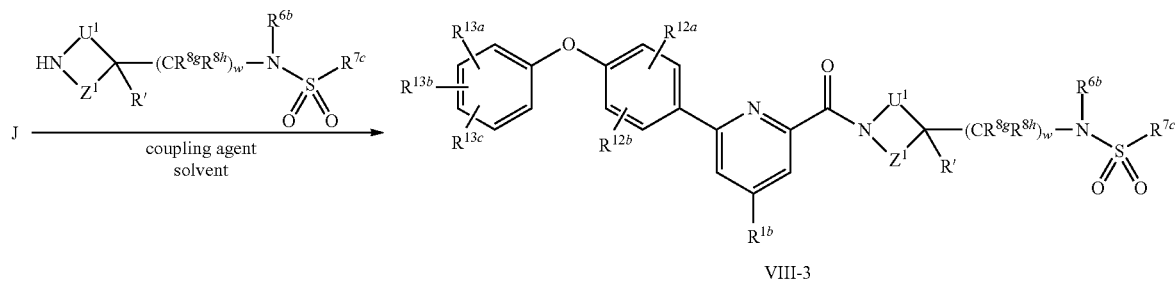
VIII-3
Scheme 5
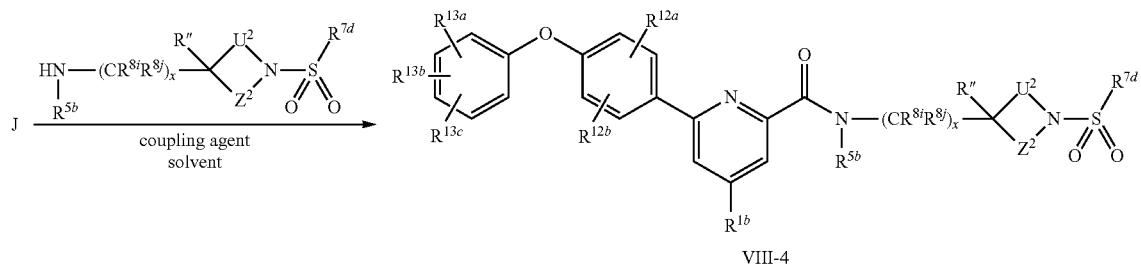
VIII-4
Scheme 6
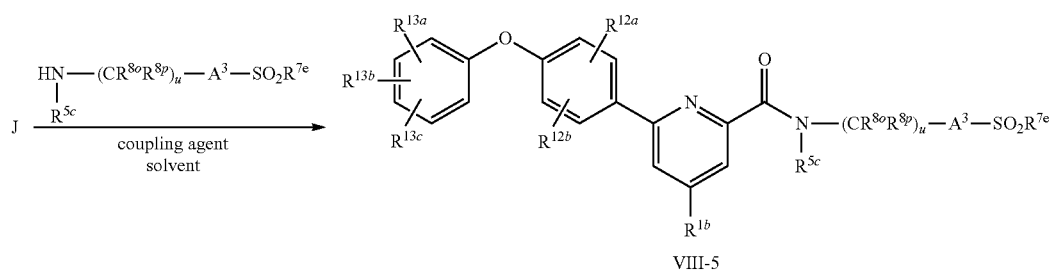
VIII-5
Scheme 7
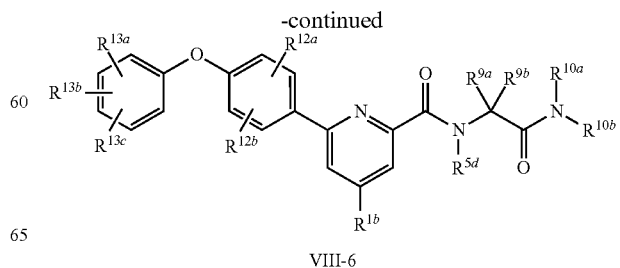
VIII-6

Scheme 8

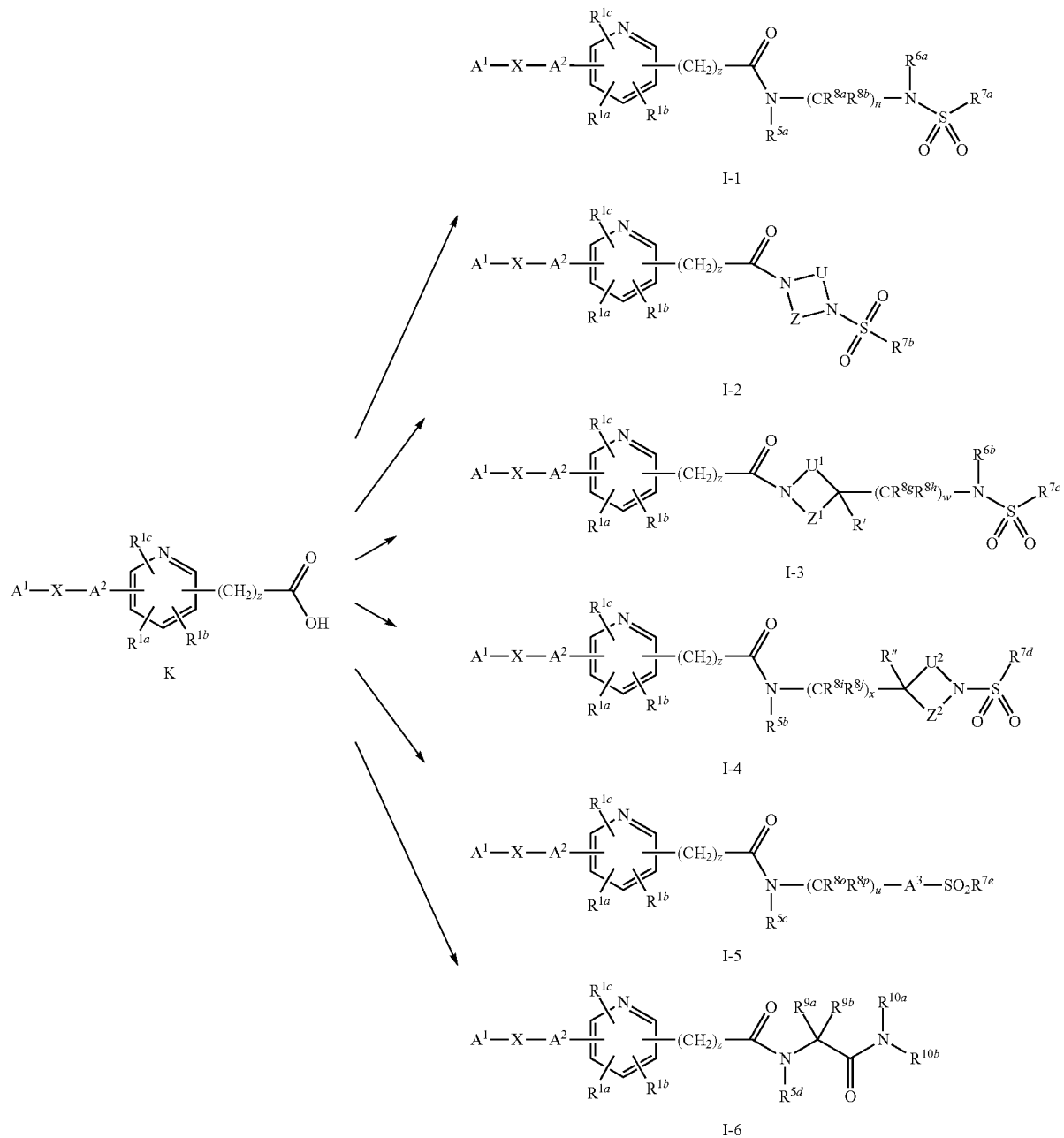

Testing of Compounds

Compounds of the present invention were assessed by sodium mobilization and/or electrophysiological assays for sodium channel blocker activity. One aspect of the present invention is based on the use of the compounds herein described as sodium channel blockers. Based upon this property, compounds of the invention are considered useful in treating a condition or disorder responsive to the blockade of sodium ion channels, e.g., stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, distonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, cardiac arrhythmia, or providing local anesthesia. The compounds of the present invention are also expected to be effective in treating pain, e.g., acute pain, chronic pain, which includes but is not limited to, neuropathic pain, postoperative pain, and inflammatory pain, or surgical pain.

More specifically, the present invention is directed to compounds of Formulae I-XIII that are blockers of sodium channels. According to the present invention, those compounds having useful sodium channel blocking properties exhibit an $IC_{50}$ for $Na_v1.1$, $Na_v1.2$, $Na_v1.3$, $Na_v1.4$, $Na_v1.5$, $Na_v1.6$, $Na_v1.7$, $Na_v1.8$, and/or $Na_v1.9$ of about 100 µM or less, e.g., about 50 µM or less, about 10 µM or less, about 5 µM or less, or about 1 µM or less, in sodium mobilization and/or electrophysiological assays. In certain embodiments, compounds of the present invention exhibit an $IC_{50}$ for $Na_v1.7$ of 100 µM or less, about 50 µM or less, about 10 µM or less, about 5 µM or less, about 1 µM or less, about 0.5 µM or less, or about 0.1 µM or less. Compounds of the present invention can be tested for their $Na^+$ channel blocking activity using methods well known in the art and by the following fluorescence imaging and electrophysiological in vitro assays and/or in vivo assays.

In Vitro Assay Protocob

FLIPR® Assays

Recombinant $Na_v1.7$ Cell Line:

In vitro assays were performed in a recombinant cell line expressing cDNA encoding the alpha subunit ($Na_v1.7$, SCN9a, PN1, NE) of human $Na_v1.7$ (Accession No. NM_002977). The cell line was provided by investigators at Yale University (Cummins et al, *J. Neurosci.* 18(23): 9607-9619 (1998)). For dominant selection of the $Na_v1.7$-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-Recombinant Cell Lines Expressing Native $Na_v1.7$:

Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$, from various species, or in cultures of fresh or preserved sensory neurons, such as dorsal root ganglion (DRG) cells, isolated from various species. Primary screens or counter-screens of other voltage-gated sodium channels to can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., *Br. J. Pharmacol.* 144:801-812 (2005)). Pharmacological profiling for these counter-screens is carried out under conditions similar to the primary or alternative $Na_v1.7$ assays described below.

Cell Maintenance:

Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 µg/mL streptomycin, 2-4 mM L-glutamine, and 500 mg/mL G418. For natural, non-recombinant cell lines, the selective antibiotic was omitted, and additional media formulations can be applied as needed.

Assay Buffer:

The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO4$ and 0.556 mM D-glucose (Hanks et al., *Proc. Soc. Exp. Biol. Med.* 71:196 (1949)), and the simple formulation was typically the basic buffer throughout the assay (i.e., all wash and addition steps).

CoroNa™ Green AM $Na^+$ Dye for Primary Fluorescence Assay:

The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., *J. Biol. Chem.* 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of dye in the cell loading buffer was 5 µM.

Membrane Potential Dye for Alternative Fluorescence Assays: A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot dissolved in assay buffer to form a 20×-concentrated stock solution that can be used for several weeks.

Agonists:

In the fluorescence assays, two agonists were used in combination, namely 1) veratridine; and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 µM (veratridine) and 10 µg/mL (scorpion venom). Both of the agonists were purchased from Sigma Aldrich, St. Louis, Mo.

Test Compounds:

Test compounds were dissolved in DMSO to yield 10 mM stock solutions. The stock solutions were further diluted using DMSO in 1:3 serial dilution steps with 10 points (10,000 µM, 3,333 µM, 1,111 µM, 370 µM, 123 µM, 41 µM, 14 µM, 4.6 µM, 1.5 µM and 0.5 µM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 µM, 6.7 µM, 2.2 µM, 0.74 µM, 0.25 µM and 0.08 µM, 0.03 µM, 0.01 µM, 0.003 µM and 0.001 µM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis:

The data were analyzed according to methods known to those skilled in the art or using the GraphPad® Prism 4.0 Program (available from GraphPad Software, San Diego, Calif.) to determine the $IC_{50}$ value for the test article. At least one standard reference compound was evaluated during each experiment.

FLIPR® or FLIPR$^{TETRA}$® Sodium Dye Assay with KCl and Test Article Pre-Incubation:

Cells were prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 µl/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) First, the compound dilutions and controls were added as 4× concentrates in assay buffer at 50 µL/well; 2) CoroNa™ Green AM dye was diluted from the stock solution to 20 µM in assay buffer (4× concentrate) and added to the plate at 50 µL/well; and 3) Finally, a solution of 180 mM KCl (2×) was prepared by diluting a 2M stock solution into assay buffer and the solution was added to the cells at 100 µl/well. The cells were incubated at 25° C. in the dark for 30 min. before their fluorescence was measured.

The plates containing dye-loaded cells were then flicked to remove the pre-incubation components and washed once with 100 µL/well assay buffer. A 100 µL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.) Samples were excited by either a laser or a PMT light source (Excitation wavelength=470-495 nM) and the emissions are filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of $Na^+$ ions to the CoroNa™ Green dye, was captured for ~180 sec. thereafter. Results were expressed in relative fluorescence units (RFU) and can be determined by using the maximum signal during the latter part of the stimulation; or the maximum minus the minimum during the whole agonist stimulation period; or by taking the area under the curve for the whole stimulation period.

The assay can be performed as a screening assay as well with the test articles present in standard amounts (e.g., 10 µM) in only one or two wells of a multi-well plate during the primary screen. Hits in this screen were typically profiled more exhaustively (multiple times), subjected to dose-response or competition assays and tested in counter screens against other voltage-gate sodium channels or other biologically relevant target molecules.

FLIPR® or FLIPR$^{TETRA}$® Membrane Potential Assay with KCl and Test Article Pre-Incubation:

Cells are prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay (see, e.g., Benjamin et. al., *J. Biomol. Screen* 10(4):365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 µL/Uwell assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) First, the compound dilutions and controls are added as 4× concentrates in assay buffer at 50 µL/well; 2) Membrane potential dye is diluted from the stock solution in assay buffer (4× concentrate) and added to the plate at 50 µL/well; and 3) Finally, a solution of 180 mM KCl (2×) are prepared by diluting a 2M stock solution into assay buffer and the solution added to the cells at 100 µL/Uwell. The cells are incubated at 37° C. in the dark for 30-60 min. before their fluorescence is measured.

The plates containing dye-loaded cells are then flicked to remove the pre-incubation components and washed once with 50 µL/well assay buffer. A 50 µL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay Without KCl and Test Article Pre-Incubation:

Cells are prepared by plating the recombinant HEK293 cells or other host cells expressing either recombinant or non-recombinant, native, Na$_v$1.7 alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% CO$_2$, 95% humidity, in preparation for the assay. For counter-screens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 µL/well assay buffer (1× Hank's balanced salt solution without sodium bicarbonate or phenol red, 20 mM Hepes, pH 7.3). Membrane potential dye is then added to each well of the 96-well plate (50 µL/well), from a freshly diluted sample of the stock (now at 4× concentration) in the assay buffer. The cells are incubated at 37° C. in the dark for 30-60 min. before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 µL/well from a 4× stock plate) and then the channel activators (later, 100 µL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g. 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells:

The hNa$_v$1.7 expressing HEK-293 cells were plated on 35 mm culture dishes pre-coated with poly-D-lysine in standard DMEM culture media (Mediatech, Inc., Herndon, Va.) and incubated in a 5% CO$_2$ incubator at 37° C. Cultured cells were used approximately 12-48 hours after plating.

Electrophysiology:

On the day of experimentation, the 35 mm dish was placed on the stage of an inverted microscope equipped with a perfusion system that continuously perfuses the culture dish with fresh recording media. A gravity driven superfusion system was used to apply test solutions directly to the cell under evaluation. This system consists of an array of glass pipette glass connected to a motorized horizontal translator. The outlet of the shooter was positioned approximately 100 µm from the cell of interest.

Whole cell currents were recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals were formed and the whole-cell configuration was established in voltage clamp mode, and membrane currents generated by hNa$_v$1.7 were recorded in gap-free mode. Borosilicate glass pipettes have resistance values between 1.5 and 2.0 MD when filled with pipette solution and series resistance (<5 MΩ) was compensated 75-80%. Signals were sampled at 50 kHz and low pass filtered at 3 kHz.

The voltage clamp protocol to examine hNa$_v$1.7 currents was as follows. First, the standard current-voltage relationship was tested by pulsing the cell from the holding voltage ($V_h$) of −120 mV by a series of 5 msec long square-shaped test pulses incrementing in +10 mV steps over the membrane voltage range of −90 mV to +60 mV at the pace of stimulation of 0.5 Hz. This procedure determines the voltage that elicits the maximal current ($V_{max}$). Second, $V_h$ was re-set to −120 mV and a steady-state inactivation (SSIN) curve was taken by the standard double-pulse protocol: 100 ms depolarizing prepulse was incremented in steps of +10 mV (voltage range from −90 mV to 0 mV) immediately followed by the 5 ms long test pulse to −10 mV at the pace of stimulation of 0.2 Hz. This procedure determines the voltage of full inactivation ($V_{full}$). Third, the cell was repeatedly stimulated with the following protocol, first in the absence of the test compound then in its presence. The protocol consisted of depolarizing the cell from the holding potential of −120 mV to the Vu value for 4.5 seconds then repolarizing the cell to the holding potential for 10 ms before applying the test pulse to the $V_{max}$ for 5 ms. The amount of inhibition produced by the test compound was determined by comparing the current amplitude elicited by the test pulse in the absence and presence of the compound.

Solutions and Chemicals:

For electrophysiological recordings the external solution was either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), $CaCl_2$ (1), $MgCl_2$ (5), EGTA (11), HEPES (10: pH 7.4, 305 mOsm). Compounds were prepared first as series of stock solutions in DMSO and then dissolved in external solution; DMSO content in final dilutions did not exceed 0.3%. At this concentration, DMSO did not affect sodium currents. Vehicle solution used to establish base line was also contacting 0.3% DMSO.

Data Analysis:

Data was analyzed off-line using Clampfit software (pClamp, v. 8; Axon Instruments) and graphed using Graph-Pad Prizm (v. 4.0) software.

In Vivo Assay for Pain

The compounds can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

In Vivo Assays for Inflammatory or Neuropathic Pain

Test Animals:

Each experiment uses rats weighing between 200-260 g at the start of the experiment. The rats are group-housed and have free access to food and water at all times, except prior to oral administration of a test compound when food is removed for 16 hours before dosing. A control group acts as a comparison to rats treated with a compound of Formulae I-XIII. The control group is administered the carrier as used for the test compound. The volume of carrier administered to the control group is the same as the volume of carrier and test compound administered to the test group.

Inflammatory Pain:

To assess the actions of the compounds of Formulae I-XIII on the treatment of inflammatory pain the Freund's complete adjuvant ("FCA") model of inflammatory pain was used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). The left hind paw of each animal was administered a 50 μL intraplantar injection of 50% FCA. 24 hour post injection, the animal was assessed for response to noxious mechanical stimuli by determining the paw withdrawal threshold (PWT), or to noxious thermal stimuli by determining the paw withdrawal latency (PWL), as described below. Rats were then administered either a test compound or 30 mg/kg of a positive control compound (indomethacin). Responses to noxious mechanical or thermal stimuli were determined 1, 3, and 5 hours post administration (admin). Percentage reversal of hyperalgesia for each animal is defined as:

$$\% \text{ reversal} = \frac{[(\text{post administation } PWT \text{ or } PWL) - (\text{pre-administration } PWT \text{ or } PWL)]}{[(\text{baseline } PWT \text{ or } PWL) - (\text{pre-administration } PWT \text{ or } PWL)]} \times 100$$

Compound 47 induced a statistically significant increase in PWT at 10 mg/kg (3 h) and 30 mg/kg (1, 3 and 5 h) following oral (PO) administration.

Neuropathic Pain:

To assess the actions of the test compounds for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., *Pain* 43:205-218 (1990)). Partial ligation of the left sciatic nerve is performed under isoflurane/$O_2$ inhalation anaesthesia. Following induction of anaesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anaesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ reversal} = \frac{[(\text{post administation } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery animals are weighed, administered a subcutaneous (s.c.) injection of saline or ringers lactate, the wound area is dusted with antibiotic powder and they are kept on a warm pad until they recover from the anaesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a compound of Formulae I-XIII for the left rear paw of the animal. The animals can also be assessed for response to noxious thermal stimuli or for tactile allodynia, as described below. The Chung model for neuropathic pain is described in Kim et al., *Pain* 50(3):355-363 (1992).

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

In Vivo Assay for Anticonvulsant Activity

The compounds of the present invention of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present invention include all compositions where a compound of the present invention is combined with a pharmaceutically acceptable carrier. In one embodiment, the compound is present in the composition in an amount that is effective to achieve its intended therapeutic purpose. While individual needs may vary, a determination of optimal ranges of effective amounts of each compound is within the skill of the art. Typically, the compounds may be administered to a mammal, e.g., a human, orally at a dose of from about 0.0025 to about 1500 mg per kg body weight of the mammal, or an equivalent amount of a pharmaceutically acceptable salt, prodrug, or solvate thereof, per day to treat, prevent or ameliorate the particular disorder. A useful oral dose of a compound of the present invention administered to a mammal is from about 0.0025 to about 50 mg per kg body weight of the mammal, or an equivalent amount of the pharmaceutically acceptable salt, prodrug, or solvate thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily, e.g., as one or more tablets or capsules, each containing from about 0.01 to about 50 mg of the compound, or an equivalent amount of a pharmaceutically acceptable salt, prodrug or solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal or transmucosal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

A method of the present invention, such as a method for treating a disorder responsive to the blockade of sodium channels in an animal in need thereof, can further comprise administering a second therapeutic agent to the animal in combination with a compound of the present invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

A compound of the present invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein. In one embodiment, a compound of the present invention is administered concurrently with a second therapeutic agent; for example, a single composition comprising both an effective amount of a compound of any of Formulae I-XIII, and an effective amount of the second therapeutic agent can be administered. Accordingly, the present invention further provides a pharmaceutical composition comprising a combination of a compound of the present invention, the second therapeutic agent, and a pharmaceutically acceptable carrier. Alternatively, a first pharmaceutical composition comprising an effective amount of a compound of any of Formulae I-XIII and a second pharmaceutical composition comprising an effective amount of the second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the second therapeutic agent is administered while the compound of the present invention exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal antiinflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol. II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocorine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor, phenol; pramoxine; capsaicin; tar, steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present invention is preferably manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

Synthesis of 1-fluoro-4-(4-nitrophenoxy)benzene (compound 1)

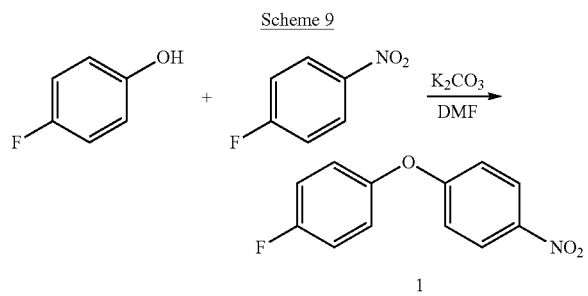

Scheme 9

Method A:

A 500 mL round bottom flask was charged with 4-fluorophenol (11.2 g, 0.1 mmol), 4-fluoro-4-nitrobenzene (14.1 g, 0.1 mol), $K_2CO_3$ (27.6 g, 0.2 mol) and DMF (50 mL). The reaction mixture was stirred vigorously at 120° C. for 4 h, cooled to room temperature, and then poured into 300 mL water. The resulting mixture was extracted with ethyl acetate. The combined organic layers were dried over $MgSO_4$ and concentrated to give compound 1 as an off-white solid which was used in the next step without further purification (23.3 g, 100% yield, (m/z+H)=234).

Method B:

A mixture of 4-fluorophenol (30 g, 0.27 mol), 1-fluoro-4-nitrobenzene (38 g, 0.27 mol) and $K_2CO_3$ (37.8 g, 0.27 mol) in DMF (300 mL) was heated at 95° C. overnight. The reaction mixture was cooled to room temperature and diluted with ethyl acetate (150 mL). The organic layer was washed with water. The organic layer was dried over anhydrous $MgSO_4$ and concentrated under reduced pressure to give an oily residue. The residue was purified by automated column chromatography on silica gel using a CombiFlash® system (5% EtOAc in Hexanes) to give compound 1 as brown crystals (44 g, 70% yield, $R_f$=0.7, eluent (30% diethyl ether in hexanes), $^1$H NMR (400 MHz, $CD_3Cl$): δ 8.2 (d, J=9.4 Hz, 2H), 7.04-7.17 (m, 4H), 6.99 (d, J=9.4, 2H)).

Example 2

Synthesis of 4-(4-fluorophenoxy)aniline (compound 2)

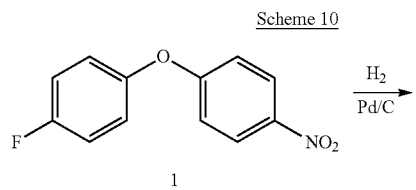

Scheme 10

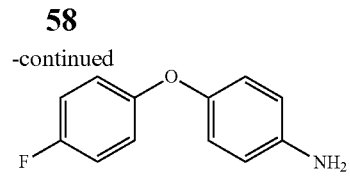

Method A:

Compound 1 (23.3 g, 0.1 mol) was dissolved in ca. 50 mL MeOH and to this solution two spatulas of palladium on carbon (5%) (ca. 50 mg) were added. The reaction mixture was purged with nitrogen and hydrogen (three times) and stirred overnight at room temperature under a balloon of hydrogen. The palladium on carbon was removed by filtration and the filtrate was concentrated by rotary evaporation to give compound 2 as an off-white solid (20.4 g, 100% yield, (m/z+H)=204).

Method B:

Compound 1 (10 g, 42.9 mmol) was dissolved in 10% ethyl acetate in methanol (250 mL) and 10% palladium on carbon (2.0 g) was added. The reaction mixture was stirred for 5.0 h at room temperature. After the reaction was complete, the mixture was filtered through a pad of celite. The filtrate was concentrated to give compound 2 as a reddish brown solid which was used in the next step without purification (8.5 g, 97% yield, $R_f$=0.2, eluent (25% ethyl acetate in hexanes).

Example 3

Synthesis of 1-fluoro-4-(4-iodophenoxy)benzene (compound 3)

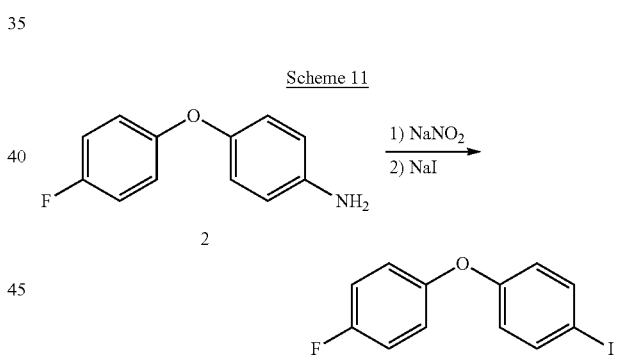

Scheme 11

Method A:

To a DME (272 mL) solution of compound 2 (20.4 g, 0.1 mol) was added a solution of $H_2SO_4$ (41 mL concentrated $H_2SO_4$ in 204 mL of $H_2O$) dropwise. The resulting mixture was cooled to 0° C. and a solution of $NaNO_2$ (10.3 g, 0.15 mol) in $H_2O$ (68 mL) was added over 20 minutes. After the addition was complete, the reaction mixture was stirred at 0° C.-5° C. for an additional 30 min and a solution of NaI (75 g, 0.5 mol) in $H_2O$ (204 mL) was added dropwise at 0° C. After the addition was complete, the mixture was stirred for and additional 30 minutes and diluted with EtOAc. The organic layer was collected and washed with an aqueous solution of $Na_2S_2O_3$ and brine and dried over $MgSO_4$. The solvent was removed by evaporation and the residue solidified instantly. The pale solid product (compound 3) was used in the next step without further purification (96% yield, (m/z+H)=315).

Method B:

To a solution of p-TsOH.H$_2$O (56.0 g, 300 mmol) in acetonitrile (500 mL), was added compound 2. The suspension was cooled to 0-5° C. and stirred for 15 min. A solution of NaNO$_2$ (13.8 g, 200 mmol) and KI (41.5 g, 250 mmol) in H$_2$O (150 mL) was added slowly thereto. During the addition, N$_2$ evolved. The reaction mixture was stirred for 1 h at room temperature. After the reaction was complete, saturated NaHCO$_3$ was added to adjust the pH to 9-10 and 2M Na$_2$S$_2$O$_3$ (6.0 mL) was added. The aqueous layer was separated and extracted with ethyl acetate. The combined organic layers were dried with anhydrous MgSO$_4$ and concentrated under reduced pressure. The crude product was purified by automated column chromatography on silica gel using a CombiFlash® system (10% ethyl acetate in hexanes) to give compound 3 as a pale brown crystal (19.3 g, 67% yield, R$_f$=0.8, eluent (25% ethyl acetate in hexanes), LC/MS: m/z=315 [M+H]$^+$)

Example 4

Synthesis of 2-(4-(4-fluorophenoxy)phenyl)-4,4,5,5-tetramethyl-1,3,2-dioxaborolane (compound 4)

Scheme 12

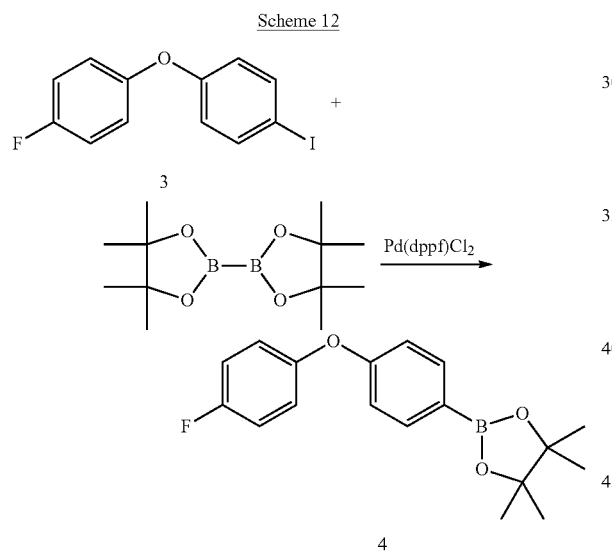

Method A:

A 100 mL round bottom flask was charged with compound 3 (Netchem, 5 g, 15.9 mmol), pinacol diborane (4.43 g, 17.4 mmol), KOAc (4.68 g, 47.7 mmol), pd(dppf)Cl$_2$ (402 mg, 0.49 mmol) and dioxane (60 mL). The reaction mixture was purged with argon and then stirred at 90° C. under argon for 20 h. The reaction mixture was cooled to room temperature, diluted with EtOAc, and dried over MgSO$_4$. The EtOAc was evaporated and the residue was purified by column chromatography on silica gel (hexanes/EtOAc) to give compound 4 as a white solid (2.5 g, 50% yield, (m/z+H)=315).

Method B:

To a suspension of compound 3 (10 g, 31.8 mmol) in dioxane (320 mL) was added Pd(dppf)Cl$_2$.CH$_2$Cl$_2$ (0.82 g, 1.0 mmol) and reaction mixture was degassed by repeating argon/vacuum cycles. The suspension was stirred for 10 min at room temperature, bis(pinacolato)diboron (8.9 g, 35.0 mmol) and potassium acetate (0.97 g, 95.4 mmol) were added, and the reaction mixture was heated at 90° C. for 18 h under argon. Upon cooling to room temperature, the mixture was filtered through a pad of celite and concentrated under reduced pressure. The residue was purified by automated column chromatography on silica gel using a CombiFlash® system (5% ethyl acetate in hexanes) to give compound 4 as a pale brown solid (9.0 g, 90% yield, R$_f$=0.4, eluent (10% ethyl acetate in hexanes), LC/MS: m/z-315 [M+H]$^+$, $^1$H NMR (400 MHz, CD$_3$Cl): δ 7.67 (d, J=8.6 Hz, 2H), 7.06-6.96 (m, 4H), 6.93 (d, J=8.6 Hz, 2H), 1.33 (s, 12H)).

Example 5

Synthesis of 6-(4-(4-fluorophenoxy)phenyl)picolinic acid (compound 5)

Scheme 13

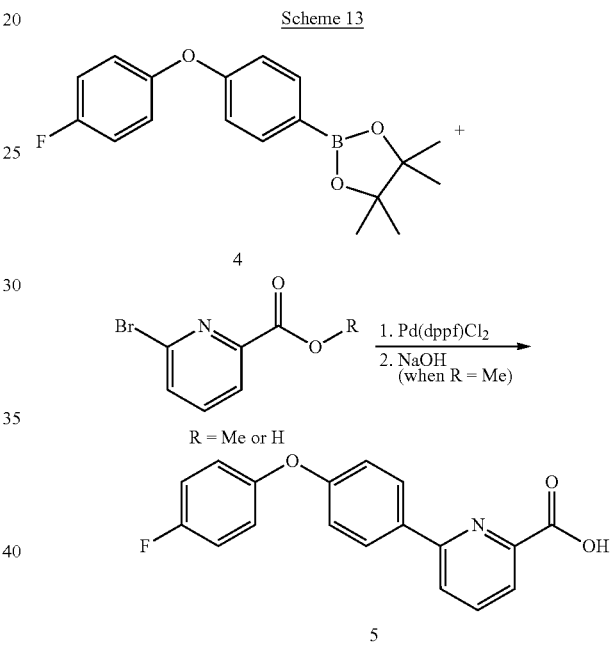

R = Me or H

Method A:

Step 1: A 100 mL round bottom flask was charged with compound 4 (3.14 g, 10 mmol), 6-bromopyridine-2-carboxylic acid methyl ester (Aldrich, 2.16 g, 10 mmol), Pd(dppf)Cl$_2$ (408 mg, 0.50 mmol) and a THF solution of TBAF (1N in THF). The mixture was purged with argon and then stirred at 60° C. under argon for 20 h. The reaction mixture was cooled to room temperature and diluted with EtOAc. The EtOAc was separated, dried over MgSO$_4$, filtered, and evaporated. The residue was purified by column chromatography on silica gel (hexanes/EtOAc) to give methyl 6-(4-(4-fluorophenoxy)phenyl)picolinate as a white solid (75% yield, (m/z+H)=324).

Step 2:

A 100 mL round bottom flask was charged with the pyridine methyl ester from Step 1 above (5.0 g, 15.47 mmol) and THF (20 mL). To this mixture, 10 mL of aqueous NaOH (1.85 g, 45 mmol) was added. The mixture was stirred at 60° C. for 1 h and then cooled with an ice bath. The pH of the reaction mixture was adjusted to 2 with 6N HCl and the precipitate was collected and dried to give compound 5 as a white solid (4.5 g, 95% yield, (m/z+H)=310).

Method B:

6-Bromopyridine-2-carboxylic acid (1.0 g, 4.95 mmol), compound 4 (1.15 g, 4.95 mmol) and anhydrous sodium carbonate (4.2 g, 39.6 mmol) were dissolved in a mixture of DMF/H$_2$O (60 mL). Tetrakis (triphenylphosphine) palladium (286 mg, 0.25 mmol) was added thereto and the reaction mixture was refluxed for 4 h. After the reaction was complete, the reaction mixture was cooled to room temperature and 1.0 N NaOH was added. The aqueous phase was washed with CHCl$_3$ then acidified with 6N HCl to pH 5. A white precipitate was collected, washed with water, and dried under vacuum. The crude product was recrystallized from EtOAc/hexane to give compound 5 as a white solid (1.3 g, 86% yield, LC/MS: m/z=310 [M+H]$^+$, $^1$H NMR (400 MHz, CD$_3$OD): δ8.04 (s, br, 2H), 7.8 s, br, 3H), 6.8-7.0 (m, 6H)).

Example 6

Synthesis of (6-(4-(4-fluorophenoxy)phenyl)pyridin-2-yl)(piperazin-1-yl)methanone (compound 6)

Scheme 14

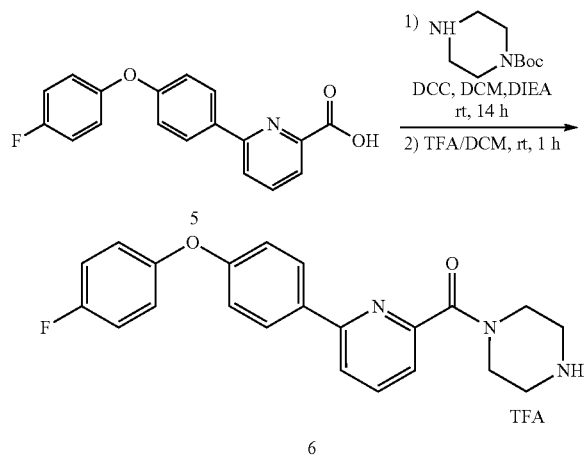

A 50 mL round bottom flask was charged with compound 5 (0.5 g, 1.6 mmol), 4-Boc-piperidine (Aldrich, 299 mg, 1.6 mmol), DCC (329 mg, 1.6 mmol), DIEA (0.33 mL, 1.6 mmol) and DCM (5 mL). The mixture was stirred at room temperature overnight, diluted with water, and extracted with EtOAc. The organic layer was separated and the solvent was removed by rotary evaporation. The residue was re-dissolved in 6 mL of DCM/TFA (1:1) and the resulting mixture was stirred at room temperature for 1 h. The solvent was removed by rotary evaporation and the residue was dried under vacuum to give compound 6 as a yellowish solid (0.7 g, 90% yield, (m/z+H)=379).

Example 7

Synthesis of (6-(4-(4-fluorophenoxy)phenyl)pyridin-2-yl)(4-((4-(trifluoromethoxy)phenyl)sulfonyl)piperazin-1-yl)methanone (compound 7)

Scheme 15

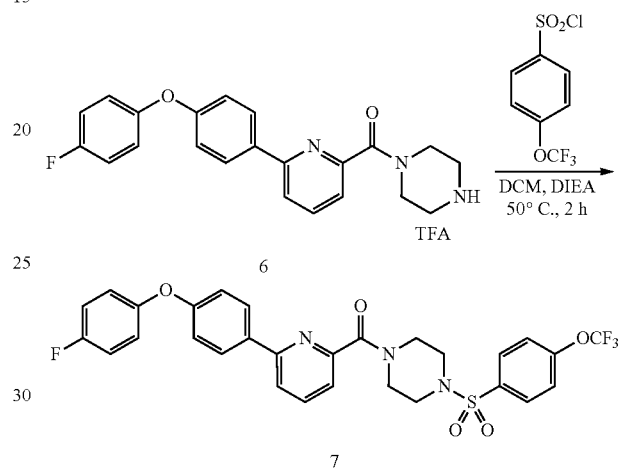

A 50 mL round bottom flask was charged with compound 6 (100 mg, 0.24 mmol), 4-trifluoromethoxy sulfonyl chloride (41 μL, 0.24 mmol), DIEA (0.1 mL, 0.7 mmol) and DCM (5 mL). The mixture stirred at 60° C. for 2 h, cooled to room temperature, and extracted with EtOAc. The organic layer was separated and the solvent was removed by evaporation. The residue was subjected to column chromatography on silica gel (hexanes/EtOAc) to give compound 7 as a white solid (120 mg, 83% yield, (m/z+H)=602, $^1$H NMR (CDCl$_3$) δ ppm: 6.80-8.90 (m, 15H); 3.8 (m, 4H); 3.20 (m, 4H)).

Example 8

Synthesis of (6-(4-(4-fluorophenoxy)phenyl)pyridin-2-yl)(4-((3-(methylsulfonyl)phenyl)sulfonyl)piperazin-1-yl)methanone (compound 8)

Scheme 16

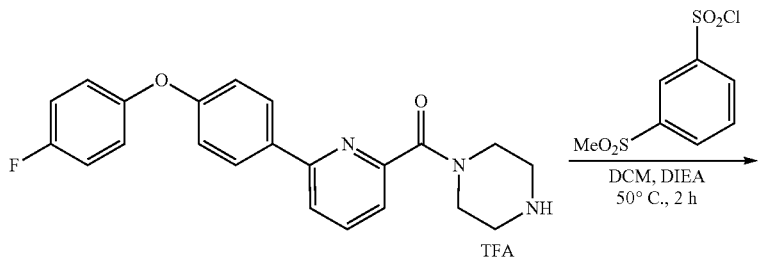

-continued

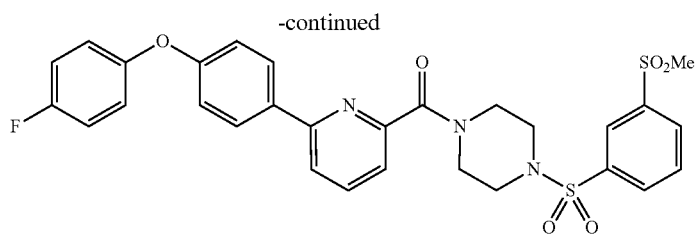

8

According to the methodology described in Example 7, compound 6 (100 mg, 0.24 mmol), 3-methylsulfonylbenzenesulfonyl chloride (60 mg, 0.24 mmol), DIEA (0.1 mL, 0.7 mmol) and DCM (5 mL) were reacted to give compound 8 in 84% yield (LC/MS (m/z+H)=596; $^1$H NMR (CDCl$_3$) δ ppm: 6.8-8.5 (m, 15H); 4.0 (m, 4H); 3.3 (m, 4H); 3.2 (s, 3H)).

The following compounds were prepared similarly:
2,2,2-trifluoro-1-(7-((4-(6-(4-(4-fluorophenoxy)phenyl) picolinoyl)piperazin-1-yl)sulfonyl)-3,4-dihydroisoquinolin-2(1H)-yl)ethanone (compound 9):

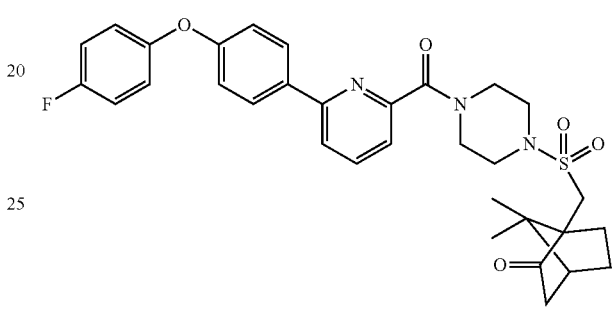

3-((4-(6(4-(4-fluorophenoxy)phenyl)picolinoyl)piprazin-1-yl)sulfonyl)benzonitrile (compound 10):

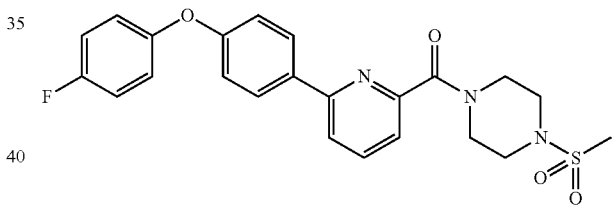

4-(6-(4-(4-fluorophenoxy)phenyl)picolinoyl)-N,N-dimethyl-piperazine-1-sulfonamide (compound 11):

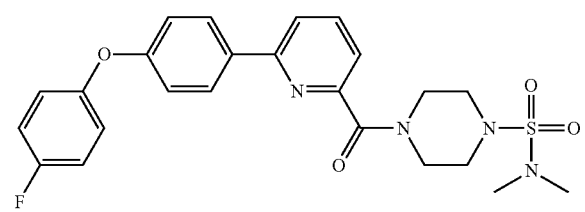 [SMILES: CN(C)S(=O)(=O)N1CCN(C(=O)c2cccc(-c3ccc(Oc4ccc(F)cc4)cc3)n2)CC1]

1-(((4-(6-(4-(4-fluorophenoxy)phenyl)picolinoyl)piperazin-1-yl)sulfonyl)methyl)-7,7-dimethylbicyclo[2.2.1]heptan-2-one (compound 12):

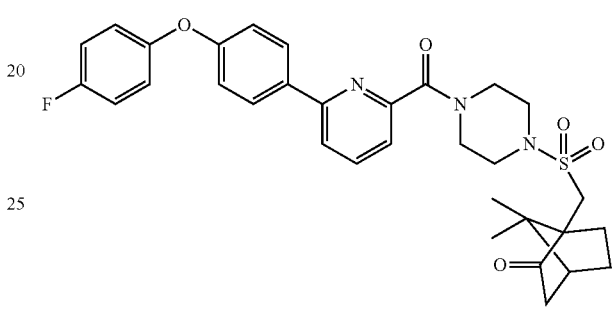

(6-(4-(4-fluorophenoxy)phenyl)pyridin-2-yl)(4-(methylsulfonyl)piperazin-1-yl)methanone (compound 13):

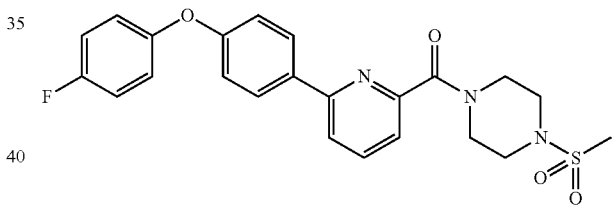

(4-((3,5-dimethylisoxazol-4-yl)sulfonyl)piperazin-1-yl) (6-(4-(4-fluorophenoxy)phenyl)pyridin-2-yl)methanone (compound 14):

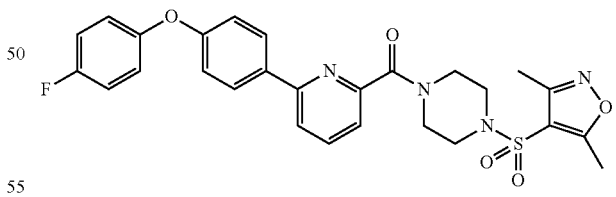

(6-(4-(4-fluorophenoxy)phenyl)pyridin-2-yl)(4-(pyridin-3-ylsulfonyl)piperazin-1-yl)methanone (compound 15):

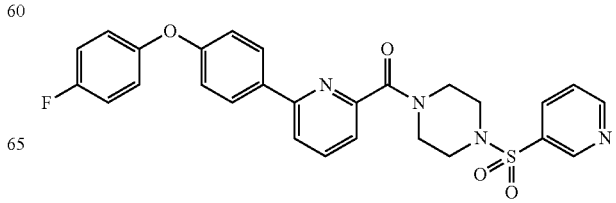

(6-(4-fluorophenoxy)phenyl)pyridin-2-yl)(4-((3-(trifluoromethoxy)phenyl)sulfonyl)piperazin-1-yl)methanone (compound 16):

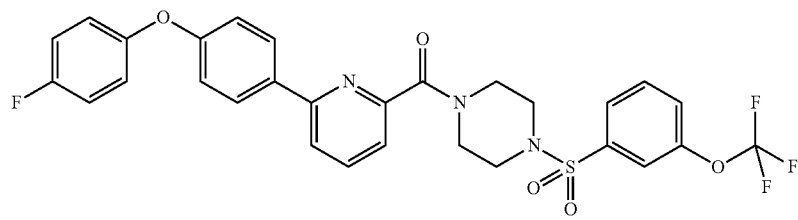 [SMILES: O=C(c1cccc(-c2ccc(Oc3ccc(F)cc3)cc2)n1)N1CCN(S(=O)(=O)c2cccc(OC(F)(F)F)c2)CC1]

4-((4-(6-(4-(4-fluorophenoxy)phenyl)picolinoyl)piperazin-1-yl)sulfonyl)benzonitrile (compound 17):

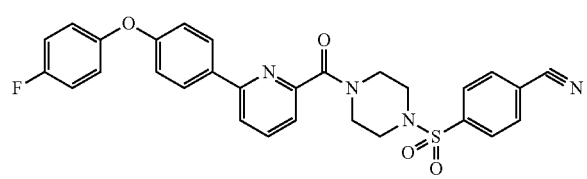 [SMILES: N#Cc1ccc(S(=O)(=O)N2CCN(C(=O)c3cccc(-c4ccc(Oc5ccc(F)cc5)cc4)n3)CC2)cc1]

3-((4-(6-(4-(4-fluorophenoxy)phenyl)picolinoyl)piperazin-1-yl)sulfonyl)benzoic acid (compound 18):

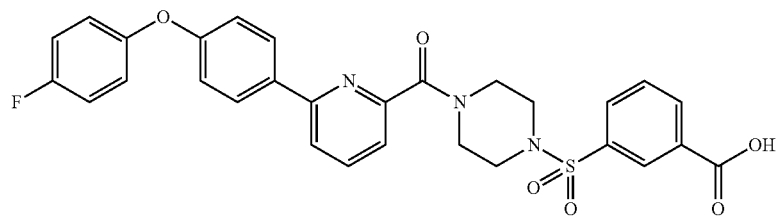 [SMILES: O=C(O)c1cccc(S(=O)(=O)N2CCN(C(=O)c3cccc(-c4ccc(Oc5ccc(F)cc5)cc4)n3)CC2)c1]

4-((4-(6-(4-(4-fluorophenoxy)phenyl)picolinoyl)piperazin-1-yl)sulfonyl)benzoic acid (compound 19):

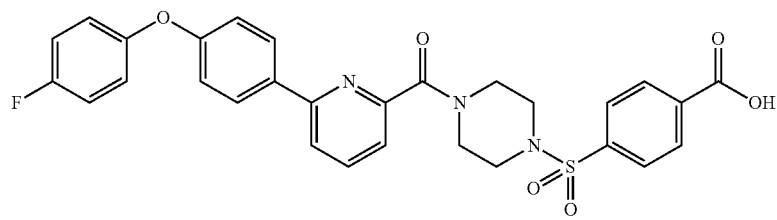 [SMILES: O=C(O)c1ccc(S(=O)(=O)N2CCN(C(=O)c3cccc(-c4ccc(Oc5ccc(F)cc5)cc4)n3)CC2)cc1]

(2-fluoro-5-((4-(6-(4-(4-fluorophenoxy)phenyl)picolinoyl)piperazin-1-yl)sulfonyl)benzonitrile (compound 59):

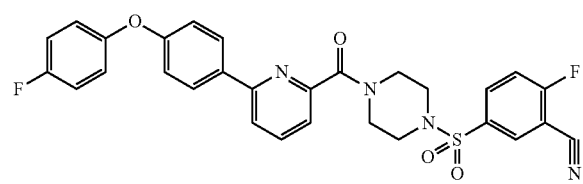 [SMILES: N#Cc1cc(S(=O)(=O)N2CCN(C(=O)c3cccc(-c4ccc(Oc5ccc(F)cc5)cc4)n3)CC2)ccc1F]

(6-(4-(4-fluorophenoxy)phenyl)pyridin-2-yl)(4-((4-methyl-3,4-dihydro-2H-benzo[b][1,4]oxazin-7-yl)sulfonyl)piperazin-1-yl)methanone (compound 60):

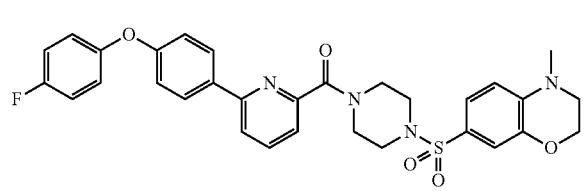 [SMILES: CN1CCOc2cc(S(=O)(=O)N3CCN(C(=O)c4cccc(-c5ccc(Oc6ccc(F)cc6)cc5)n4)CC3)ccc21]

Example 9

Synthesis of Compound 20

Scheme 17

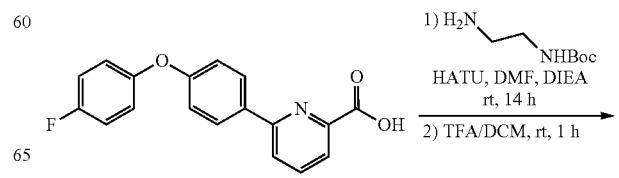

-continued

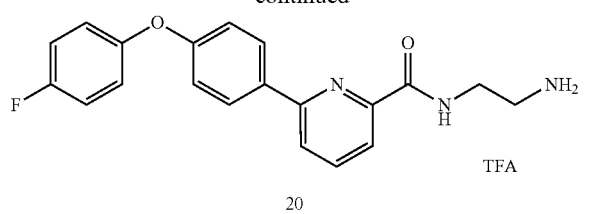

20

A 50 mL round bottom flask was charged with compound 5 (1.0 g, 3.2 mmol), 2-Boc-amino ethyl amine (0.52 g, 3.2 mmol), HATU (1.3 g, 3.4 mmol), DIEA (1.1 mL, 6.4 mmol) and DMF (5 mL). The mixture was stirred at room temperature overnight, diluted with water, and extracted with EtOAc. The organic layer was separated and the solvent was evaporated. The residue was re-dissolved in 6 mL of DCM/TFA (1:1) and the resulting mixture was stirred at room temperature for 1 h. The solvent was removed by rotary evaporation and the residue was dried under vacuum to give compound 20 as a yellowish solid (1.4 g, 97% yield) (m/z+H)=352).

Example 10

Synthesis of 6-(4-(4-fluorophenoxy)phenyl)-N-(2-(methylsulfonamido)ethyl)picolinamide (compound 21)

Scheme 18

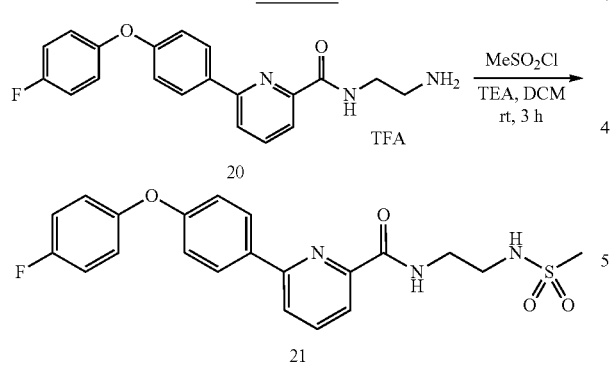

A 20 mL round bottom flask was charged with compound 20 (80 mg, 0.21 mmol), methyl sulfonyl chloride (16 µL, 0.21 mmol), TEA (0.15 mL, 0.6 mmol) and DCM (2 mL). The reaction mixture was stirred at room temperature for 3 h, diluted with water, and extracted with EtOAc. The organic layer was separated and concentrated by evaporation. The residue was subjected to column chromatography on silica gel (hexanes/EtOAc) to give compound 21 as a white solid (85 mg, 95% yield, (m/z+H)=430, $^1$H NMR (CDCl$_3$) δ ppm: 8.5 (br, 1H); 7.8-8.3 (m, 5H); 7.1 (m, 6H); 5.2 (br, 1H); 3.7 (m, 2H); 3.6 (m, 2H); 3.0 (s, 3H)).

Example 11

Synthesis of 6-(4-(4-fluorophenoxy)phenyl)-N-(2-(pyridine-3-sulfonamido)ethyl)picolinamide (compound 22)

Scheme 19

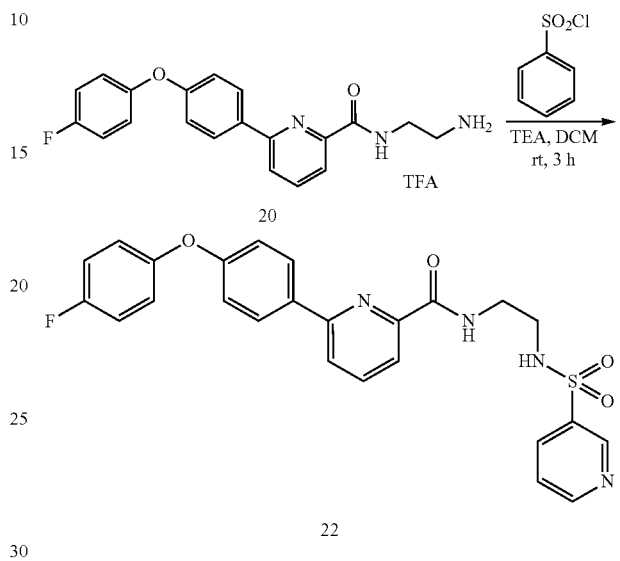

A 20 mL round bottom flask was charged with compound 20 (86 mg, 0.21 mmol), pyridine-3-sulfonyl chloride (37 mg, 0.21 mmol), TEA (0.15 mL, 0.6 mmol) and DCM (2 mL). The reaction mixture was stirred at room temperature 3 h, diluted with water, and extracted with EtOAc. The organic layer was separated and concentrated by evaporation. The residue was purified by column chromatography on silica gel (hexanes/EtOAc) to give compound 22 as a white solid (93 mg, 90% yield, (m/z+H)=493, $^1$H NMR (CDCl$_3$) δ ppm: 8.8 (br, 1H); 6.5-8.5 (m, 15H); 5.8 (br, 1H); 3.7 (m, 2H); 3.6 (m, 2H)).

The following compounds were prepared similarly:

6-(4-(4-fluorophenoxy)phenyl)-N-(2-(3-(methylsulfonyl)phenylsulfonamido)ethyl)picolinamide (compound 23):

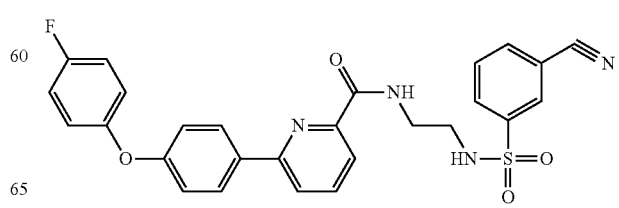

N-(2-(3-cyanophenylsulfonamido)ethyl)-6-(4-(4-fluorophenoxy)phenyl)picolinamide (compound 24):

Example 12

Synthesis of 2-(6-(4-(4-fluorophenoxy)phenyl)pyridin-2-yl)acetic acid (compound 25)

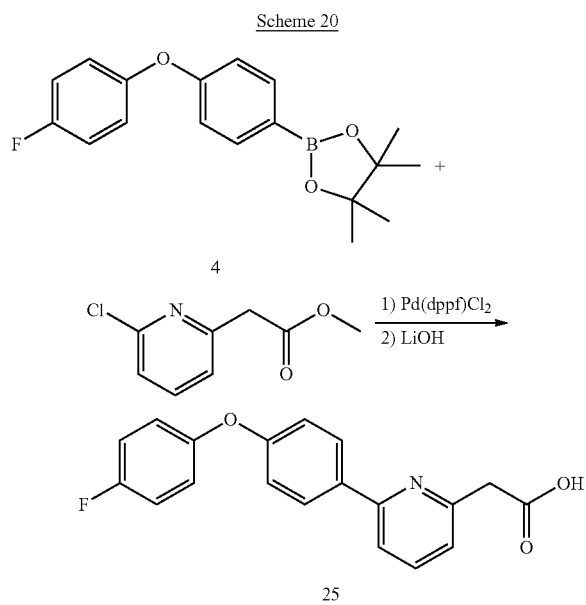

Step 1:

(6-Chloro-pyridin-2-yl)acetic acid methyl ester (200 mg, 1.1 mmol) in dimethoxyethane (DME) was degassed by repeating argon/vacuum cycles. Tetrakis(triphenylphosphine)palladium (124.5 mg, 0.1 mmol) was added and the mixture was degassed again. The suspension was stirred under an argon atmosphere for 10 min at room temperature. 2N $Na_2CO_3$ (2.5 mL) was added followed by compound 4 (411 mg, 1.6 mmol). The reaction mixture was heated at 90° C. for 18 h. Upon cooling to the room temperature, the reaction mixture was poured into DCM. The solids were removed by filtration, the filtrate was washed with $H_2O$, and the aqueous phase was extracted with EtOAc. The combined organic layers were dried over anhydrous $MgSO_4$ and concentrated to give the desired methyl ester intermediate as a pale yellow oil (182 mg, 50% yield, $R_f$=0.6, eluent (EtOAc:Hexanes=2:1), LC/MS: m/z=338 [M+H]$^+$).

Step 2:

The methyl ester from Step 1 above (64 mg, 0.19 mmol) was dissolved in MeOH—$H_2O$ (3:1, 5 mL) and LiOH.n$H_2O$ (47.7 mg, 1.1 mmol) was added. The mixture was stirred for 3 h at room temperature. The reaction was concentrated, diluted with water and acidified with concentrated HCl to pH 5. The resultant mixture was extracted with EtOAc and the combined organic extracts were dried over anhydrous $MgSO_4$. The solvent was evaporated to give a brown residue which was purified by preparative TLC (DCM:MeOH=9:1) to give compound 25 as a white solid (54 mg, 86% yield, LC/MS: m/z=324 [M+H]$^+$, $^1$H NMR (400 MHz, $CD_3OD$): δ 7.99 (d, J=8.6 Hz, 2H), 7.76 (t, J=7.9 Hz, 1H), 7.61 (d, J=7.6 Hz, 1H), 7.32 (d, J=7.6 Hz, 1H), 7.02-7.17 (m, 6H), 3.78 (s, 2H)).

Example 13

Synthesis of (S)-2-(2-{6-[4-(4-fluoro-phenoxy)phenyl]-pyridin-2-yl}-acetylamino-propionic acid methyl ester (compound 26)

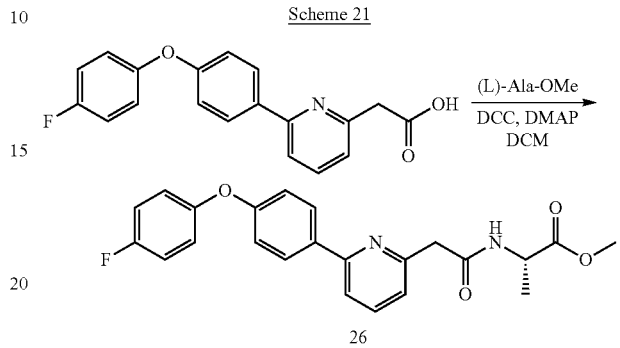

To a solution of compound 25 (30 mg, 0.1 mol) in DCM (1 mL) was added (L)-Ala-OMe (10.3 mg, 0.1 mmol), DCC (23.7 mg, 0.12 mmol) and DMAP (1.2 mg, 0.01 mmol). The reaction mixture was stirred overnight at room temperature. After the reaction was complete, $H_2O$ (1 mL) was added. The organic phase was separated and dried over anhydrous $Na_2SO_4$. The solvent was removed and the residue was purified by the preparative TLC (MeOH:DCM=1:9, then EtOAc:Hexane=2:1) to give compound 26 (2 mg, 81% yield, LC/MS: m/z=409 [M+H]$^+$, $^1$H NMR (400 MHz, $CD_3OD$): δ 8.04 (d, J=8.8 Hz, 2H), 7.81 (t, J=7.8 Hz 1H), 7.7 (d, J=7.2 Hz, 1H), 7.31 (d, J=7.0 Hz, 1H), 7.03-7.1 (m, 6H), 4.47 (q, J=7.3 Hz, 1H), 3.83 (s, 2H), 3.71 (s, 3H), 1.42 (d, J=7.2 Hz, 3H)).

Example 14

Synthesis of (S)-2-(2-{6-[4-(4-fluoro-phenoxy)-phenyl]-pyridin-2-yl}-acetylamino-propionic acid (compound 27)

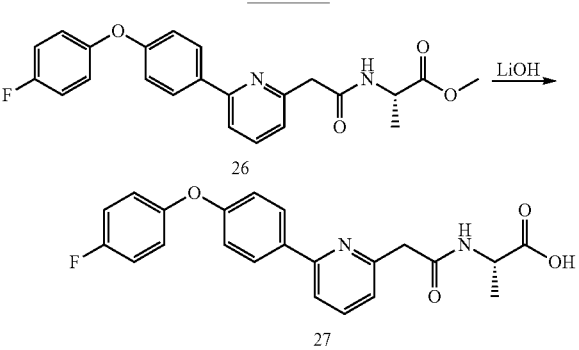

Compound 26 (106 mg, 0.39 mmol) was dissolved in THF (5.2 mL). 0.1N LiOH (5.2 mL) was added and the reaction mixture was stirred at 0° C. for 2 h. The reaction mixture was adjusted pH 4 with 5% HCl and concentrated under reduced pressure. The residue was purified by preparative TLC (DCM:MeOH=9:1) to give compound 27 as an off-white solid (56 mg, 55%, LC/MS: m/z=395 [M+H]+, $^1$H NMR (400 MHz, CD$_3$OD): δ 7.8 (d, J=9.0 Hz, 2H), 7.67 (t, J=7.6 Hz, 1H), 7.58 (d, J=7.5 Hz, 1H), 7.19 (d, J=7.5 Hz, 1H), 6.88-7.03 (m, 6H), 4.30 (q, J=7.3 Hz, 1H), 3.70 (s, 2H), 1.28 (d, J=7.2 Hz, 3H)).

Example 15

General Methodology for Amino Acid Coupling Reactions

Scheme 23

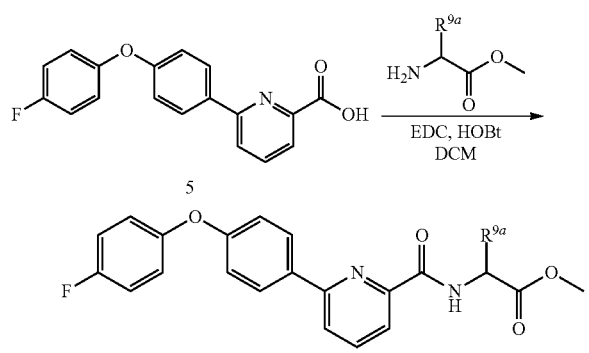

A mixture of compound 5 (0.81 mmol), HOBt (0.97 mmol), EDC (0.97 mmol) in dry dichloromethane was stirred at 0° C. for 1 h. The appropriate amino acid methyl ester (0.97 mmol), e.g., wherein R$^{9a}$ is hydrogen; or alkyl; alkenyl; cycloalkyl; heterocyclo; aryl; heteroaryl; aralkyl; or (heteroaryl)alkyl, any which is optionally substituted, and DIEA (1.2 mmol) were added thereto and the mixture was stirred until the reaction was complete (approximately 8 to 48 h depending on the amino acid methyl ester). The reaction mixture was quenched with saturated NH$_4$Cl and extracted with EtOAc and DCM. The combined organic phase was dried over anhydrous Na$_2$SO$_4$ and concentrated to give an oil. The oil was purified by automated column chromatography on silica gel using a CombiFlash® system (5% MeOH in DCM) to give desired methyl ester.

Compounds wherein R$^{9a}$ is:

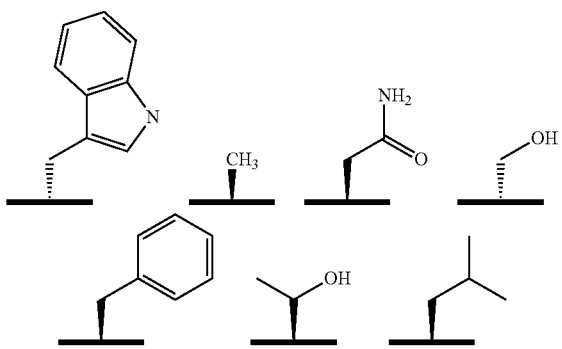

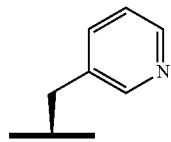

were prepared according to this methodology:

Compound 28: R$_f$=0.3, Eluent (EtOAc:Hexanes=1:1), LC/MS: m/z=472 [M+H]+.

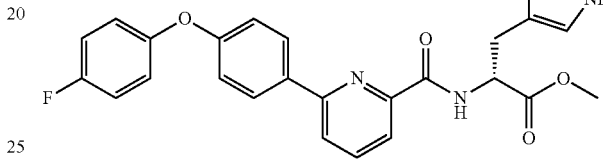

Compound 29: R$_f$=0.6, Eluent (EtOAc:DCM=1:2), LC/MS: m/z=324 [M+H]+.

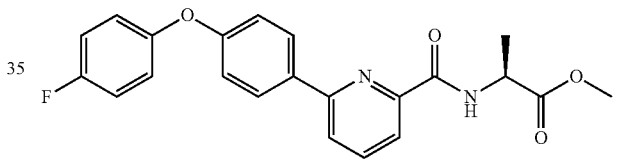

Compound 30: R$_f$=0.8, Eluent (MeOH:DCM=1:11), LC/MS: m/z=438 [M+H]+.

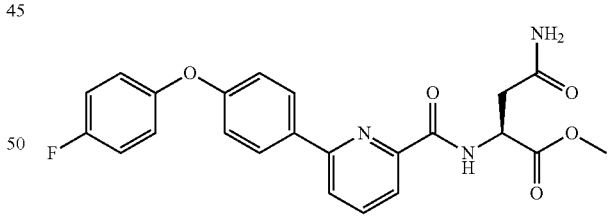

Compound 31: R$_f$=0.6, Eluent (MeOH:DCM=1:10), LC/MS: m/z=411 [M+H]+.

Compound 32: R$_f$=0.7, Eluent (MeOH:DCM=1:11), LC/MS: m/z=471 [M+H]$^+$.

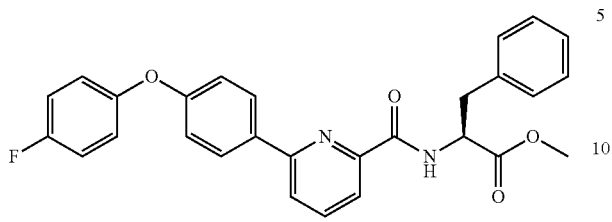

Compound 34: R$_f$=0.8, Eluent (MeOH:DCM=1:11), LC/MS: m/z=438 [M+H]$^+$.

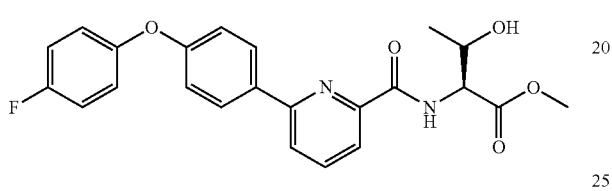

Compound 35: R$_f$=0.4, Eluent (EtOAc:Hexane=1:1), LC/MS: m/z=437 [M+H]$^+$.

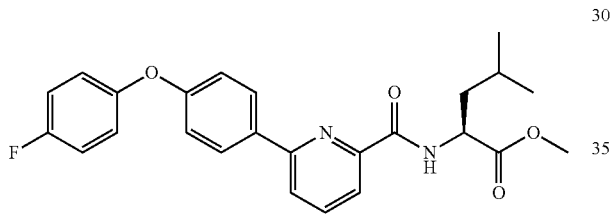

Compound 36: R$_f$=0.6, Eluent (MeOH:DCM=1:10), LC/MS: m/z=472 [M+H]$^+$.

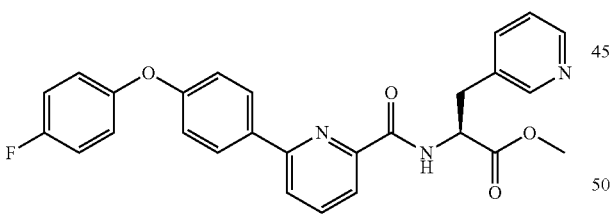

Compound 33 was prepared as a mixture of E/Z isomers using similar methodology, as shown in Scheme 24:

Scheme 24

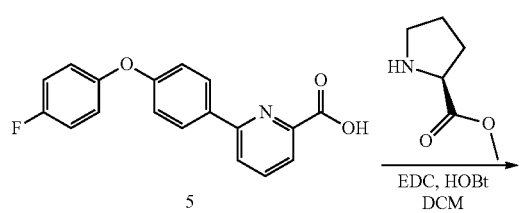

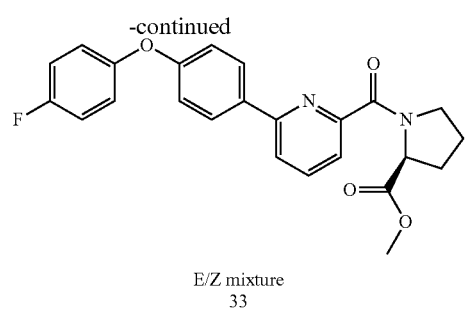

E/Z mixture
33

Compound 33: R$_f$=0.8, Eluent (MeOH:DCM=10:1), LC/MS: m/z=421 [M+H]$^+$.

Example 16

General Methodology for Synthesis of Primary Carboxamides

Scheme 25A and B

A

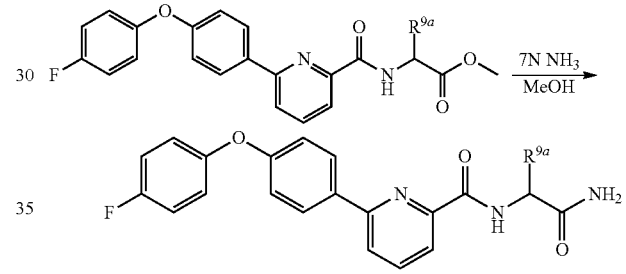

B

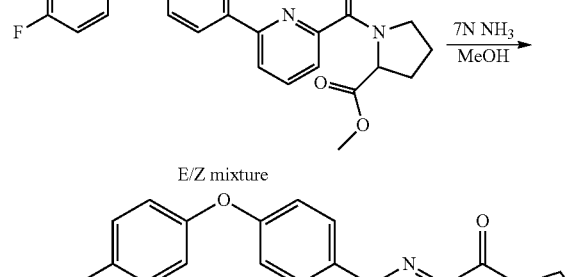

The compounds from Example 15 were dissolved in 7N NH$_3$/MeOH and stirred until the reaction was complete (2 h to overnight depending on the starting material) at room temperature. The solvent was evaporated and the resulting crude products were purified by automated column chromatography on silica gel using a CombiFlash® system (10% MeOH in DCM) and then recrystallized from isopropanol or EtOAc/hexanes to give the desired primary carboxamides. Compounds 37-45 were prepared according to this methodology:

6-[4-(4-fluoro-phenoxy)-phenyl]-pyridine-2-carboxylic acid [(R)-1-carbamoyl-2-(1H-indol-3-yl)-ethyl]-amide (compound 37): LC/MS: m/z=495 [M+H]$^+$; $^1$H NMR (400 MHz, CD$_3$CN): δ 9.2 (s, br, 1H), 8.54 (d, J=8.0 Hz, 1H, NH), 7.90-7.98 (m, 3H), 7.67 (d, J=8.0 Hz, 1H), 7.37 (d, J=8.0 Hz, 1H), 7.22-6.96 (m, 11H), 6.48 (br, s, 1H), 5.84 (br, s, 1H), 4.79-4.84 (m, 1H), 3.39 (d, J=6.0 Hz, 2H)

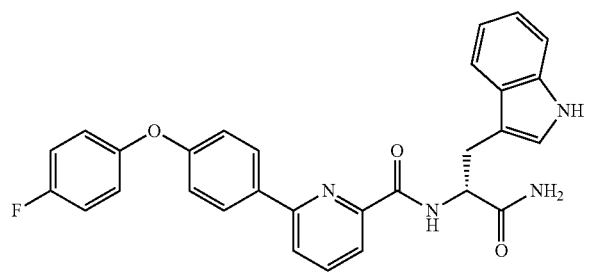 [SMILES: NC(=O)[C@@H](Cc1c[nH]c2ccccc12)NC(=O)c1cccc(-c2ccc(Oc3ccc(F)cc3)cc2)n1]

6-[4-(4-fluoro-phenoxy)-phenyl]-pyridine-2-carboxylic acid ((S)-1-carbamoyl-ethyl)-amide (compound 38): LC/MS: m/z=379 [M+H]$^+$; $^1$H NMR (400 MHz, CDCl$_3$): δ 8.45 (d, J=7.4 Hz, 1H), 8.10 (d, J=7.6 Hz, 1H), 7.83-7.99 (m, 4H), 7.05-7.11 (m, 6H), 6.35 (s, br, 1H), 5.39 (s, br, 1H), 4.73 (dq, J=7.1 Hz, 7.4 Hz, 1H), 1.50 (d, J=7.0 Hz, 3H).

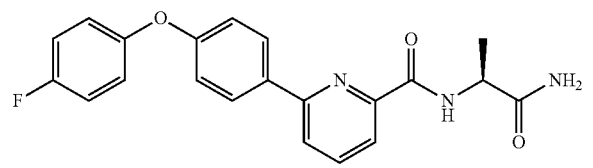 [SMILES: C[C@H](NC(=O)c1cccc(-c2ccc(Oc3ccc(F)cc3)cc2)n1)C(N)=O]

(S)-2-({6-[4-(4-fluoro-phenoxy)-phenyl]-pyridine-2-carbonyl}-amino)-succinamide (compound 39): LC/MS: m/z=423 [M+H]$^+$; $^1$H NMR (400 MHz, DMSO): δ 9.40 (d, J=8.8 Hz, 1H), 8.28 (d, J=8.8 Hz, 2H), 8.15 (d, j=8.8 Hz, 1H), 8.06 (t, J=7.7 Hz, 7.7 Hz, 1H), 7.96 (d, J=6.8 Hz, 1H), 7.49 (s, br, 1H), 7.42 (s, br, 1H), 7.10-7.19 (m, 5H), 7.01 (s, br, 1H) 4.64-4.69 (m, 1H), 2.76 (dd, J=7.0 Hz, 15.0 Hz, 1H), 2.57 (dd, J=5.0 Hz, 15.0 Hz, 1H).

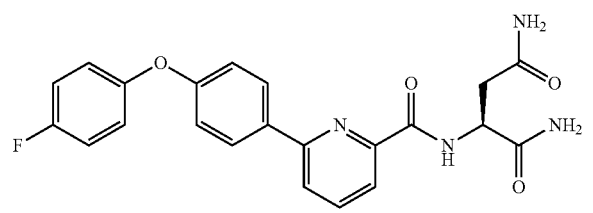 [SMILES: NC(=O)C[C@H](NC(=O)c1cccc(-c2ccc(Oc3ccc(F)cc3)cc2)n1)C(N)=O]

6-[4-(4-fluoro-phenoxy)-phenyl]-pyridine-2-carboxylic acid ((R)-1-carbamoyl-2-hydroxyl-ethyl)-amide (compound 40): LC/MS: m/z=396 [M+H]$^+$; $^1$H NMR (400 MHz, CD$_3$OD): δ 8.21 (d, J=9.0 Hz, 2H), 8.02-8.10 (m, 3H), 7.07-7.20 (m, 6H), 4.67 (t, j=4.8 Hz, 1H), 4.03 (dd, J=4.7 Hz, 11.2 Hz, 1H), 3.94 (dd, J=4.7 Hz, 11.2 Hz, 1H).

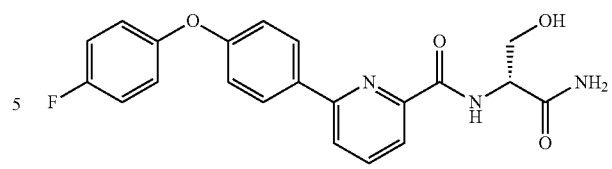

6-[4-(4-fluoro-phenoxy)-phenyl]-pyridine-2-carboxylic acid ((S)-1-carbamoyl-2-phenyl-ethyl)-amide (compound 41): LC/MS: m/z=456 [M+H]$^+$; $^1$H NMR (400 MHz, CDCl$_3$): δ 8.61 (d, J=8.0 Hz, 1H), 8.07 (d, J=7.7 Hz, 1H), 7.8-7.9 (m, 4H), 7.23-7.37 (m, 4H), 7.04-7.13 (m, 6H), 5.97 (s, br, 1H), 5.33 (s, br, 1H), 4.85-4.93 (m, 1H), 3.40 (dd, J=6.1 Hz, 14 Hz, 1H), 3.19 (dd, J=7.2 Hz, 13.9 Hz, 1H).

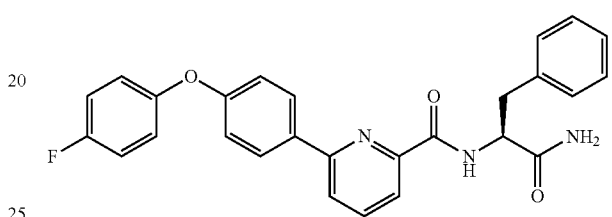

(S)-1-{6-[4-(4-fluoro-phenoxy)-phenyl]-pyridine-2-carbonyl}-pyrrolidine-2-carboxylic acid amide (compound 42): The product was the mixture of the two isomers (E:Z=3:1). LC/MS: m/z=406 [M+H]$^+$. The NMR of the major isomer is reported: $^1$H NMR (400 MHz, CDCl$_3$): δ 7.70-8.07 (m, 4H), 7.01-7.11 (m, 7H), 6.93 (s, br, 1H), 5.37 (s, br, 1H), 4.87 (m, 1H), 4.08-4.16 (m, 1H), 3.89-4.02 (m, 1H), 2.40-2.5 (m, 1H), 2.10-2.19 (m, 1H), 1.91-2.09 (m, 2H).

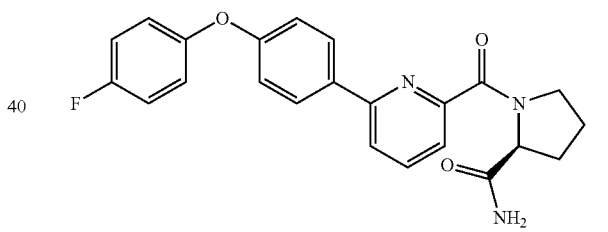

6-[4-(4-fluoro-phenoxy)-phenyl]-pyridine-2-carboxylic acid ((S)-1-carbamoyl-2-hydroxy-propyl)-amide (compound 43): LC/MS: m/z=410 [M+H]$^+$; $^1$H NMR (400 MHz, CD$_3$OD): δ 8.21 (d, J=9.0 Hz, 2H), 8.01-8.11 (m, 3H), 7.07-7.20 (m, 6H), 4.55 (d, J=3.3 Hz, 1H), 4.34-4.46 (m, 1H), 1.27 (d, J=6.3 Hz, 3H).

6-[4-(4-fluoro-phenoxy)-phenyl]-pyridine-2-carboxylic acid ((S)-1-carbamoyl-3-methyl-butyl)-amide (compound 44): LC/MS: m/z=422 [M+H]$^+$; $^1$H NMR (400 MHz, CD$_3$OD): δ 8.19 (d, J=9.0 Hz, 2H), 8.00-8.10 (m, 3H), 7.07-7.20 (m, 6H), 4.70-4.76 (m, 1H), 1.73-1.82 (m, 3H), 1.0 (d, J=4.6 Hz, 6H).

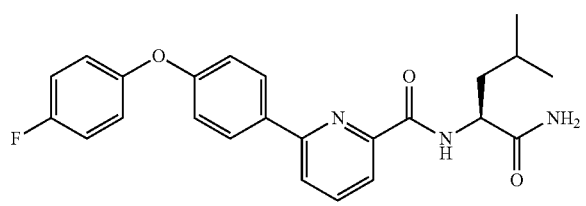 [SMILES: CC(C)C[C@H](NC(=O)c1cccc(-c2ccc(Oc3ccc(F)cc3)cc2)n1)C(N)=O]

(S)—N-(1-amino-1-oxo-3-(pyridin-3-yl)propan-2-yl)-6-(4-(4-fluorophenoxy)phenyl)picolinamide (compound 45): LC/MS: m/z=422 [M+H]+; 1H NMR (400 MHz, CD3OD): δ 8.50 (d, J=1.6 Hz, 1H), 8.41 (d, J=3.2 Hz, 1H), 8.14 (d, J=9.0 Hz, 2H), 7.90-8.0 (m, 3H), 4.9-5.0 (m, 1H), 3.2-3.45 (m, 2H).

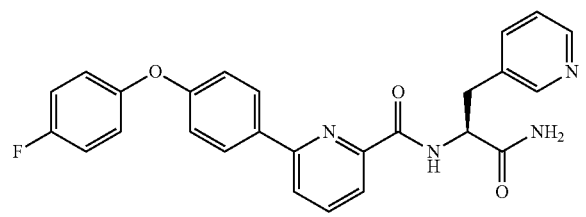 [SMILES: NC(=O)[C@H](Cc1cccnc1)NC(=O)c1cccc(-c2ccc(Oc3ccc(F)cc3)cc2)n1]

Example 17

General Methodology for Synthesis of Primary Carboxamides

Scheme 26

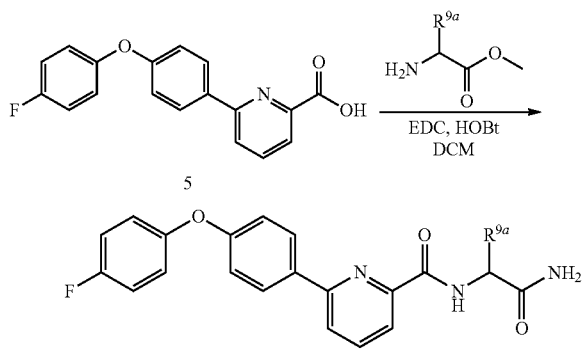

A mixture of compound 5 (0.81 mmol), HOBt (0.97 mmol), and EDC (0.97 mmol) in dry dichloromethane was stirred at 0° C. for 1 h. Amino acid amide (0.97 mmol) and DIEA (1.2 mmol) were added and the mixture was stirred until the reaction was complete (approximately 8 to 48 h depending on the amino acid amide). The reaction mixture was quenched with saturated NH4Cl and extracted with EtOAc and DCM. The combined organic phases were dried over anhydrous Na2SO4 and concentrated to give an oil. The resulting residue was purified by automated column chromatography on silica gel using a CombiFlash® system (5% MeOH in DCM) to give the desired product. Compounds wherein R$^{9a}$ is:

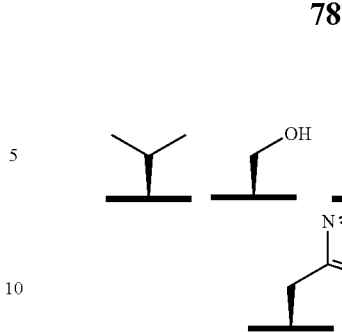

were prepared according to this methodology:

6-[4-(4-fluoro-phenoxy)-phenyl]-pyridine-2-carboxylic acid ((S)-1-carbamoyl-2-methyl-propyl)-amide (compound 46): LC/MS: m/z=408 [M+H]+; 1H NMR (400 MHz, CD3OD): δ 8.17 (d, J=6.9 Hz, 2H), 8.03-8.08 (m, 3H), 7.10-7.17 (m, 6H), 4.53 (d, J=6.2 Hz, 1H), 2.22-2.28 (m, 1H), 1.07 (dd, J=6.8 Hz, 8.7 Hz, 6H).

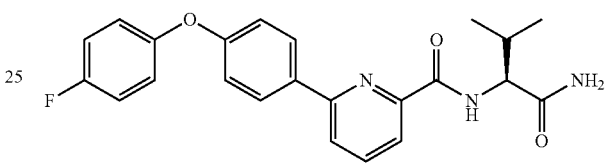

6-[4-(4-fluoro-phenoxy)-phenyl]-pyridine-2-carboxylic acid ((S)-1-carbamoyl-2-hydroxy-ethyl)-amide (compound 47): LC/MS: m/z=396 [M+H]+; 1H NMR (400 MHz, CDCl3): δ 9.09 (d, J=7.0 Hz, 1H), 7.8-8.1 (m, 5H), 7.0-7.11 (m, 6H), 6.85 (s, br, 1H), 5.52 (s, br, 1H), 4.65-4.70 (m, 1H), 4.31 (d, J=10.7 Hz, 1H), 3.76-3.81 (m, 1H), 3.18-3.2 (s, br, 1H).

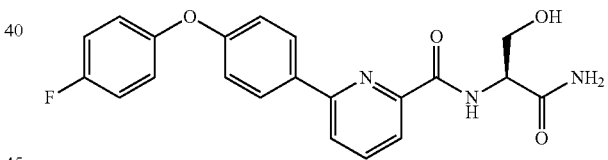

6-[4-(4-fluoro-phenoxy)-phenyl]-pyridine-2-carboxylic acid [(S)-1-carbamoyl-2-(4-hydroxy-phenyl)-ethyl]-amide (compound 48): LC/MS: m/z=472 [M+H]+; 1H NMR (400 MHz, CD3OD): δ 7.97 (d, J=9.0 Hz, 2H), 7.83-7.94 (m, 3H), 6.97-7.08 (m, 8H), 6.62 (d, J=8.8 Hz, 2H), 4.68 (t, J=6.3 Hz, 1H), 3.0 (d, J=6.3 Hz, 2H).

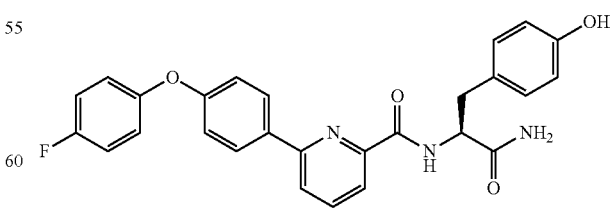

6-[4-(4-fluoro-phenoxy)-phenyl]-pyridine-2-carboxylic acid [(S)-1-carbamoyl-2-(1H-imidazol-4-yl)-ethyl]-amide (compound 49): LC/MS: m/z=446 [M+H]+; 1H NMR (400 MHz, CD3OD): δ 8.80 (d, J=1.5 Hz, 1H), 8.18 (d, J=8.7 Hz, 2H), 7.97-8.10 (m, 3H), 7.35 (s, br, 1H), 7.08-7.21 (m, 6H), 4.95-5.01 (m, 1H), 3.49 (dd, J=5.5 Hz, 15 Hz, 1H), 3.3 (d, J=7.7 Hz 1H).

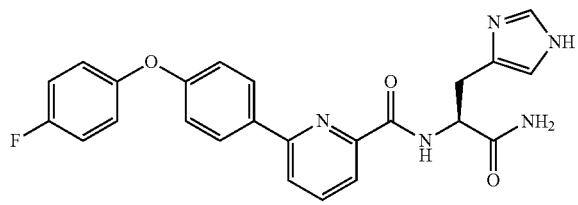 [SMILES: NC(=O)[C@H](Cc1c[nH]cn1)NC(=O)c1cccc(-c2ccc(Oc3ccc(F)cc3)cc2)n1]

Example 18

Synthesis of (S)—N-(1,6-diamino-1-oxohexan-2-yl)-6-(4-(4-fluorophenoxy)phenyl)picolinamide (compound 51)

Scheme 27

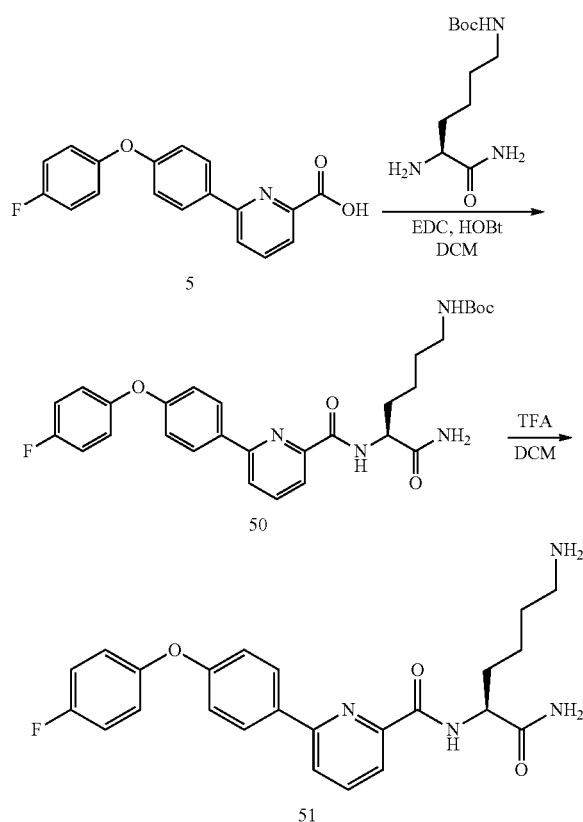

A mixture of compound 5 (309 mg, 1.0 mmol), HOBt (162.2 mg, 1.2 mmol), and EDC (230 mg, 1.2 mmol) in dry dichloromethane was stirred at 0° C. for 1 h. L-lys (Boc)-NH$_2$.HCl (338 mg, 1.2 mmol) and DIEA (1.2 mmol) were added thereto and the mixture was stirred overnight. The reaction mixture was quenched with saturated NH$_4$Cl and the organic layer was separated. The aqueous layer extracted with EtOAc and DCM. The combined organic layers were dried over anhydrous Na$_2$SO$_4$ and concentrated to a white solid. The residue was purified by automated column chromatography on silica gel using a CombiFlash® system (7% MeOH in DCM) to give compound 50 (500 mg, 93%, R$_f$=0.5; Eluent (DCM:MeOH=9:1), LC/MS: m/z=537 [M+H]$^+$).

Compound 50 (200 mg, 0.37 mmol) was dissolved in DCM (5 mL). Trifluoroacetic acid (5 mL) was added at 0° C. and the reaction mixture was stirred for 1 h at 0° C. and then allowed to slowly warm up to room temperature. After the reaction was complete, the solvent was removed and the resulting residue was purified by reverse phase column chromatography (CH$_3$CN/H$_2$O). The product was lyophilized to give compound 51 as a white solid as a TFA salt (102 mg, 50% yield, LC/MS: m/z=437 [M+H]$^+$, $^1$H NMR (400 MHz, MeOH-d$_4$): δ 8.25 (d, J=9.0 Hz, 2H), 8.06-8.17 (m, 3H), 7.12-7.26 (m, 6H), 7.71-7.78 (m, 1H)).

Example 19

General synthesis (S)-2-(6-(4-(4-(trifluoromethyl)phenoxy)phenyl)picolinamido)succinamide (compound 53) and (S)-2-(6-(4-(4-(trifluoromethyl)phenoxy)phenyl)picolinamido)pentanediamide (compound 54)

Scheme 28

A mixture of compound 52, prepared as described in Examples 1-5, (0.7 mmol), HOBt (0.84 mmol), and EDC (0.84 mmol) in dry dichloromethane was stirred at 0° C. for 1 h. An amino acid amide (0.84 mmol) and DIEA (1.1 mmol) were added thereto and the mixture was stirred until the completion (approximately 8 to 48 h depending on the amino acid amide). The reaction mixture was quenched with saturated NH$_4$Cl and then extracted with EtOAc and DCM. The combined organic phase was dried over anhydrous Na$_2$SO$_4$ and concentrated to give a solid residue. The residue was purified by preparative TLC (0.3% of NH$_4$OH and 5% MeOH in DCM) to give a pale yellow oily residue which was then crystallized with 5% EtOAc in hexanes. Compounds wherein R$^{9a}$ is:

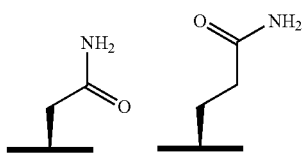

were prepared according to this methodology:
Compound 53: LC/MS: m/z=471 [M+H]$^+$; $^1$H NMR (400 MHz, CDCl$_3$): δ 7.25 (d, J=8.1 Hz, 1H), 8.28 (d, J=8.1 Hz, 2H), 8.23 (d, J=7.9 Hz, 1H), 8.0 (t, J=7.7 Hz, 1H), 7.91 (d, J=7.8 Hz, 1H), 7.7 (d, J=8.8 Hz, 2H), 7.4 (s, br, 1H), 7.3 (s, br, 1H), 7.18 (m, 4H), 6.92 (s, br, 1H), 7.05 (s, br, 1H), 4.64-4.56 (m, 1H), 2.68 (dd, J=7.0 Hz, 15 Hz, 1H), 2.50 (dd, J=4.6 Hz, 14.8 Hz, 1H),

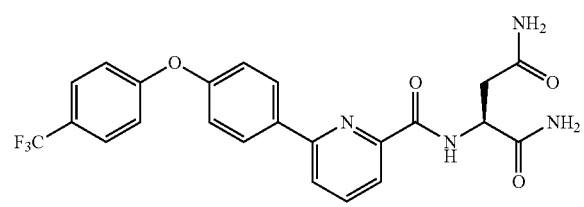 [SMILES: NC(=O)C[C@H](NC(=O)c1cccc(-c2ccc(Oc3ccc(C(F)(F)F)cc3)cc2)n1)C(N)=O]

Compound 54: LC/MS: m/z=487 [M+H]$^+$; $^1$H NMR (400 MHz, DMSO): δ 8.86 (d, J=7.8 Hz, 1H), 8.27 (d, J=9.0 Hz, 2H), 8.13 (d, J=8.1 Hz, 2H), 8.0 (t, J=7.8 Hz, 1H), 7.92 (d, J=7.6 Hz, 1H), 7.70 (d, J=8.5 Hz, 2H), 7.5 (s, br, 1H), 7.15-7.20 (m, 5H), 7.13 (s, br, 1H), 6.67 (s, br, 1H), 4.40 (m, 1H), 2.0 (m, 2H), 1.90 (m, 2H).

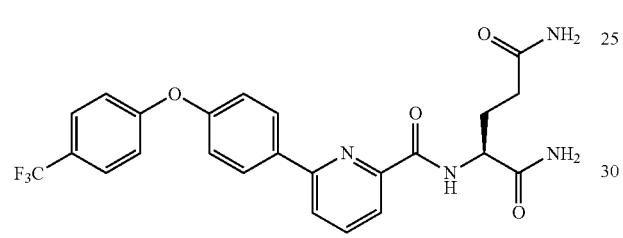

Example 20

Synthesis of 3-((4-(6-(4-fluorophenoxy)picolinoyl)piperazin-1-yl)sulfonyl)benzonitrile (compound 55)

Step 1:

Scheme 29

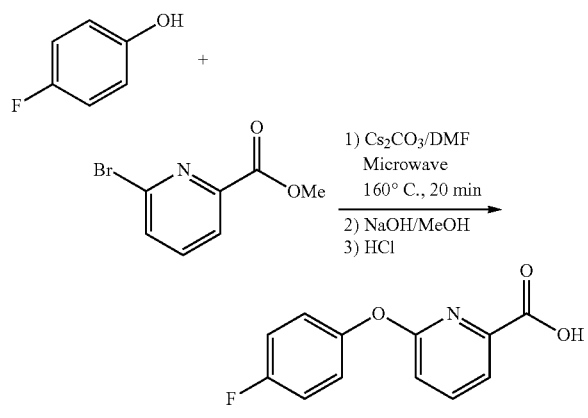

Synthesis of Compound 67

A 100 mL round bottom flask was charged with 4-fluorophenol (Aldrich, 0.56 g, 5 mmol), 6-bromopyridine-2-carboxylic acid methyl ester (1.08 g, 5 mmol), Cs$_2$CO$_3$ (1.6 g, 5 mmol) and DMF (5 mL). The reaction mixture was stirred at 160° C. in a microwave for 20 min, cooled to room temperature, diluted with water, and extracted with ethyl acetate. The organic layer was concentrated and the crude product was redissolved in a mixture of MeOH (5 mL)/2N NaOH (5 mL). The reaction mixture was stirred at 60° C. for 0.5 hr and then cooled to 0° C. in an ice bath. The pH of the reaction mixture was adjusted to 1 with conc. HCl. The white precipitate was filtered and dried to give compound 67 as white solid (1.1 g, yield 95%, (m/z+H)=234).

Step 2:

Scheme 30

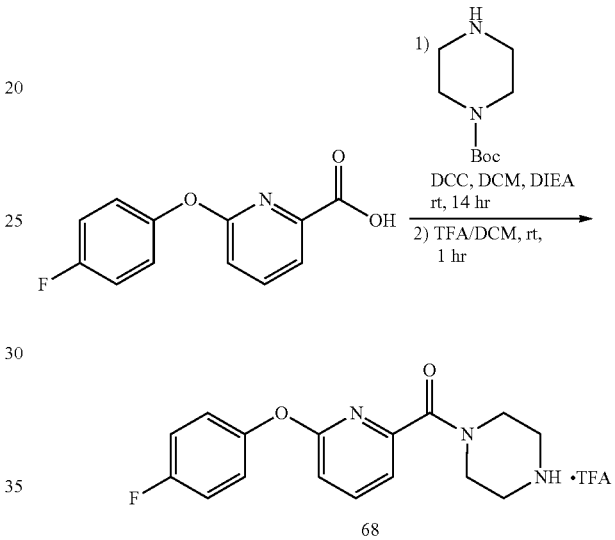

Synthesis of Compound 68

A 50 mL round bottom flask was charged with compound 67 (0.376 g, 1.6 mmol), 4-Boc-piperidine (Aldrich, 299 mg, 1.6 mmol), DCC (329 mg, 1.6 mmol), DIEA (0.33 mL, 1.6 mmol) and DCM (5 mL). The reaction mixture was stirred at room temperature overnight, diluted with water, and extracted with ethyl acetate. The organic layer was concentrated and the residue was redissolved in 6 mL of DCM/TFA (1:1). The resulting mixture was stirred at room temperature for 1 h. The solvent was removed and the residue was dried under vacuum to give compound 68 as yellowish solid (0.56 g, yield 90%, (m/z+H)=302).

Step 3:

Scheme 31

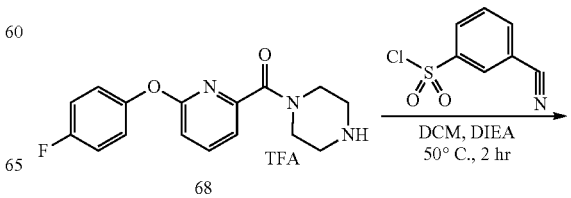

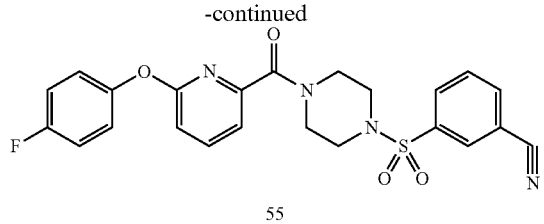

55

Synthesis of 3-((4-(6-(4-fluorophenoxy)picolinoyl)piperazin-1-yl)sulfonyl)benzonitrile A 50 mL round bottom flask was charged with compound 68 (100 mg, 0.19 mmol), 3-cyano phenylsulfonyl chloride (Aldrich, 33 µL, 0.19 mmol), DIEA (0.1 mL, 0.7 mmol) and DCM (5 mL). The reaction mixture stirred at 60° C. for 2 h, cooled to room temperature, diluted with water, and extracted with ethyl acetate. The organic layer was concentrated and the residue was subjected to flash column chromatography (hexanes/EtOAc) to give 3-((4-(6-(4-fluorophenoxy)picolinoyl)piperazin-1-yl)sulfonyl)benzonitrile (compound 55) as white solid (96 mg, yield 83%, (m/z+H)=467, $^1$HNMR (CDCl3) δ ppm: 6.80-7.90 (m, 11H); 3.6-3.8 (m, 4H); 2.9 (m, 2H); 2.5 (m, 2H)).

Example 21

Synthesis of 3-((4-(6-(4-fluorophenyl)picolinoyl)piperazin-1-yl)sulfonyl)benzonitrile (compound 56)

Step 1:

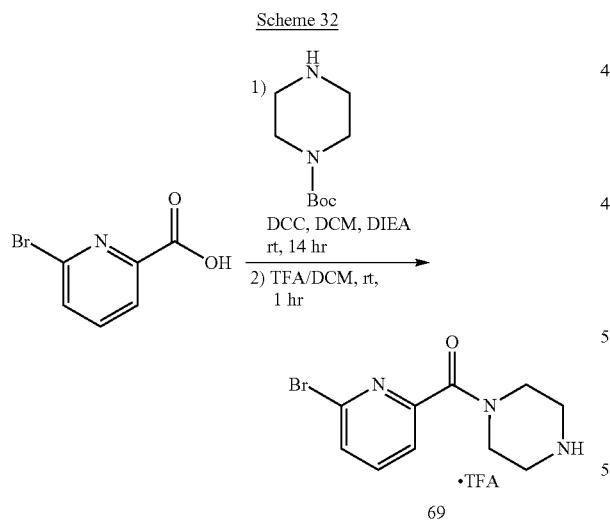

Synthesis of Compound 69

Compound 69 was synthesized in a similar way as that of compound 68 using 6-bromopyridine-2-carboxylic acid (202 mg, 1 mmol), Boc-piperazine (186 mg, 1 mmol), DCC (206 mg, 1 mmol), DIEA (0.33 mL, 1.6 mol) and DMF (2 mL) (yield 90%, (m/z+H)=271).

Step 2:

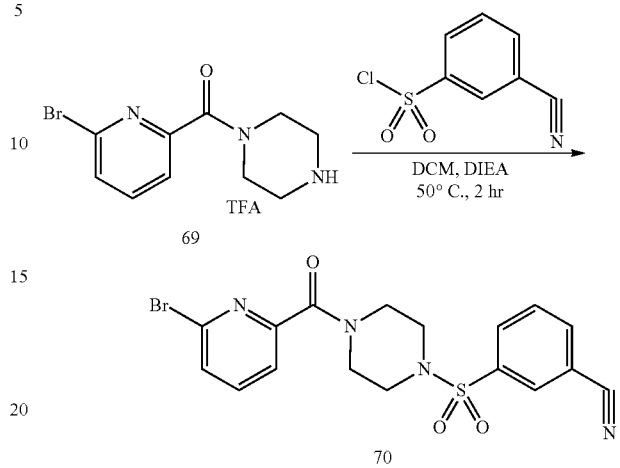

Synthesis of Compound 70

Compound 70 was synthesized in a similar way as that of compound 55 using compound 69 (70 mg, 0.19 mmol), 3-cyano phenylsulfonyl chloride (Aldrich, 33 µL, 0.19 mmol), DIEA (0.1 mL, 0.7 mmol) and DCM (5 mL) (yield 83%, (m/z+H)=436).

Step 3:

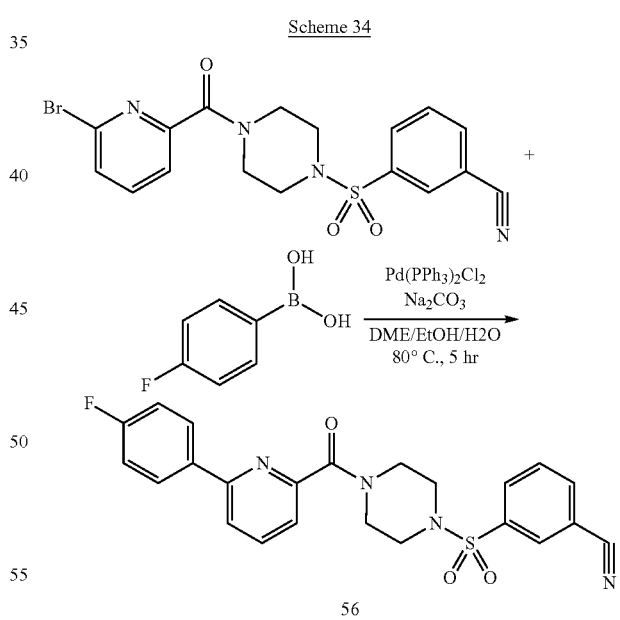

Synthesis of 3-((4(6-(4-fluorophenyl)picolinoyl)piperazin-1-yl)sulfonyl)benzonitrile A 50 mL round bottom flask was charged with compound 70 (436 mg, 1 mmol), 4-fluorophenyl boronic acid (Aldrich, 140 mg, 1 mmol), Pd(PPh$_3$)$_2$C$_2$ (35 mg, 0.05 mmol) and a mixture of DME/H$_2$O/EtOH (4 mL/4 mL/2 mL). The reaction mixture was purged with Ar and then stirred at 80° C. under Ar for 5 hrs. The reaction mixture was cooled to room temperature and diluted with EtOAc. The EtOAc was isolated, dried over MgSO$_4$, filtered, and concentrated. The residue was subjected to flash column chromatography (hexanes/EtOAc) to give 3-((4-(6-(4-fluorophenyl)picolinoyl)piperazin-1-yl)sulfonyl)benzonitrile (compound 56) as white solid (yield 75%, (m/z+H)=451, $^1$HNMR (CDCl3) δ ppm: 6.80-8.20 (m, 11H); 3.8 (m, 4H); 3.2 (m, 4H)).

Example 22

Synthesis of Compound 57

Scheme 35

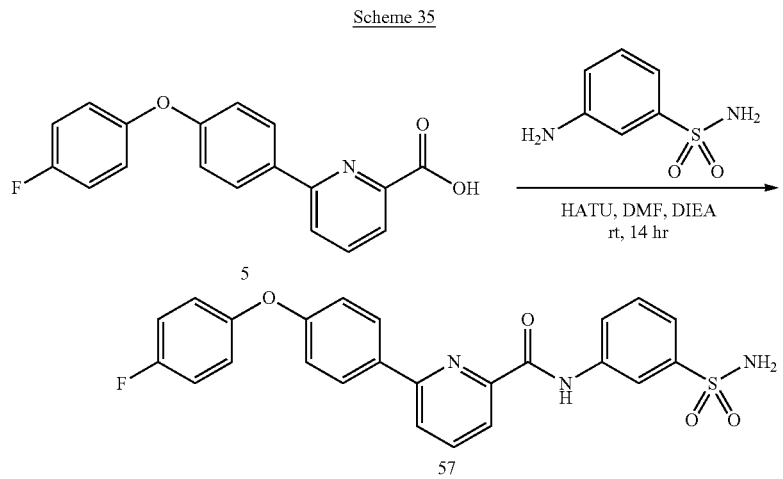

A 50 mL round bottom flask was charged with compound 5 (100.0 mg, 0.32 mmol), 3-amino-benzenesulfonamide (99 mg, 0.32 mmol), HATU (130 mg, 0.34 mmol), DIEA (0.11 mL, 0.64 mmol) and DMF (1 mL), The reaction mixture was stirred at room temperature overnight, diluted with water, and extracted with ethyl acetate. The organic layer was seperated and concentrated and the residue was subjected to flash column chromatography (EtOAc/hexanes) to give compound 57 as white solid (133 mg, yield 95%, (m/z+H)=464, $^1$HNMR (CDCl3) δ ppm: 6.7-8.5 (m, 15H), 4.8 (s, 1H)).

Example 23

Synthesis of (S)-3-((4-(4-(1,2-dihydroxyethyl)-6-(4-(4-fluorophenoxy)phenyl)picolinoyl)piperazin-1-yl)sulfonyl)benzonitrile (compound 58)

Step 1:

Scheme 36

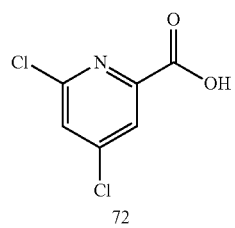

+

-continued

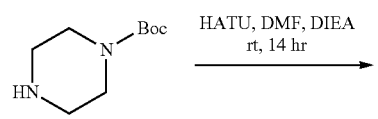

HATU, DMF, DIEA
rt, 14 hr
→

-continued

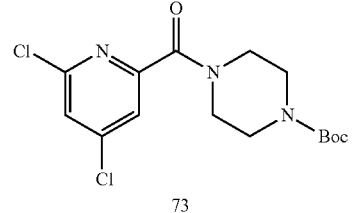

Synthesis of Compound 73

Compound 73 was synthesized following the similar procedure as that of compound 62 using dichloropyridine acid (compound 72) (0.5 g, 2.6 mmol), Boc-piperazine (0.48 g, 2.6 mmol), HATU (1.03 g, 2.73 mmol), DIEA (0.3 mL) and DMF (5 mL) (yield 96%, (m/z+H)=360).

Step 2:

Scheme 37

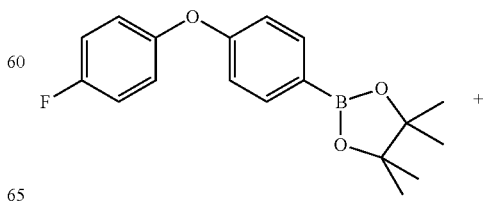

+

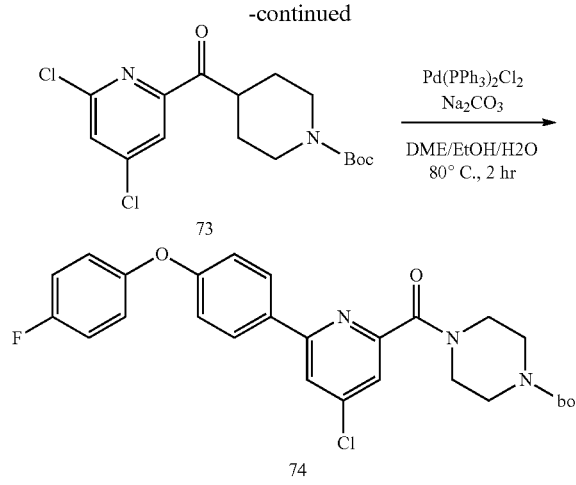

Synthesis of Compound 74

Compound 74 was synthesized following the similar procedure as that of compound 78 using compound 4 (314 mg, 1 mmol), compound 73 (359 mg, 1 mmol), Pd(PPh$_3$)$_2$Cl$_2$ (35 mg, 0.05 mmol) and a mixture of DME/H$_2$O/EtOH (2 mL/2 mL/1 mL) (yield 70%, (m/z+H)=512).

Step 3:

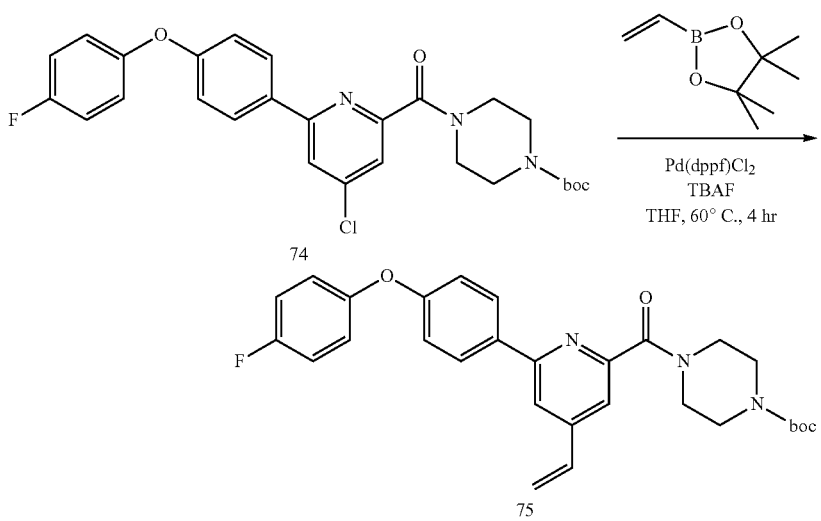

Scheme 38

Synthesis of Compound 75

Compound 75 was synthesized following the similar procedure as that of compound 5 using compound 74 (260 mg, 0.5 mmol), vinyl borate (102 μL, 0.6 mmol), Pd(dppf)Cl$_2$ (20 mg, 0.025 mmol), TBAF (1 M, 1 mL, 1 mmol), and THF (2 mL) (yield 90%, (m/z+H) 504).

Step 4:

Scheme 39

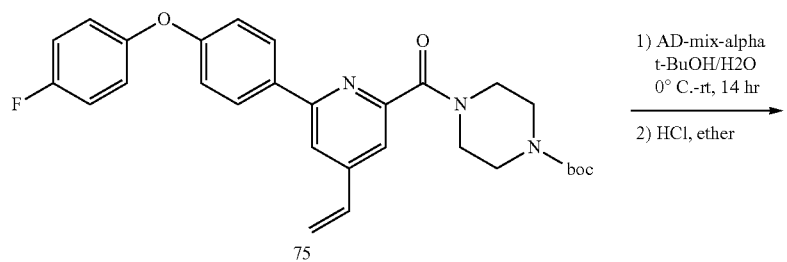

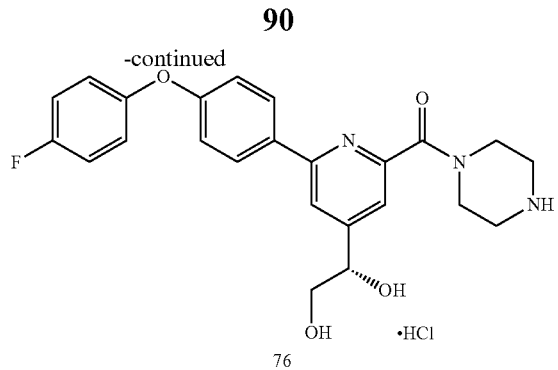

Synthesis of Compound 76

At 0° C., a 50 mL round bottom flask was charged with compound 75 (260 mg, 0.5 mmol), AD-mix-alpha (0.75 g), t-BuOH (3 mL) and $H_2O$ (3 mL) and the mixture was vigorously stirred overnight. The reaction mixture was extracted with ethyl acetate and the organic layer was separated and concentrated. The crude product was subjected to flash column chromatography on silica gel (EtOAc) to give desire diol as white foam. This foam was suspended in ca. 10 mL ether with HCl (2M) and stirred at room temperature overnight. The solid was filtered and dried to give compound 76 (165 mg, yield 70%, (m/z+H)=438).

Step 5:

Scheme 40

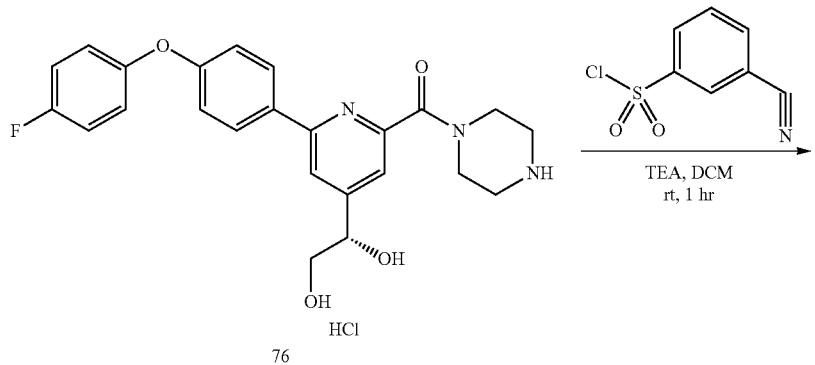

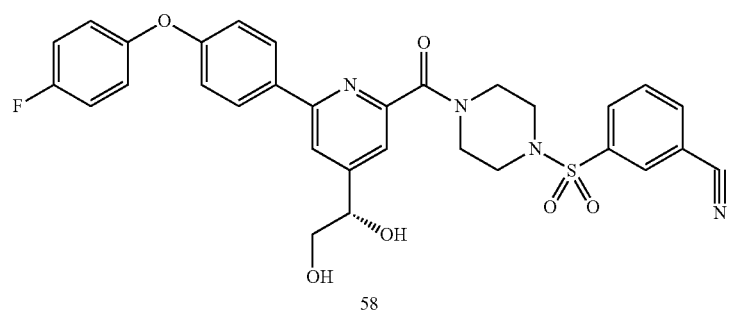

Synthesis of (S)-3-((4-(4-(1,2-dihydroxyethyl)-6-(4-(4-fluorophenoxy)phenyl)picolinoyl)piperazin-1-yl)sulfonyl)benzonitrile Compound 58 was synthesized in a similar way as that of compound 55 using compound 76 (60 mg, 0.13 mmol), 3-cyano phenylsulfonyl chloride (26 mg, 0.13 mmol), DIEA (0.1 mL), and DCM (2 mL) (yield 95%, (m/z+H)=603, $^1$HNMR ($CD_3OD$) δ ppm: 6.8-8.4 (m, 14H); 3.9 (s, 2H); 3.5 (s, 4H), 2.7-3.1 (m, 5H)).

Example 24

Synthesis of (S)—N-(1-amino-1-oxopropan-2-yl)-6-(4-((5-(trifluoromethyl)pyridin-2-yl)oxy)phenyl)picolinamide (compound 61)

Scheme 41

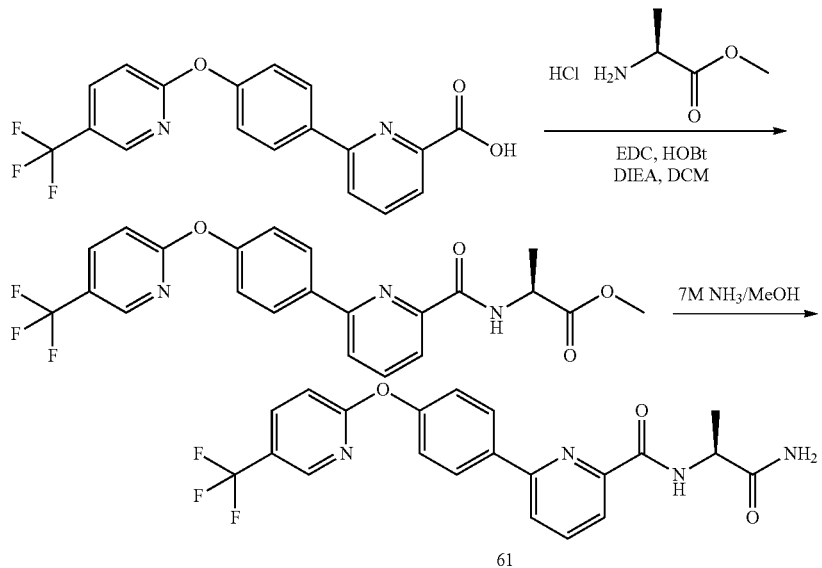

To a solution of acid (270 mg, 0.75 mmol) in DCM (15 mL) was added EDC (172.5 mg; 0.9 mmol) and HOBt (121.6 mg, 0.9 mmol). The reaction mixture was stirred for 1 h. L-alanine methyl ester hydrochloride (purchased from Sigma Aldrich; 104.7 mg, 0.75 mmol) and DIEA (0.2 ml, 1.13 mmol) were added thereto and stirring was continued for 20 h at room temperature. After the reaction was complete, $H_2O$ was added to quench the reaction. The reaction mixture was extracted with ethyl acetate and DCM. The organic phase was dried over anhydrous $Na_2SO_4$ and the solvent was evaporated. The crude product was chromatographed to give the intermediate ester (243 mg, 73% yield, $R_f$=0.4 (EtOA:Hexanes=1:1), LC/MS: m/z=446 [M+H]$^+$).

The intermediate ester (95 mg, 0.21 mmol) was dissolved in 7N $NH_3$/MeOH (5 mL) and stirred for 18 hrs. After the reaction was complete, the solvent was removed. The residue was purified by preparative TLC to give compound 61 as white solid (47 mg, 51% yield, LC/MS: m/z=431 [M+H]$^+$. $H^1$-NMR (400 MHz, CDCl$_3$): δ 8.48 (s, br, 1H), 8.28 (d, J=6.6 Hz, 2H), 8.03-8.15 (m, 4H), 7.33 (d, J=6.6 Hz, 2H), 7.22 (d, J=6.5 Hz, 1H), 4.68 (q, J=5.3 Hz, 1H), 1.56 (d, J=5.3 Hz, 3H)).

Example 25

Synthesis of Compound 62

Step 1:

Scheme 42

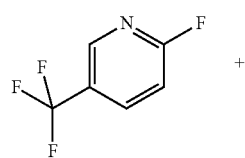

+

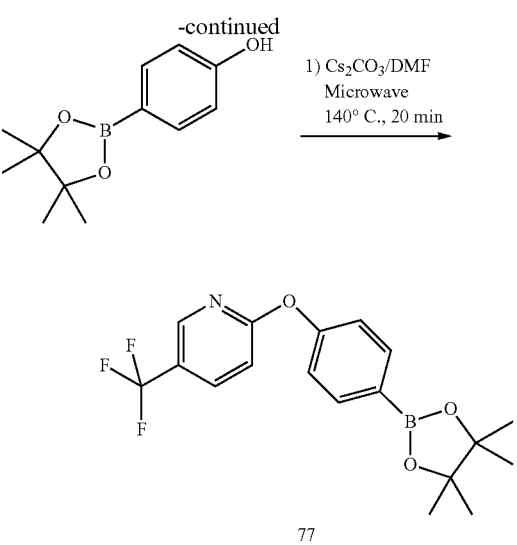

Synthesis of Compound 77

A 100 mL round bottom flask was charged with 5-fluoro-3-trifluoromethyl pridine (Matrix, 0.825 g, 5 mmol), 4-hydroxyl phenyl bronate (1.1 g, 5 mmol), $Cs_2CO_3$ (1.6 g, 5 mmol) and DMF (5 mL). The reaction mixture was stirred at 160° C. in a microwave for 20 min, cooled to room temperature, diluted with water, and extracted with ethyl acetate. The organic layer was separated and concentrated and crude product (compound 77) was used in the next step without further purification (1.46 g, yield 80%, (m/z+H)=366).

Step 2:

Scheme 43

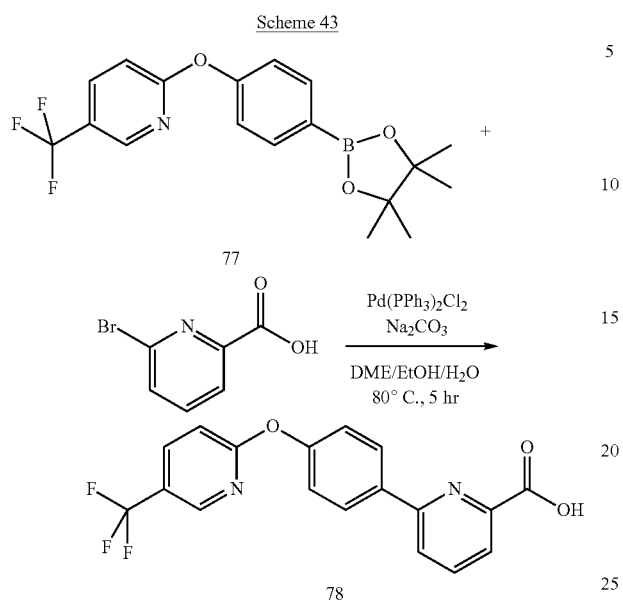

Synthesis of Compound 78

A 100 mL round bottom flask was charged with compound 77 (3.66 g, 10 mmol), 6-bromopyridine-2-carboxylic acid (Aldrich, 2.02 g, 10 mmol), Pd(PPh$_3$)$_2$Cl$_2$ (350 mg, 0.5 mmol) and a mixture of DME/H$_2$O/EtOH (10 mL/10 mL/5 mL). The reaction mixture was purged with Ar and stirred at 80° C. under Ar for 5 h. After cooling to room temperature, the reaction mixture was acidified with conc. HCl and extracted with EtOAc. The EtOAc was isolated, dried over MgSO$_4$, filtered, and concentrated. The residue was subjected to flash column chromatography (hexanes/EtOAc) on silica gel to give compound 78 as white solid (yield 80%, (m/z+H)=361).

Step 3:

Scheme 44

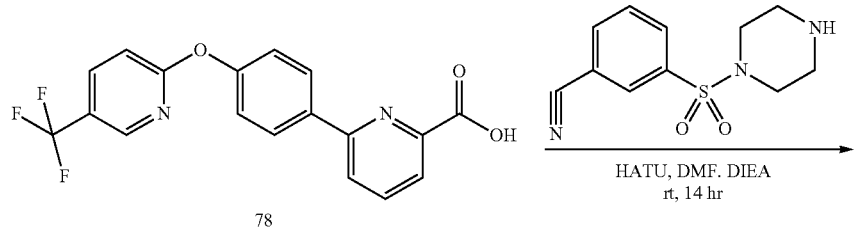

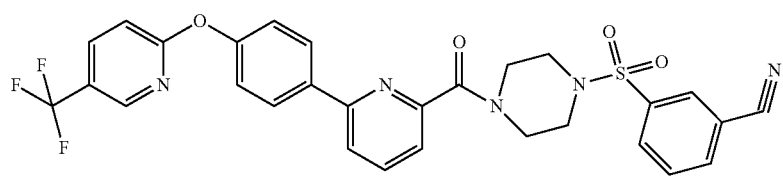

Synthesis of Compound 62

A 50 mL round bottom flask was charged with compound 78 (115.0 mg, 0.32 mmol), piperazine sulfonamide (80 mg, 0.32 mmol), HATU (130 mg, 0.34 mmol), DIEA (0.11 mL, 0.64 mmol) and DMF (1 mL). The reaction mixture was stirred at room temperature overnight, diluted with water, and extracted with ethyl acetate. The organic layer was concentrated and the residue was subjected to flash column chromatography (EtOAc/hexanes) on silica gel to give compound 62 as white solid (162 mg, yield 85%, (m/z+H)=594), $^1$HNMR (CDCl3) δ ppm: 8.4 (s, 1H); 6.7-8.3 (m, 13H); 3.85 (m, 4H); 3.25 (m, 4H)).

Example 26

Synthesis of N—((S)-1-amino-4-methyl-1-oxopentan-2-yl)-4-((S)-1,2-dihydroxyethyl)-6-(4-(4-fluorophenoxy)phenyl)picolinamide (compound 63)

Step 1:

Scheme 45

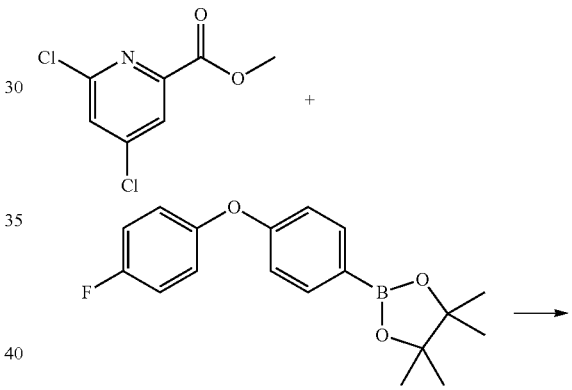

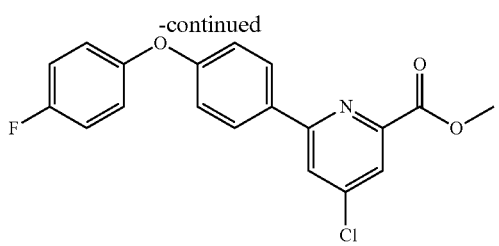

Synthesis of methyl 4-chloro-6-(4-(4-fluorophenoxy)phenyl)picolinate 4,6-Dichloropicolinate was synthesized according to the procedures described in WO 2006/053227. To a solution of the methyl 4,6-dichloropicolinate (2.52 g, 12.2 mmol) in dioxane (100 mL) was added 2-(4-(4-fluorophenoxy)phenyl)-4,4,5,5-tetramethyl-1,3,2-dioxaborolane (3.83 g, 12.2 mmol), 2M aqueous $Na_2CO_3$ solution (12.5 mL, 25 mmol) and $PdCl_2(dppf)$ (0.502 g, 0.62 mmol). The vessel was heated at reflux under nitrogen overnight. After cooling, the reaction was partitioned between 100 mL EtOAc and 50 mL brine and washed with additional brine. The organics were dried over MgSO4, filtered and concentrated in vacuo. The residue was dissolved in MeOH (150 mL) and concentrated $H_2SO_4$ (1.5 mL) was added. The vessel was heated at reflux under nitrogen overnight. After cooling the reaction was quenched by addition of 10 g $NaHCO_3$. The mixture was evaporated in vacuo and the residue partitioned between 100 mL EtOAc and 50 mL brine. The organics were washed once with 50 mL brine. The combined aqueous washes were extracted once with 50 mL EtOAc. The combined organics were dried over $MgSO_4$, filtered and concentrated in vacuo. The residue was chromatographed over silica gel eluting with 5-25% EtOAc in hexanes. The product fractions were isolated and evaporated in vacuo to yield the product methyl 4-chloro-6-(4-(4-fluorophenoxy)phenyl)picolinate as a pale tan oil (1.426 g, 3.99 mmol, 33% yield, LC/MS: m/z=358.1 [M+H]$^+$).

Step 2:

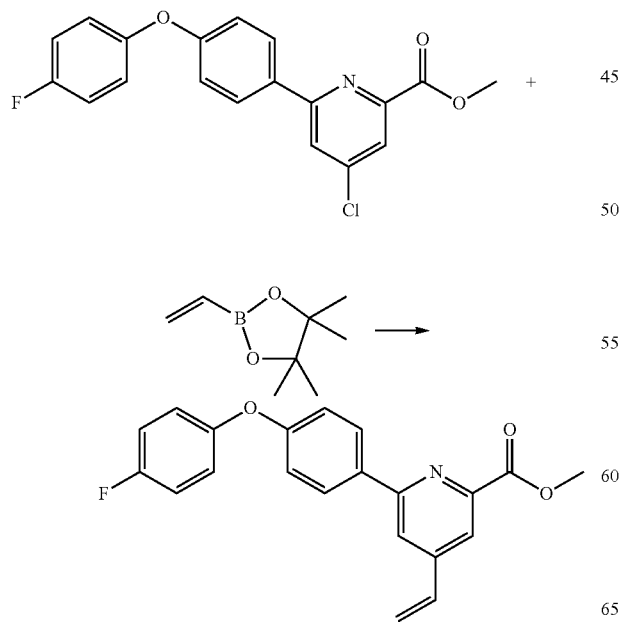

Synthesis of Methyl 6-(4-(4-fluorophenoxy)phenyl)-4-vinylpicolinate

To a solution of methyl 4-chloro-6-(4-(4-fluorophenoxy)phenyl)picolinate (1.416 g; 3.96 mmol) in 1M TBAF (12.0 mL; 12.0 mmol) in a pressure reaction tube was added 4,4,5,5-tetramethyl-2-vinyl-1,3,2-dioxaborolane (1.00 mL; 5.90 mmol) and $PdCl_2(dppf)$ (0.259 g; 0.32 mmol). The vessel was flushed with argon, capped and heated on an 80 C oil bath for 2 hours. After cooling, the reaction was partitioned between 100 mL EtOAc and 50 mL water. The organics were washed with an additional 50 mL water then 50 mL brine. The combined aqueous washed were extracted once with 50 mL EtOAc. The combined organics were dried over $MgSO_4$, filtered and concentrated in vacuo. The residue was chromatographed over silica gel eluting with 0-20% EtOAc in hexanes. The product fractions were isolated and evaporated in vacuo to yield the product methyl 6-(4-(4-fluorophenoxy)phenyl)-4-vinylpicolinate as a colorless oil (0.819 g, 2.34 mmol, 59% yield, LC/MS: m/z-350.2 [M+H]$^+$).

Step 3:

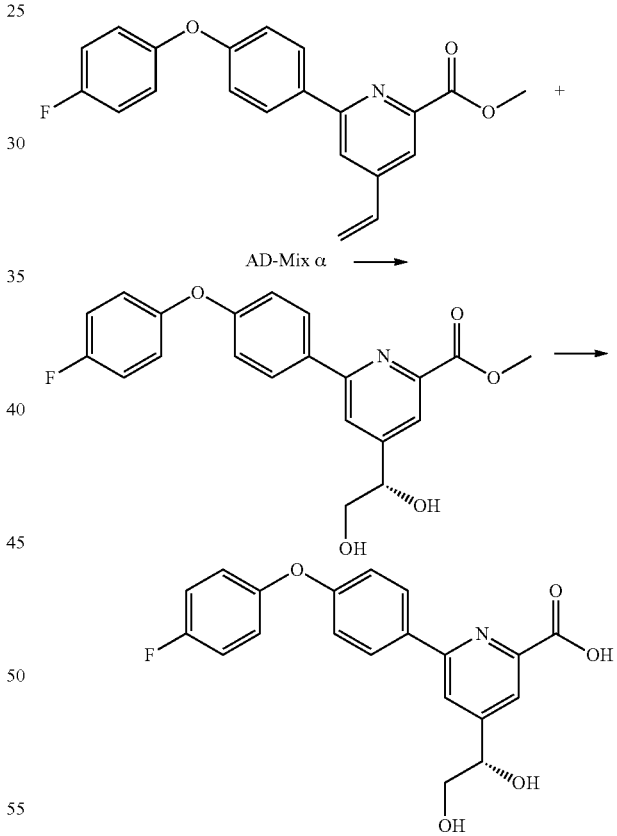

Synthesis of (S)-4-(1,2-dihydroxyethyl)-6-(4-(4-fluorophenoxy)phenyl)picolnic acid To a suspension of methyl 6-(4-(4-fluorophenoxy)phenyl)-4-vinylpicolinate (0.309 g, 0.884 mmol) in 10 mL 1:1 iPrOH/$H_2O$ was added AD-Mix α (1.205 g). The reaction was stirred for 3 h then partitioned between 50 mL EtOAc and 25 mL water. The organics were separated, dried over $MgSO_4$, filtered, and concentrated in vacuo to give crude (S)-methyl 4-(1,2-dihydroxyethyl)-6-(4-(4-fluorophenoxy)phenyl)picolinate which was used in the next step without further purification (LC/MS: m/z=384.1 [M+H]+).

To the crude (S)-methyl 4-(1,2-dihydroxyethyl)-6-(4-(4-fluorophenoxy)phenyl)picolinate (assume 0.884 mmol) in 5 mL of a 5:1 mixture of THF and water was added LiOH.H$_2$O (0.084 g, 2.00 mmol). The reaction was stirred overnight then evaporated in vacuo. The residue was dissolved in 5 mL water, filtered and acidified with 2.00 mL 1N HCl. The mixture was evaporated in vacuo to give the product (S)-4-(1,2-dihydroxyethyl)-6-(4-(4-fluorophenoxy)phenyl)picolinic acid mixed with lithium chloride (LC/MS: m/z=370.2 [M+H]+).

Step 4:

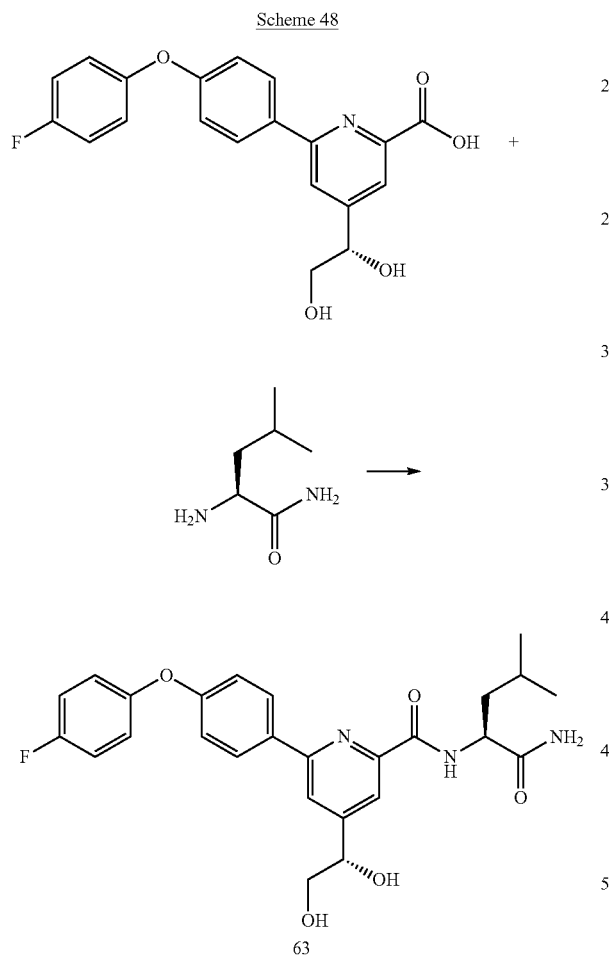

63

Synthesis of N—((S)-1-amino-4-methyl-1-oxopentan-2-yl)-4-((S)-1,2-dihydroxyethyl)-6-(4-(4-fluorophenoxy)phenyl)picolinamide To a solution of (S)-4-(1,2-dihydroxyethyl)-6-(4-(4-fluorophenoxy)phenyl)picolinic acid (assume 0.44 mmol) in DMF (5 mL) was added (S)-2-amino-4-methylpentanamide (0.074 g, 0.44 mmol), DIEA (0.20 mL, 1.1 mmol) and HBTU (0.201 g, 0.53 mmol). The reaction was stirred overnight then partitioned between 50 mL EtOAc and 50 mL brine. The organics were dried over Na$_2$SO$_4$, filtered and concentrated in vacuo. The residue was chromatographed over silica gel eluting with 25-75% acetone in hexanes. The product fractions were isolated and evaporated in vacuo. The residue was triturated with 5 mL 50% EtOAc/hexanes, filtered and rinsed with additional 50% EtOAc/hexanes. The solid was dried under vacuum at 50° C. to yield N—((S)-1-amino-4-methyl-1-oxopentan-2-yl)-4-((S)-1,2-dihydroxyethyl)-6-(4-(4-fluorophenoxy)phenyl)picolinamide (compound 63) as an off-white powder (0.105 g, 0.22 mmol, 50% yield, LC/MS: m/z=482.2 [M+H]+, $^1$H NMR (400 MHz, DMSO-d$_6$): δ 8.64 (d, J=9.2 Hz, 1H), 8.20 (d, J=8.4 Hz, 2H), 8.05 (s, 1H), 8.00 (s, 1H), 7.62 (s, 1H), 7.32-7.24 (m, 2H), 7.21-7.11 (m, 5H), 5.63 (d, J=4.8 Hz, 1H), 4.88-4.82 (m, 1H), 4.76-4.69 (m, 1H), 4.62-4.53 (m, 1H), 3.63-3.49 (m, 2H), 1.76-1.56 (m, 3H), 0.96-0.89 (m, 6H).

(R)-Methyl 4-(1,2-dihydroxyethyl)-6-(4-(4-fluorophenoxy)phenyl)picolinate and (R)-4-(1,2-dihydroxyethyl)-6-(4-(4-fluorophenoxy)phenyl)picolinic acid were prepared using the same sequence as above, but performing the dihydroxylation reaction with AD-Mix β instead of AD-Mix α.

N—((S)-1-amino-4-methyl-1-oxopentan-2-yl)-4-((R)-1,2-dihydroxyethyl)-6-(4-(4-fluorophenoxy)phenyl)picolinamide (compound 65) was prepared using the methodology described above as an off-white powder (0.121 g, 0.25 mmol, 56% yield, LC/MS: m/z=482.2 [M+H]+, $^1$H NMR (400 MHz, DMSO-d): δ 8.64 (d, J=8.8 Hz, 1H), 8.20 (d, J=8.8 Hz, 2H), 8.05 (s, 1H), 7.99 (s, 1H), 7.61 (s, 1H), 7.31-7.25 (m, 2H), 7.20-7.11 (m, 5H), 5.64 (d, J=4.8 Hz, 1H), 4.85 (t, J=6.0 Hz, 1H), 4.74-4.69 (m, 1H), 4.60-4.53 (m, 1H), 3.63-3.50 (m, 2H), 1.75-1.58 (m, 3H), 0.92 (t, J=5.2 Hz, 6H).

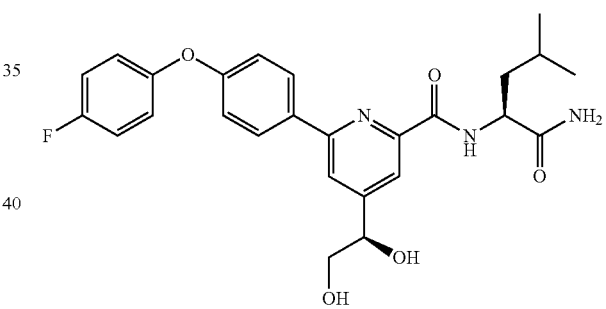

Example 27

Synthesis of (S)-2-(4-((S)-1,2-dihydroxyethyl)-6-(4-(4-fluorophenoxy)phenyl)picolinamido)succinamide (compound 64)

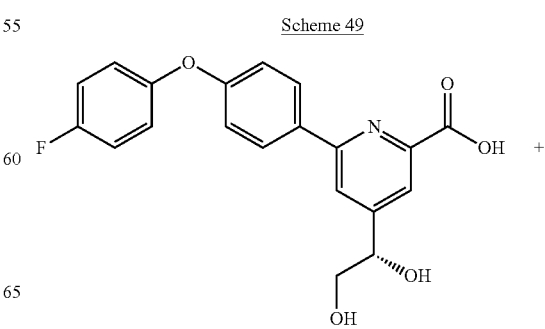

-continued

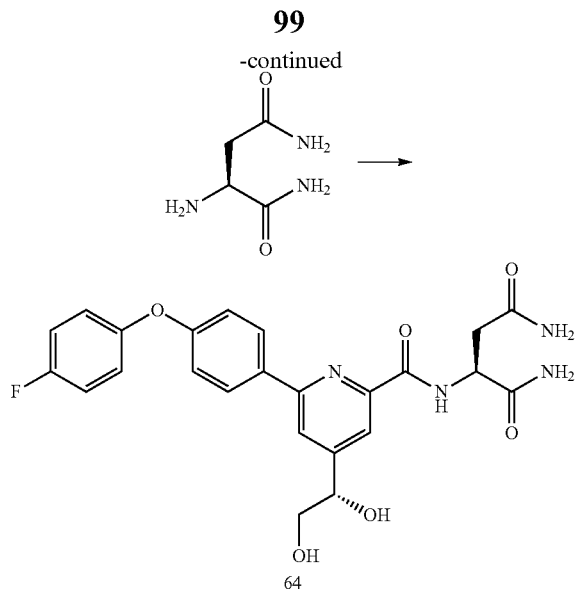

64

To a solution of (S)-4-(1,2-dihydroxyethyl)-6-(4-(4-fluorophenoxy)phenyl)picolinic acid (assume 0.44 mmol) in DMF (5 mL) was added (S)-2-aminosuccinamide (0.076 g, 0.45 mmol), DIEA (0.20 mL, 1.1 mmol) and HBTU (0.203 g, 0.54 mmol). The reaction was stirred overnight then partitioned between 50 mL EtOAc and 50 mL brine. The aqueous layer was extracted once more with 25 mL EtOAc and combined. The organics were dried over $Na_2SO_4$, filtered and evaporated in vacuo. The residue was crystallized from 4 mL warm acetone, the solid filtered off, rinsed with additional acetone and dried under vacuum at 50° C. to yield the product S)-2-(4-((S)-1,2-Dihydroxyethyl)-6-(4-(4-fluorophenoxy)phenyl)picolinamido)succinamide as a light tan powder (0.125 g, 0.26 mmol, 59% yield, LC/MS: m/z=483.1 $[M+H]^+$, $^1$H NMR (400 MHz, DMSO-$d_6$): δ 9.29 (d, J=8.4 Hz, 1H), 8.25 (d, J=8.8 Hz, 2H), 8.06 (s, 1H), 7.99 (s, 1H), 7.48 (s, 1H), 7.40 (s, 1H), 7.32-7.25 (m, 2H), 7.21-7.15 (m, 2H), 7.14-7.07 (m, 3H), 6.99 (s, 1H), 5.64 (d, J=4.8 Hz, 1H), 4.85 (t, J=6.0 Hz, 1H), 4.75-4.64 (m, 2H), 3.62-3.49 (m, 2H), 2.79-2.70 (m, 1H), 2.61-2.53 (m, 1H).

(S)-2-(4-((R)-1,2-dihydroxyethyl)-6-(4-(4-fluorophenoxy)phenyl)picolinamido) succinamide (compound 66) was prepared using the methodology described above as a cream-colored powder (0.128 g, 0.27 mmol, 59% yield, LC/MS: m/z=483.3 $[M+H]^+$, $^1$H NMR (400 MHz, DMSO-$d_6$): δ 9.29 (d, J=8.8 Hz, 1H), 8.25 (d, J=9.2 Hz, 2H), 8.06 (s, 1H), 7.99 (s, 1H), 7.47 (s, 1H), 7.40 (s, 1H), 7.32-7.25 (m, 2H), 7.21-7.15 (m, 2H), 7.14-7.07 (m, 3H), 6.99 (s, 1H), 5.65 (d, J=5.2 Hz, 1H), 4.86 (t, J=5.6 Hz, 1H), 4.75-4.64 (m, 2H), 3.62-3.49 (m, 2H), 2.79-2.71 (m, 1H), 2.61-2.53 (m, 1H).

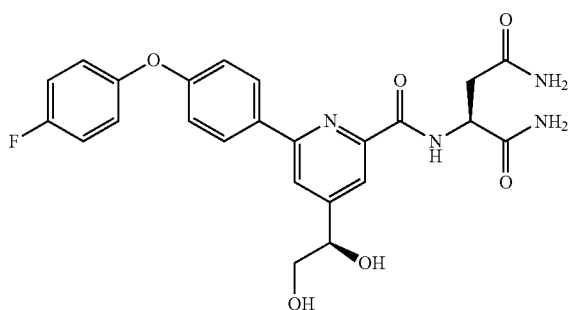 [SMILES: NC(=O)C[C@H](NC(=O)c1cc([C@@H](O)CO)cc(-c2ccc(Oc3ccc(F)cc3)cc2)n1)C(N)=O]

Example 28

Compounds of the invention have been tested in the FLIPR® or FLIPR$^{TETRA}$® sodium dye assay with KCl assay for sodium channel blocking activity, which is described in detail above. Representative values are presented in TABLE 2.

TABLE 2

| Evaluation of the tested compounds as sodium channel ($Na_v$) blockers | |
|---|---|
| COMPOUND # | $Na_v1.7$ $IC_{50}$ (μM) ± SEM |
| 7 | 0.19 ± 0.05 |
| 8 | 0.78 ± 0.17 |
| 10 | 0.43 ± 0.11 |
| 11 | 1.01 ± 0.09 |
| 12 | 0.14 ± 0.04 |
| 13 | 1.31 ± 0.18 |
| 14 | 0.22 ± 0.04 |
| 15 | 0.42 ± 0.04 |
| 16 | 0.32 ± 0.09 |
| 17 | 0.97 ± 0.13 |
| 18 | 3.48 ± 0.72 |
| 19 | 4.81 ± 0.18 |
| 21 | 0.39 ± 0.08 |
| 22 | 0.31 ± 0.03 |
| 23 | 0.39 ± 0.03 |
| 24 | 0.03 ± 0.04 |
| 37 | 4.02 ± 2.78 |
| 38 | 0.31 ± 0.03 |
| 39 | 0.75 ± 0.05 |
| 40 | 1.32 ± 0.16 |
| 41 | >20 |
| 42 | 2.12 ± 0.35 |
| 43 | 1.56 ± 0.50 |
| 44 | 0.34 ± 0.07 |
| 45 | 0.21 ± 0.04 |
| 46 | 0.61 ± 0.05 |
| 47 | 1.53 ± 0.33 |
| 48 | 0.55 ± 0.08 |
| 49 | 0.33 ± 0.02 |
| 51 | 2.89 ± 0.33 |
| 55 | 5.94 ± 0.73 |
| 56 | 6.81 ± 0.57 |
| 58 | 2.31 ± 0.62 |
| 59 | 0.34 ± 0.13 |
| 60 | 0.78 ± 0.10 |
| 61 | 4.34 ± 0.73 |
| 63 | 0.814 ± 0.231 |
| 64 | >20 |
| 65 | 1.564 ± 0.166 |
| 66 | >20 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having Formula V:

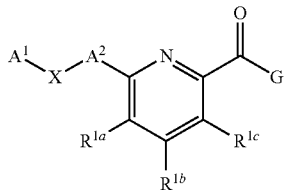

or a pharmaceutically acceptable salt or solvate thereof, wherein:

$A^1$ is optionally-substituted aryl;

X is
- a) —O—; or
- b) —$(CR^2R^3)_m$—;

wherein:
$R^2$ and $R^3$ are each independently selected from the group consisting of hydrogen and optionally substituted alkyl;

m is 0; and $A^2$ is phenyl that is 1,4-substituted with respect to

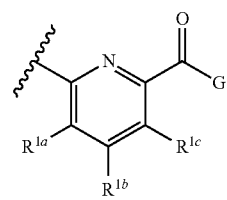

and X;

$R^{1a}$, $R^{1b}$, and $R^{1c}$ are each independently selected from the group consisting of:
- a) hydrogen;
- b) halogen;
- c) hydroxy;
- d) cyano;
- e) amino;
- f) carboxamido;
- g) optionally substituted alkyl;
- h) alkoxy; and
- i) haloalkoxy;

G is selected from the group consisting of:

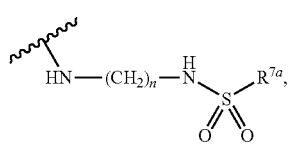

G-7

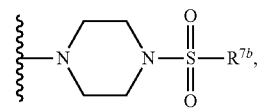

G-8

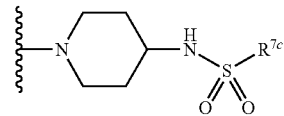

G-9

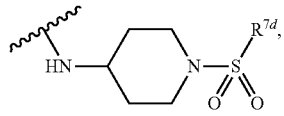

G-10

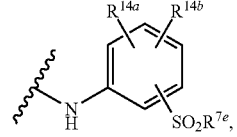

G-11

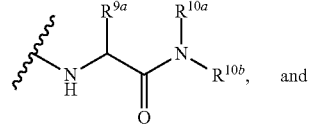

G-12

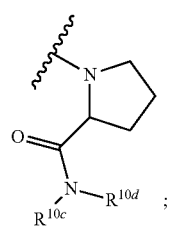

G-13 wherein:

$R^{9a}$ is:
- a) hydrogen;
- b) optionally substituted alkyl;
- c) optionally substituted aralkyl; or
- d) optionally substituted (heteroaryl)alkyl;

$R^{7a}$, $R^{7b}$, $R^{7c}$, $R^{7d}$, and $R^{7e}$ are each independently:
- a) optionally substituted alkyl;
- b) optionally substituted alkenyl;
- c) optionally substituted cycloalkyl;
- d) optionally substituted heterocyclo;
- e) optionally substituted aryl;
- f) optionally substituted heteroaryl;
- g) optionally substituted aralkyl; or
- h) optionally substituted (cycloalkyl)alkyl;- or
- i) $NR^{11a}R^{11b}$;

wherein:
$R^{11a}$ and $R^{11b}$ are each independently:
- a) hydrogen; or
- b) optionally substituted alkyl;

n is 2, 3, 4, or 5;

$R^{10a}$ and $R^{10b}$ are each independently:
- a) hydrogen; or
- b) optionally substituted alkyl;
or $R^{10a}$ and $R^{10b}$ taken together with the nitrogen atom to which they are attached form a 4- to 8-membered optionally substituted heterocyclo;

$R^{10c}$ and $R^{10d}$ are each independently:
- a) hydrogen;
- b) optionally-substituted alkyl;
- c) optionally-substituted alkenyl;
- d) optionally-substituted cycloalkyl;

e) optionally-substituted heterocyclo;

f) optionally-substituted aryl;

g) optionally-substituted heteroaryl, or h) optionally-substituted aralkyl; or $R^{10c}$ and $R^{10d}$ taken together with the nitrogen atom to which they are attached form a 4- to 8-membered optionally substituted heterocyclo; and $R^{14a}$ and $R^{14b}$ are each independently selected from the group consisting of:

a) hydrogen;

b) halogen;

c) hydroxy;

d) cyano;

e) alkyl;

f) haloalkyl;

g) alkoxy; and h) haloalkoxy;

wherein each of the optionally-substituted aryl, alkyl, alkenyl, cycloalkyl, heterocyclo, heteroaryl, (cycloalkyl)alkyl, (heteroaryl)alkyl, and aralkyl groups is either unsubstituted or substituted by one to three substituents independently selected from the group consisting of halo, halo($C_{1-6}$)alkyl, aryl, heterocyclo, cycloalkyl, $C_{1-6}$ alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxy($C_{1-6}$)alkyl, amino($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, azido, alkoxy, alkylthio, haloalkoxy, aryloxy, aralkyloxy, carboxy, carboxamido, sulfonamido, alkylsulfonyl, heteroaryl, alkylcarbonyl, aminocarbonyl, and mercapto($C_{1-6}$)alkyl.

2. A compound having Formula VIII:

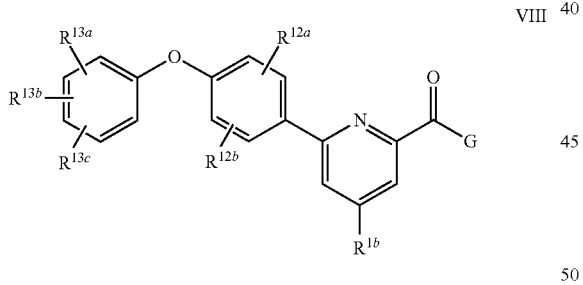

VIII or a pharmaceutically acceptable salt or solvate thereof, wherein:

$R^{1b}$ is selected from the group consisting of:

a) hydrogen;

b) halogen;

c) hydroxy;

d) cyano;

e) amino;

f) carboxamido;

g) optionally substituted alkyl;

h) alkoxy; and i) haloalkoxy;

G is selected from the group consisting of:

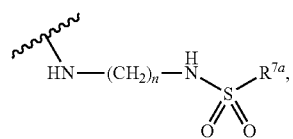
G-7

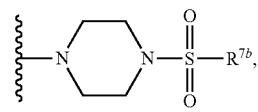
G-8

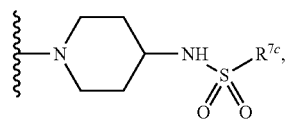
G-9

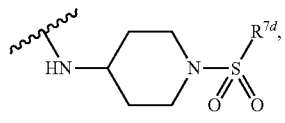
G-10

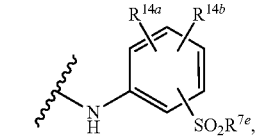
G-11

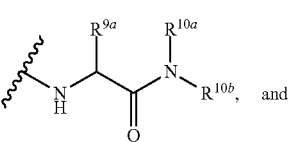
G-12 and

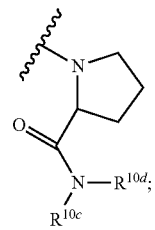
G-13 wherein:

$R^{9a}$ is:

a) hydrogen;

b) optionally-substituted alkyl;

c) optionally-substituted aralkyl; or d) optionally-substituted (heteroaryl)alkyl;

$R^{7a}$, $R^{7b}$, $R^{7c}$, $R^{7d}$, and $R^{7e}$ are each independently:

a) optionally-substituted alkyl;

b) optionally-substituted alkenyl;

c) optionally-substituted cycloalkyl;

d) optionally-substituted heterocyclo;

e) optionally-substituted aryl;

f) optionally-substituted heteroaryl;

g) optionally-substituted aralkyl;

h) optionally-substituted (cycloalkyl)alkyl; or i) $NR^{11a}R^{11b}$;

wherein:

$R^{11a}$ and $R^{11b}$ are each independently:

a) hydrogen; or b) optionally-substituted alkyl;

n is 2, 3, 4, or 5;

$R^{10a}$ and $R^{10b}$ are each independently:

a) hydrogen; or
b) optionally substituted alkyl;
or
$R^{10a}$ and $R^{10b}$ taken together with the nitrogen atom to which they are attached form a 4- to 8-membered optionally substituted heterocyclo;
$R^{10c}$ and $R^{10b}$ are each independently:
a) hydrogen;
b) optionally-substituted alkyl;
c) optionally-substituted alkenyl;
d) optionally-substituted cycloalkyl;
e) optionally-substituted heterocyclo;
f) optionally-substituted aryl;
g) optionally-substituted heteroaryl; or
h) optionally-substituted aralkyl; or
$R^{10c}$ and $R^{10d}$ taken together with the nitrogen atom to which they are attached form a 4- to 8-membered optionally substituted heterocyclo; and
$R^{14a}$ and $R^{14b}$ are each independently selected from the group consisting of:
a) hydrogen;
b) halogen;
c) hydroxy;
d) cyano;
e) alkyl;
f) haloalkyl;
g) alkoxy; and
h) haloalkoxy;
$R^{12a}, R^{12b}, R^{13a}, R^{13b}$, and $R^{13c}$ are each independently:
a) hydrogen;
b) halo;
c) nitro;
d) cyano;
e) hydroxy;
f) amino;
g) haloalkyl;
h) hydroxyalkyl;
i) alkoxy;
j) haloalkoxy;
k) aryloxy;
l) aralkyloxy;
m) alkylthio;
n) carboxamido;
o) sulfonamido;
p) optionally substituted alkyl;
q) optionally substituted cycloalkyl;
r) optionally substituted alkenyl;
s) optionally substituted alkynyl;
t) optionally substituted aryl;
u) optionally substituted heteroaryl;
v) optionally substituted heterocyclo; or
w) optionally substituted aralkyl;
wherein each of the optionally-substituted aryl, alkyl, alkenyl, alkynyl, cycloalkyl, heterocyclo, heteroaryl, (cycloalkyl)alkyl, (heteroaryl)alkyl, and aralkyl groups is optionally substituted by one to three substituents independently selected from the group consisting of halo, halo($C_{1-6}$)alkyl, aryl, heterocyclo, cycloalkyl, $C_{1-6}$ alkyl, $O_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxy($C_{1-6}$)alkyl, amino($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, azido, alkoxy, alkylthio, haloalkoxy, aryloxy, aralkyloxy, carboxy, carboxamido, sulfonamido, alkylsulfonyl, heteroaryl, alkylcarbonyl, aminocarbonyl, and mercapto($C_{1-6}$)alkyl.

3. The compound of claim 1, wherein G is selected from the group consisting of:

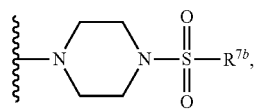
G-8

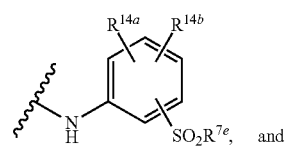
G-11

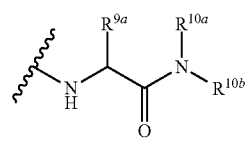
G-12 or a pharmaceutically acceptable salt or solvate thereof.

4. The compound of claim 3, wherein G is:

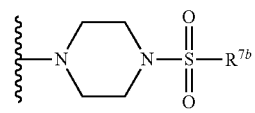
G-8 or a pharmaceutically acceptable salt or solvate thereof.

5. The compound of claim 1, wherein G is:

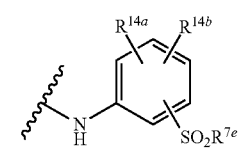
G-11 or a pharmaceutically acceptable salt or solvate thereof.

6. The compound of claim 1, wherein G is:

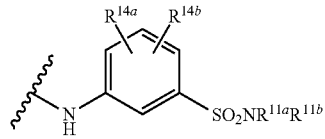

or a pharmaceutically acceptable salt or solvate thereof.

7. The compound of claim 1, wherein G is:
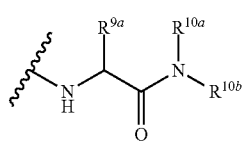
or a pharmaceutically acceptable salt or solvate thereof.
8. The compound of claim 7, wherein G is:
G-12 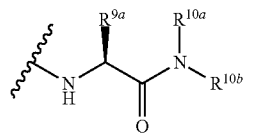
or a pharmaceutically acceptable salt or solvate thereof.
9. The compound of claim 1, wherein G is G-7 and n is 2, or a pharmaceutically acceptable salt or solvate thereof.
10. A compound selected from the group consisting of:
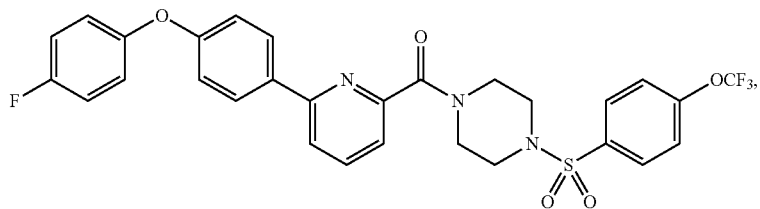
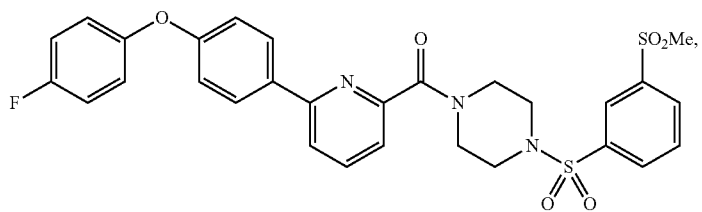
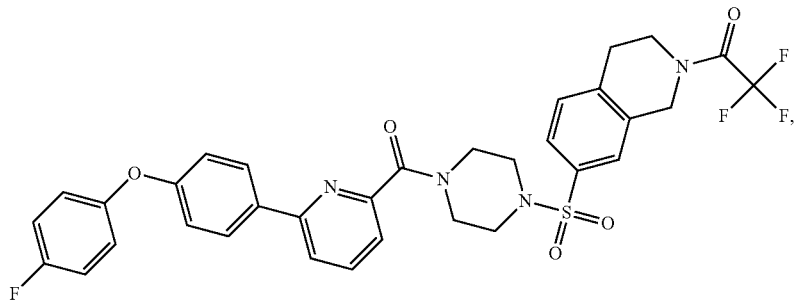
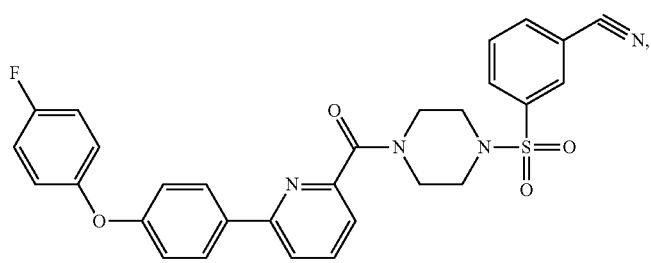
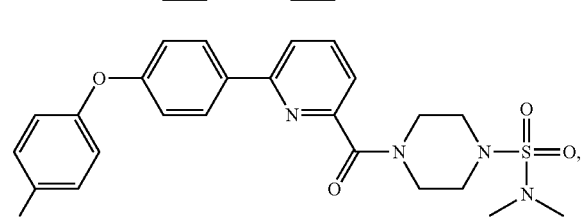
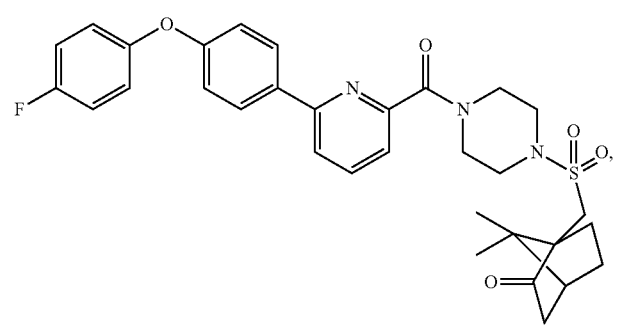

-continued
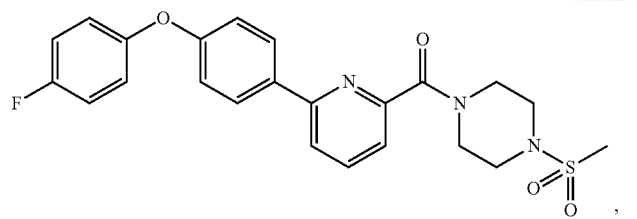
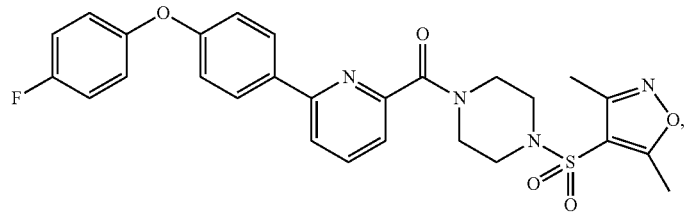
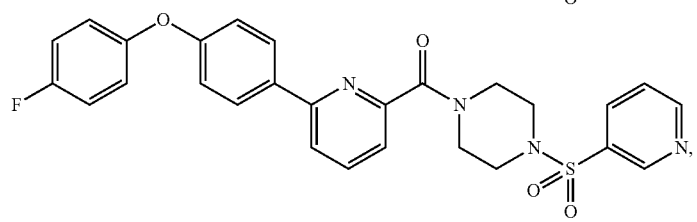
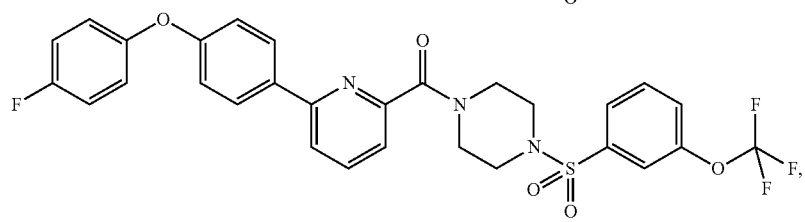
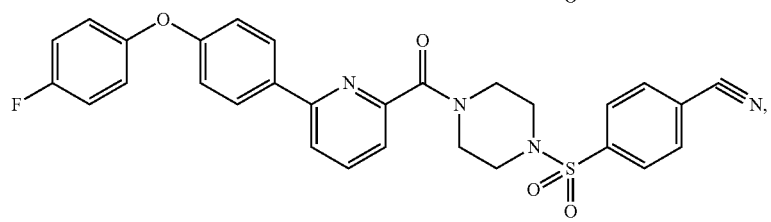
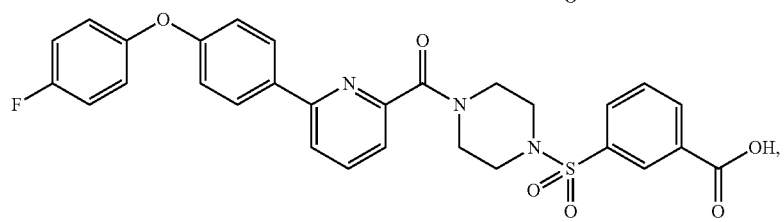
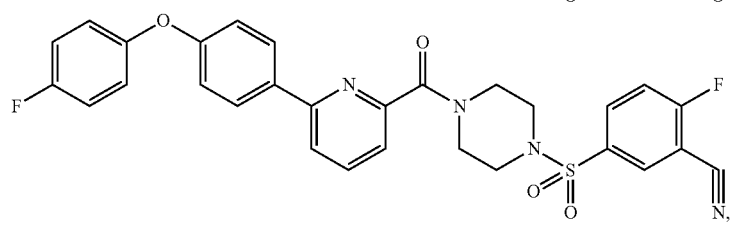
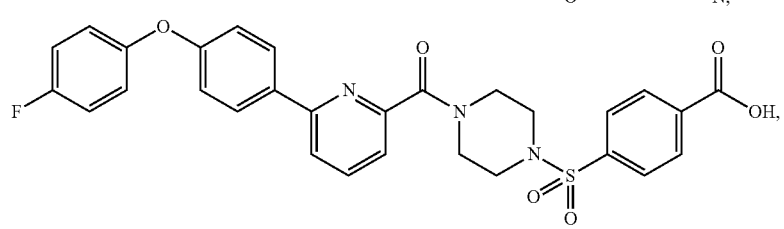

-continued
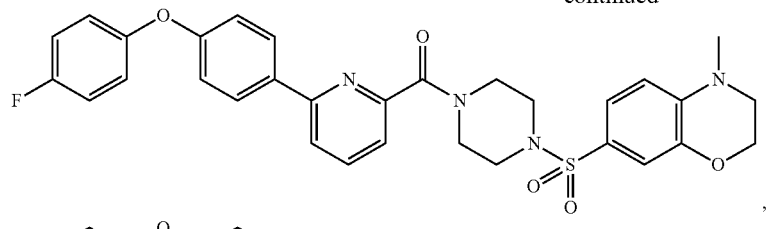
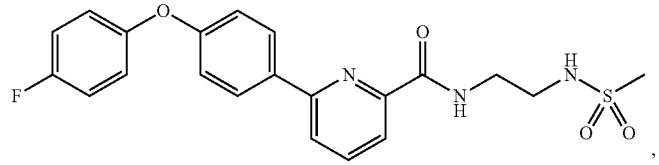
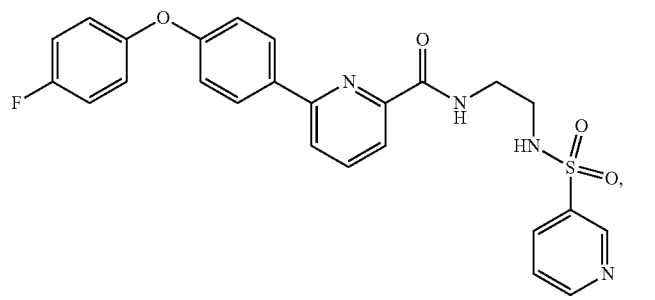
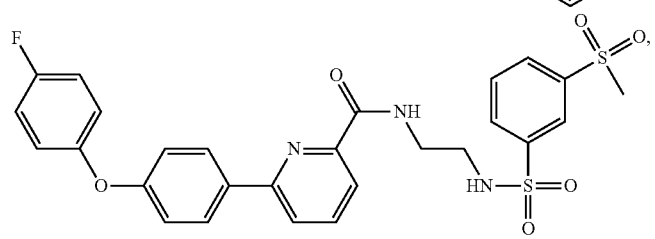
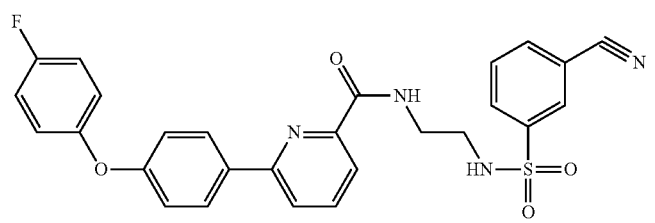
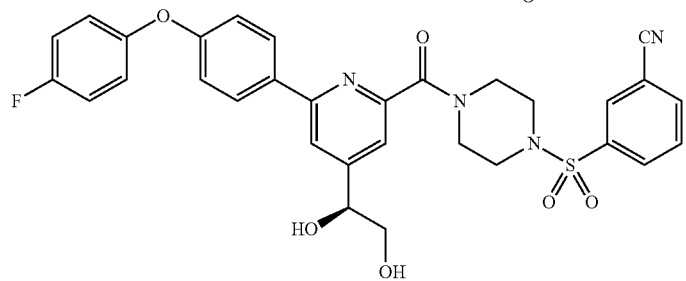
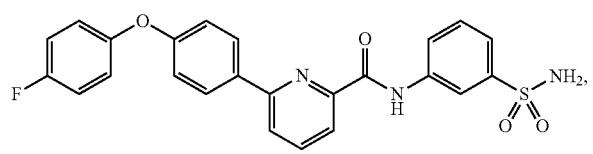 [SMILES: NS(=O)(=O)c1cccc(NC(=O)c2cccc(-c3ccc(Oc4ccc(F)cc4)cc3)n2)c1]

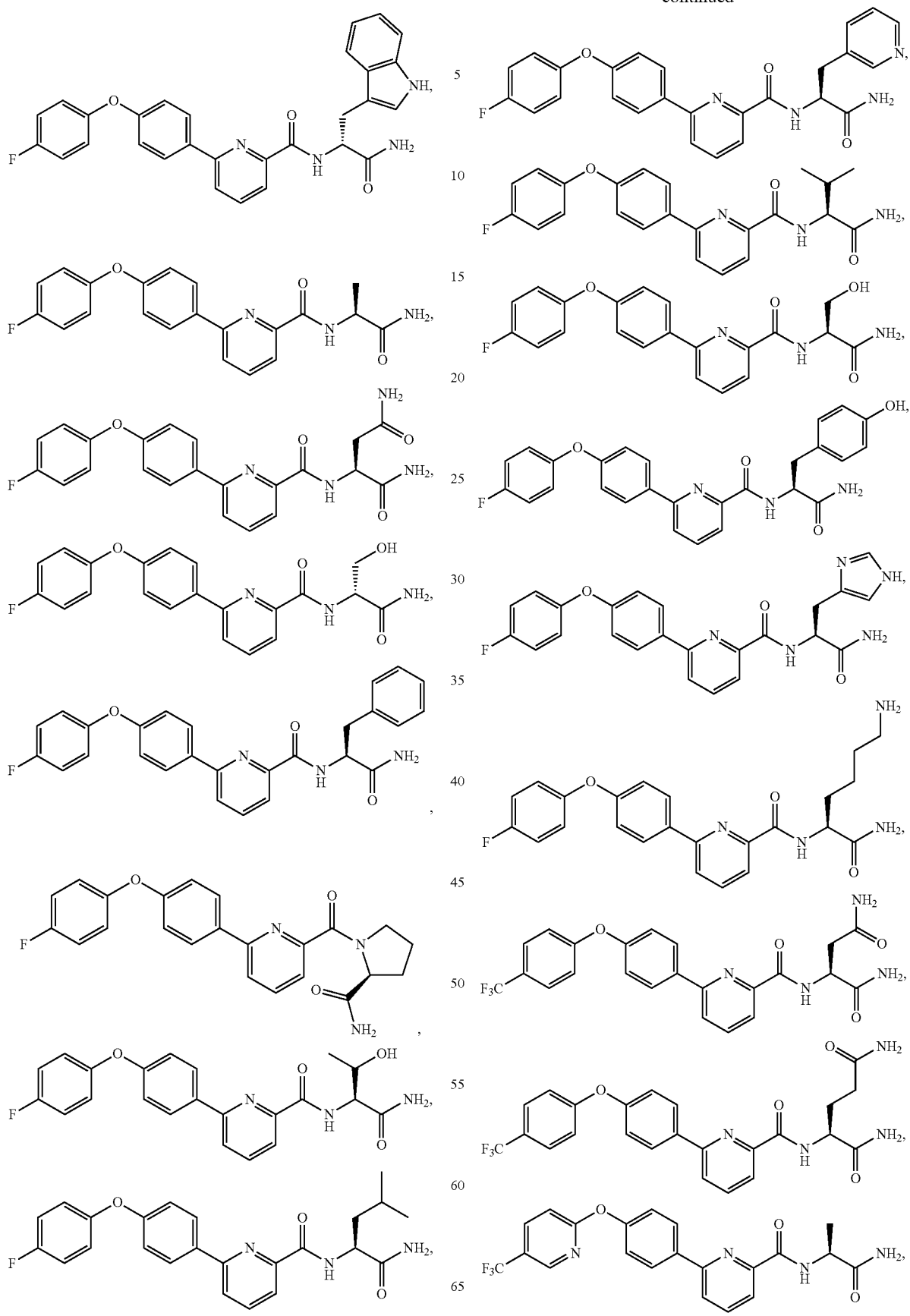

115
-continued

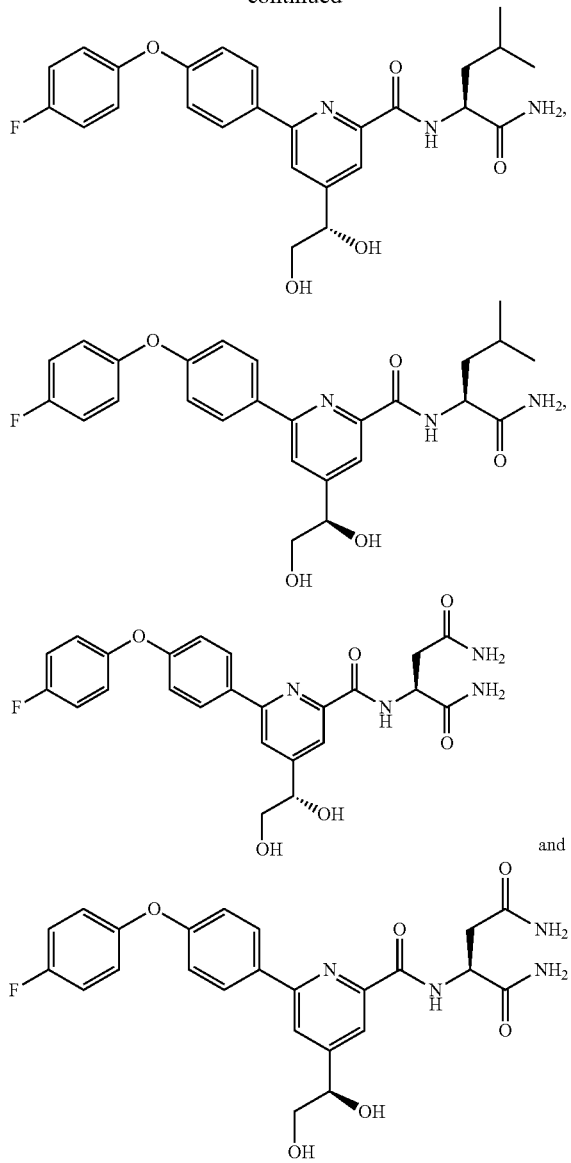

or a pharmaceutically acceptable or solvate thereof.

11. A pharmaceutical composition comprising the compound of claim 1 and a pharmaceutically acceptable carrier.

12. A method for treating pain in a mammal, comprising administering to a mammal in need of such treatment an effective amount of a compound of claim 1.

13. The method of claim 12, wherein said method is for preemptive or palliative treatment of pain.

14. The method of claim 12, wherein said pain is selected from the group consisting of chronic pain, inflammatory pain, neuropathic pain, acute pain, and surgical pain.

15. A method of modulating sodium channels in a mammal, comprising administering to the mammal at least one compound of claim 1.

16. The compound of claim 1, wherein the compound is $^3$H, $^{11}$C, or $^{14}$C radiolabeled, or a pharmaceutically acceptable salt or solvate thereof.

17. A method of preparing a pharmaceutical composition, comprising admixing a therapeutically effective amount of a compound of claim 1, or a pharmaceutically acceptable salt or solvate thereof, with a pharmaceutically acceptable carrier.

18. The compound of claim 2, wherein $R^{1b}$ is selected from the group consisting of hydrogen, amino, carboxamido, and optionally substituted alkyl.

19. A pharmaceutical composition comprising the compound of claim 10 and a pharmaceutically acceptable carrier.

20. A method for treating pain in a mammal comprising administering to a mammal in need of such treatment an effective amount of a compound of claim 10.

21. The method of claim 20, wherein said method is for preemptive or palliative treatment of pain.

22. The method of claim 20, wherein said pain is selected from the group consisting of chronic pain, inflammatory pain, neuropathic pain, acute pain, and surgical pain.

* * * * *